US010556034B2

(12) United States Patent
Jin et al.

(10) Patent No.: US 10,556,034 B2
(45) Date of Patent: Feb. 11, 2020

(54) SWITCHABLE DIGITAL SCENT GENERATION AND RELEASE, AND VAPOR AND LIQUID DELIVERY METHODS AND SYSTEMS

(71) Applicants: The Regents of the University of California, Oakland, CA (US); Sensable Technologies LLC, San Diego, CA (US)

(72) Inventors: Sungho Jin, San Diego, CA (US); Calvin Gardner, La Jolla, CA (US); Stewart Matthew, London (GB)

(73) Assignees: The Regents of the University of California, Oakland, CA (US); Sensable Technologies LLC, New York, NY (US)

(*) Notice: Subject to any disclaimer, the term of this patent is extended or adjusted under 35 U.S.C. 154(b) by 269 days.

(21) Appl. No.: 15/565,650

(22) PCT Filed: Apr. 11, 2016

(86) PCT No.: PCT/US2016/026971
§ 371 (c)(1),
(2) Date: Oct. 10, 2017

(87) PCT Pub. No.: WO2016/164917
PCT Pub. Date: Oct. 13, 2016

(65) Prior Publication Data
US 2018/0071425 A1    Mar. 15, 2018

Related U.S. Application Data

(60) Provisional application No. 62/145,918, filed on Apr. 10, 2015, provisional application No. 62/174,450, filed on Jun. 11, 2015.

(51) Int. Cl.
*A61L 9/00* (2006.01)
*A62C 13/62* (2006.01)
(Continued)

(52) U.S. Cl.
CPC ............... *A61L 9/035* (2013.01); *A61L 9/037* (2013.01); *A61L 9/125* (2013.01); *A61L 9/127* (2013.01);
(Continued)

(58) Field of Classification Search
CPC . A61L 9/125; A61L 9/122; A61L 9/14; B05B 17/0669; B64D 13/06
(Continued)

(56) References Cited

U.S. PATENT DOCUMENTS 5,565,148 A    10/1996    Pendergrass, Jr.
5,949,522 A    9/1999    Manne
(Continued)

FOREIGN PATENT DOCUMENTS

WO    2014176291 A1    10/2014

OTHER PUBLICATIONS

Jin, S., "Deformation-Induced Anisotropic Cr—Co—Fe Permanent Magnet Alloys", IEEE Trans., MAG-15, 1979, p. 1748.
(Continued)

*Primary Examiner* — Monzer R Chorbaji
(74) *Attorney, Agent, or Firm* — Perkins Coie LLP

(57) ABSTRACT

Methods, devices and systems are described for digitally creating new scents or digitally dispensing gas, vapor, or liquid substances. A device includes a container or replaceable cartridge including one or more chambers containing one or more scented substances; a housing structured to include a compartment to hold the cartridge, an opening to allow the one or more scented or unscented substances to dispense to an outer environment from the device, and one
(Continued)

or more transporting channels formed between the compartment and the opening, in which each of the one or more transporting channels is configured to deliver a scented substance from the corresponding chamber to the opening for delivering a scent from the one or more scented substances; and an actuator switch arranged in a corresponding transporting channel and rapidly operable to move between an open position and closed position based on an applied signal to selectively allow passage of the scented or unscented substance from the corresponding transporting path.

24 Claims, 67 Drawing Sheets

(51) Int. Cl.
*B05B 1/24* (2006.01)
*B05B 7/08* (2006.01)
*A61L 9/03* (2006.01)
*A61L 9/14* (2006.01)
*A61L 9/12* (2006.01)

(52) U.S. Cl.
CPC ............ *A61L 9/14* (2013.01); *A61L 2209/111* (2013.01); *A61L 2209/132* (2013.01); *A61L 2209/133* (2013.01); *A61L 2209/135* (2013.01); *A61L 2209/14* (2013.01)

(58) Field of Classification Search
USPC ........ 422/5, 305–306; 239/80, 303, 548–549
See application file for complete search history.

(56) References Cited

U.S. PATENT DOCUMENTS

| | | | |
|---|---|---|---|
| 6,325,475 | B1 | 12/2001 | Hayes et al. |
| 6,371,451 | B1* | 4/2002 | Choi ................... A45D 34/02 |
| | | | 261/115 |
| 63,090,453 | | 5/2002 | Frederickson et al. |
| 6,803,987 | B2* | 10/2004 | Manne .................. A61L 9/122 |
| | | | 352/85 |
| 7,883,264 | B1* | 2/2011 | Liva ........................ A61L 9/03 |
| | | | 239/413 |
| 2001/0028119 | A1 | 10/2001 | Wittek |
| 2005/0046059 | A1 | 3/2005 | Watkins et al. |
| 2013/0312749 | A1 | 11/2013 | Bomn et al. |
| 2014/0001286 | A1 | 1/2014 | Scott et al. |

OTHER PUBLICATIONS

Jin et al., "Low Cobalt Cr—Co—Fe Magnet Alloys by Slow Cooling Under Magnetic Field", IEEE Trans. Magnetics, MAG-16, 1980, p. 526.

European Communication for European Patent Application No. 16777498.3, dated Nov. 21, 2018, 17 pages.

International Search Report and Written Opinion for PCT Application No. PCT/US2016/026971, dated Sep. 15, 2016, 24 pages.

* cited by examiner

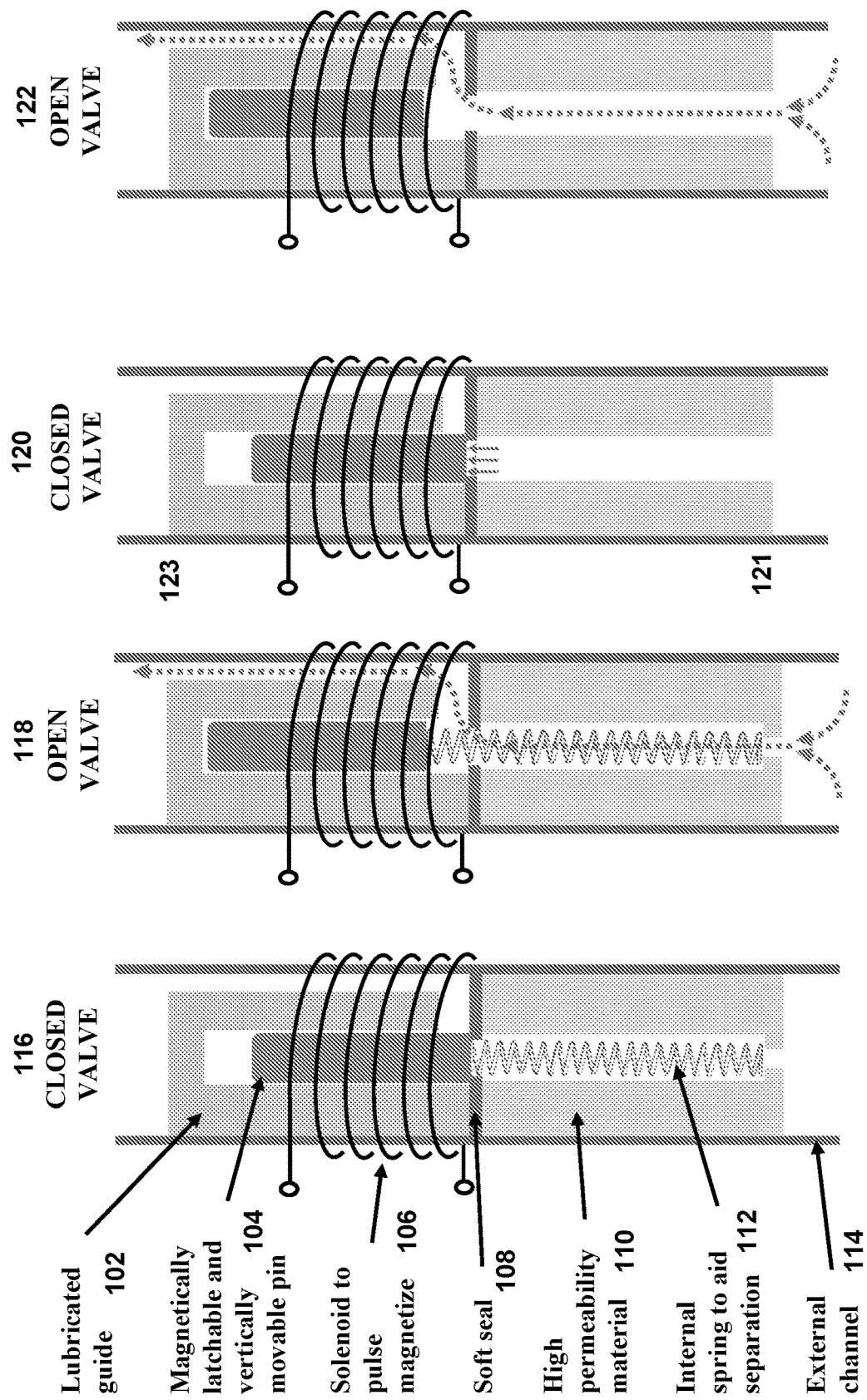

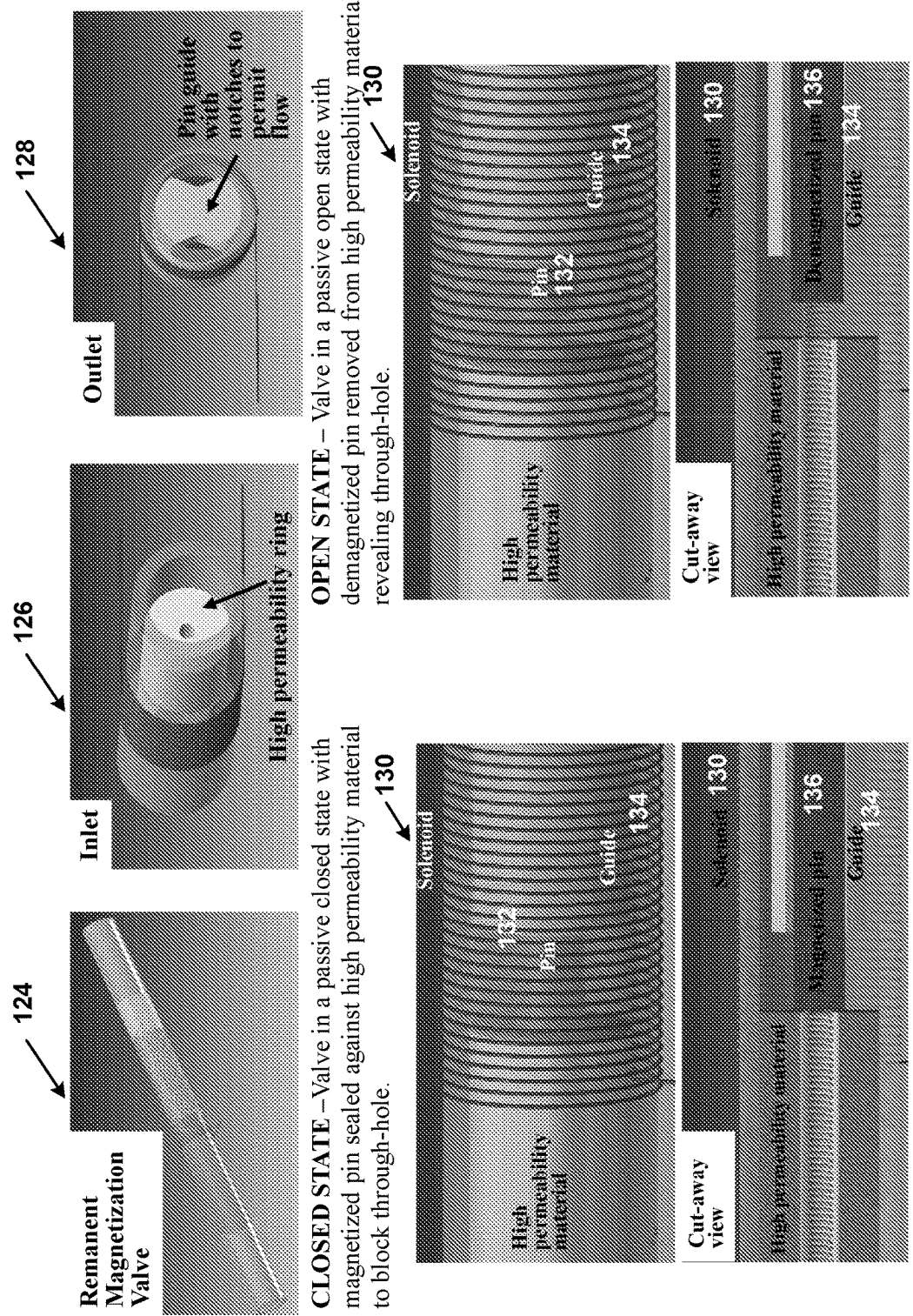

FIG. 1 (C) – Remanent Magnetization Valve Details: In addition to controlling gas flow, miniaturized remanent magnetization valves may be used to control drug release, possibly in a wearable configuration where the gas, vapor-state, mist-state, suspensions, or powder drug doses are administered on schedule or as needed as programed by software. Hardwire connected actuations as well as wired or wireless activations (wifi, optical, laser and other broadcast transmission) are possible.

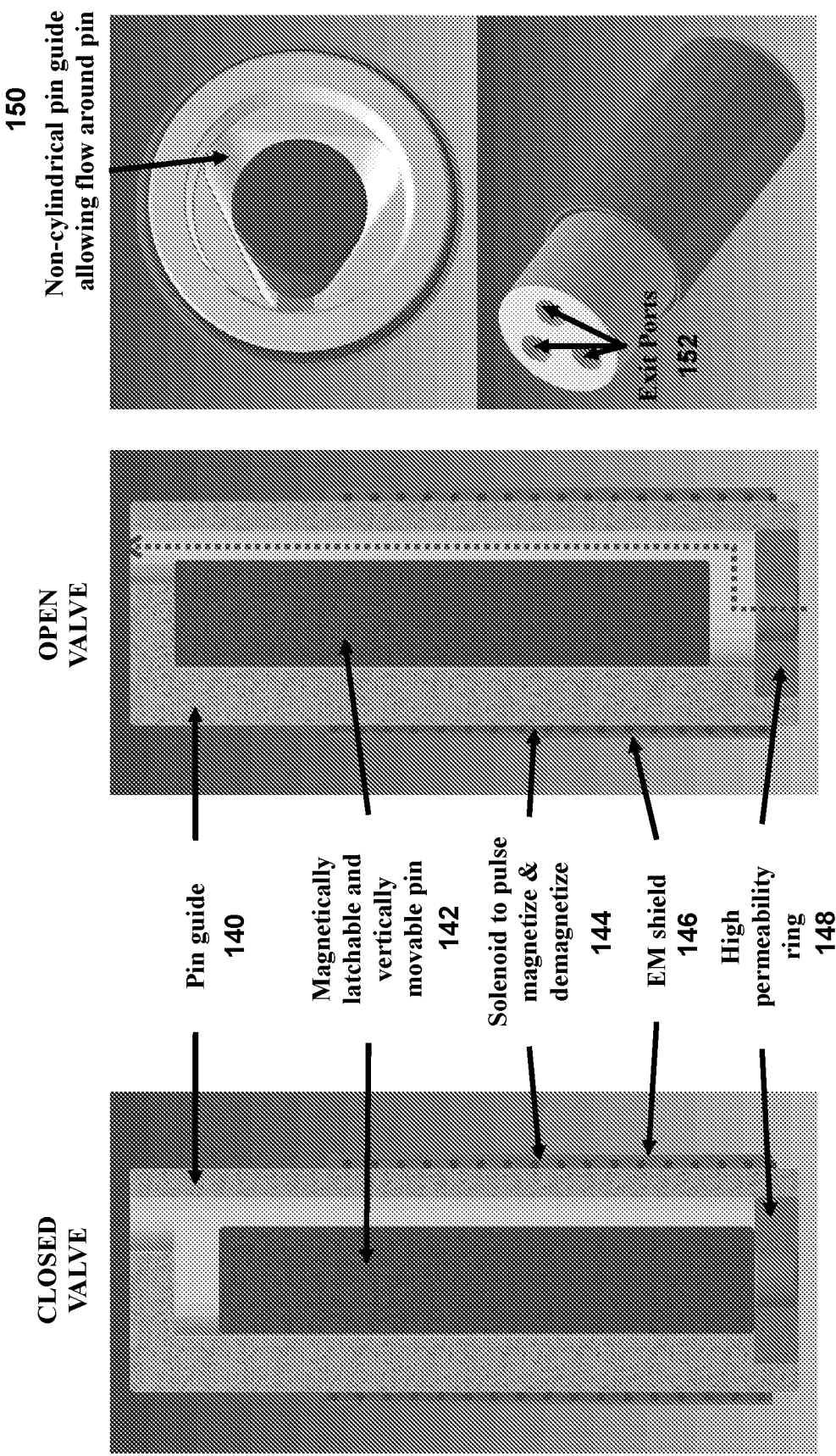
FIG. 1 (D) – Remanent Magnetization Valve with Non-cylindrical Pin Guide: Half-section views showing fluid path for closed and open valves. The non-cylindrical pin guide permits flow around the pin (viewable when high permeability ring is removed) and through the exit ports.

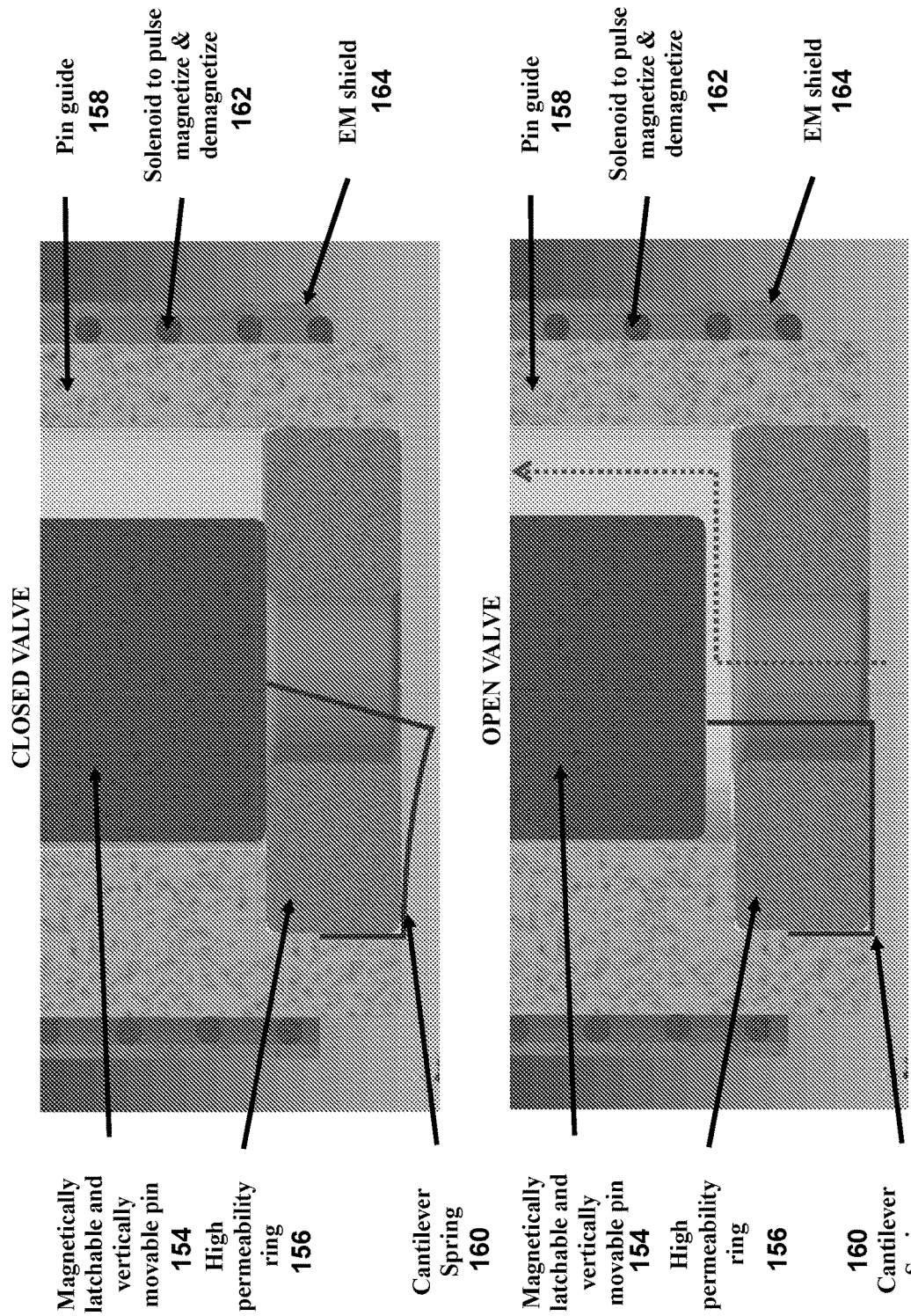
FIG. 1 (E) – Half Section of Remanent Magnetization Valve with Cantilevered Spring Separation: Following demagnetization, pin separation is accomplished via elastic response of a cantilevered spring. When magnetized, the attraction force is sufficient to overcome the spring force and fully close the valve.

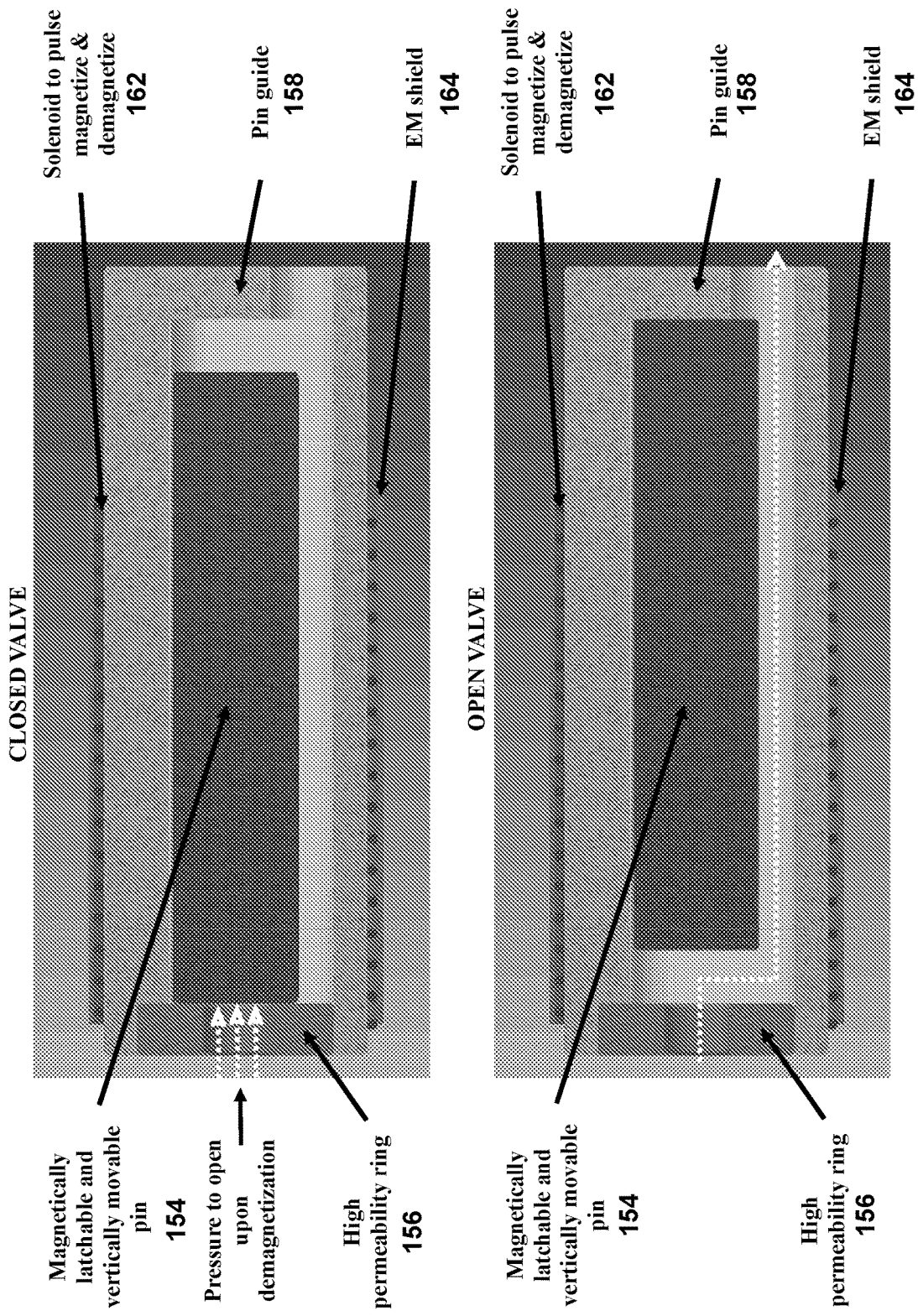
FIG. 1 (F) – Half Section of Remanent Magnetization Valve with Pressure-Based Separation: Following demagnetization, pin separation is accomplished via pressurization. When magnetized, the attraction force is sufficient to withstand pressurization.

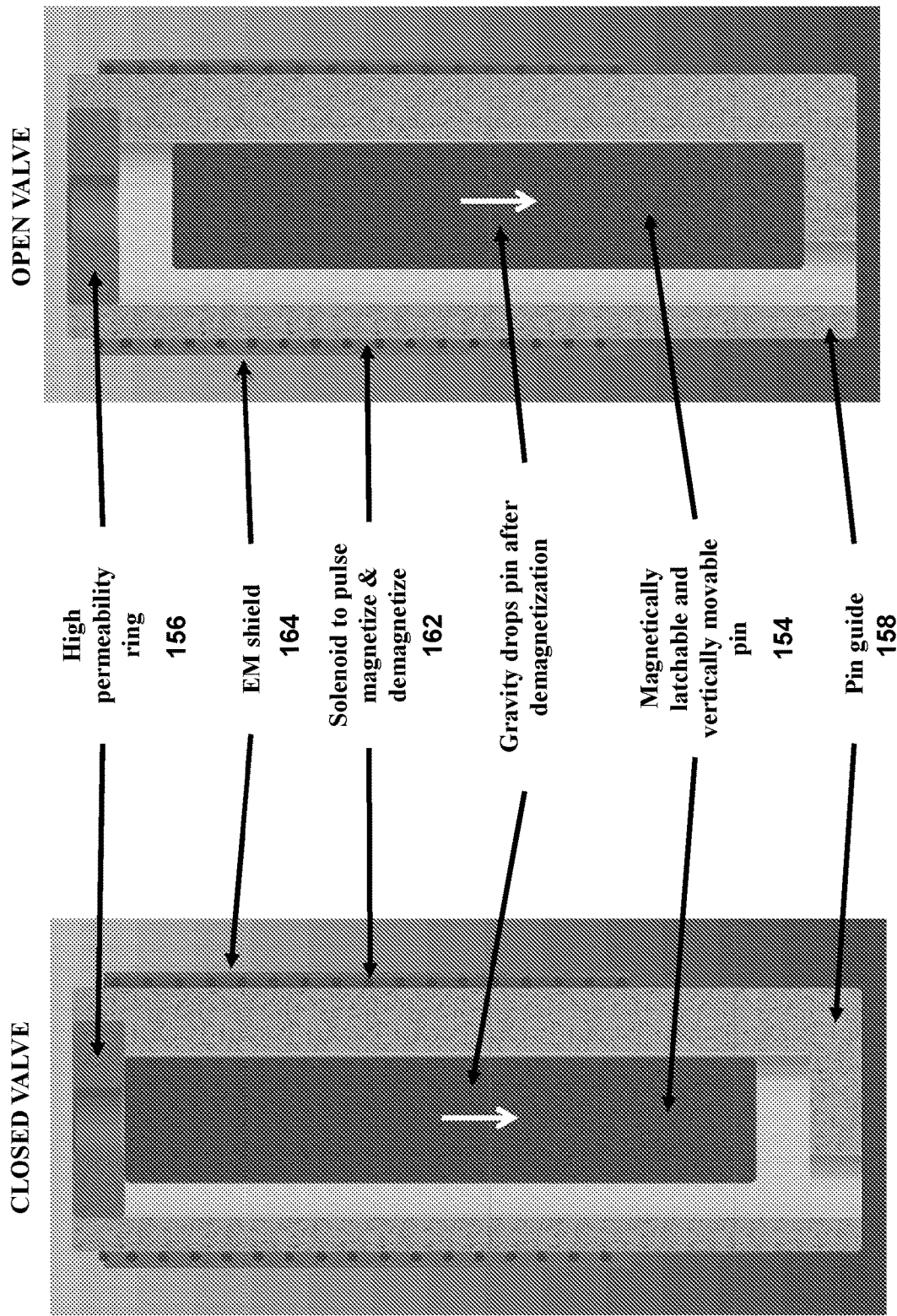
FIG. 1 (G) – Half Section of Remanent Magnetization Valve with Gravity Separation: Following demagnetization, pin separation is accomplished via gravitational acceleration on the pin. When magnetized, the attraction force is sufficient to overcome the gravitational force and close the valve.

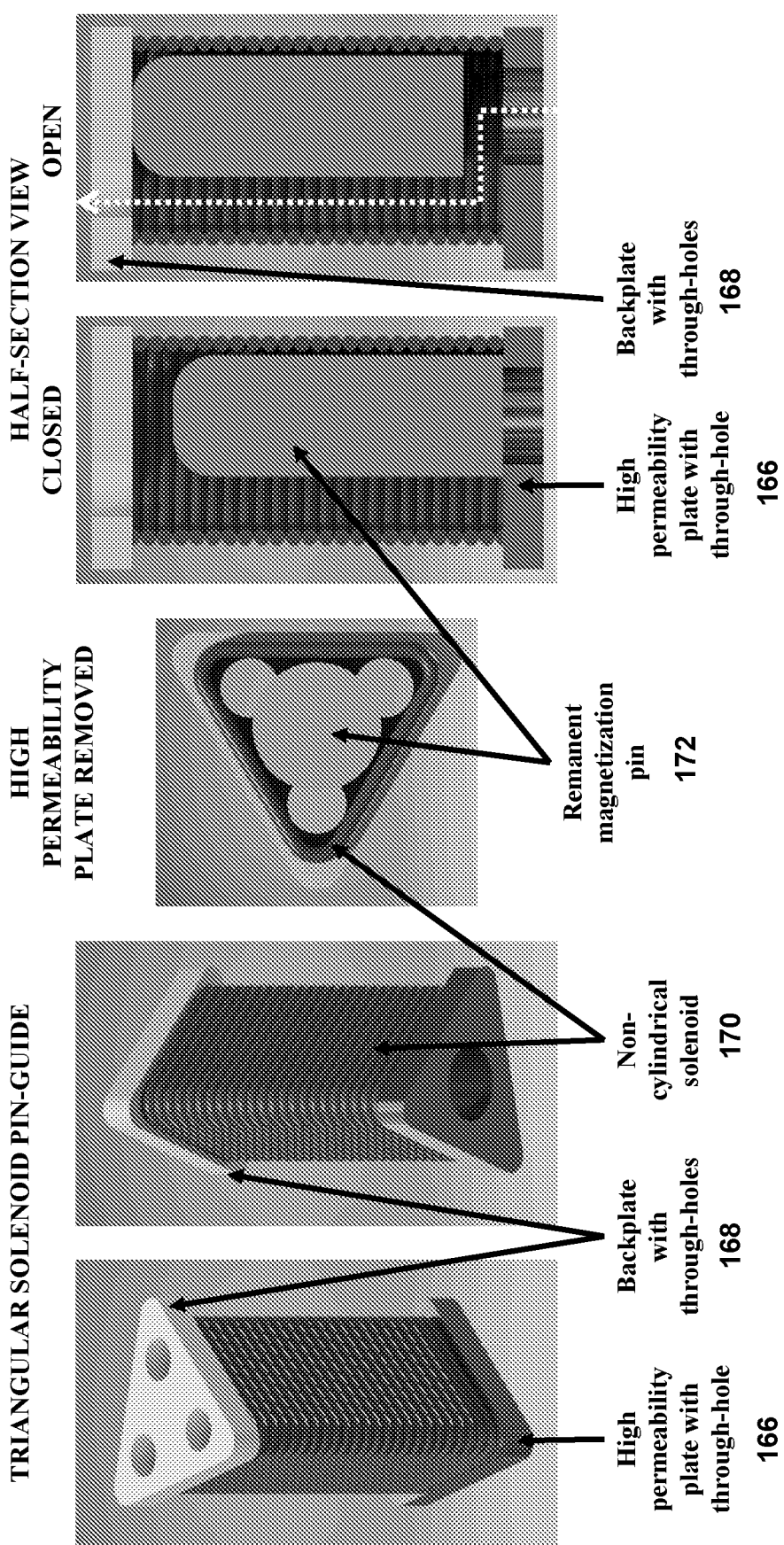
FIG. 1 (H) – Remanent Magnetization Valve with Non-cylindrical Solenoid: A non-cylindrical solenoid combines the effectiveness of a non-cylindrical pin guide and wrapping solenoid from FIG. 1 (D) – (G). The design has the added advantage of maximizing field strength efficiency to magnetize or demagnetize the pin.

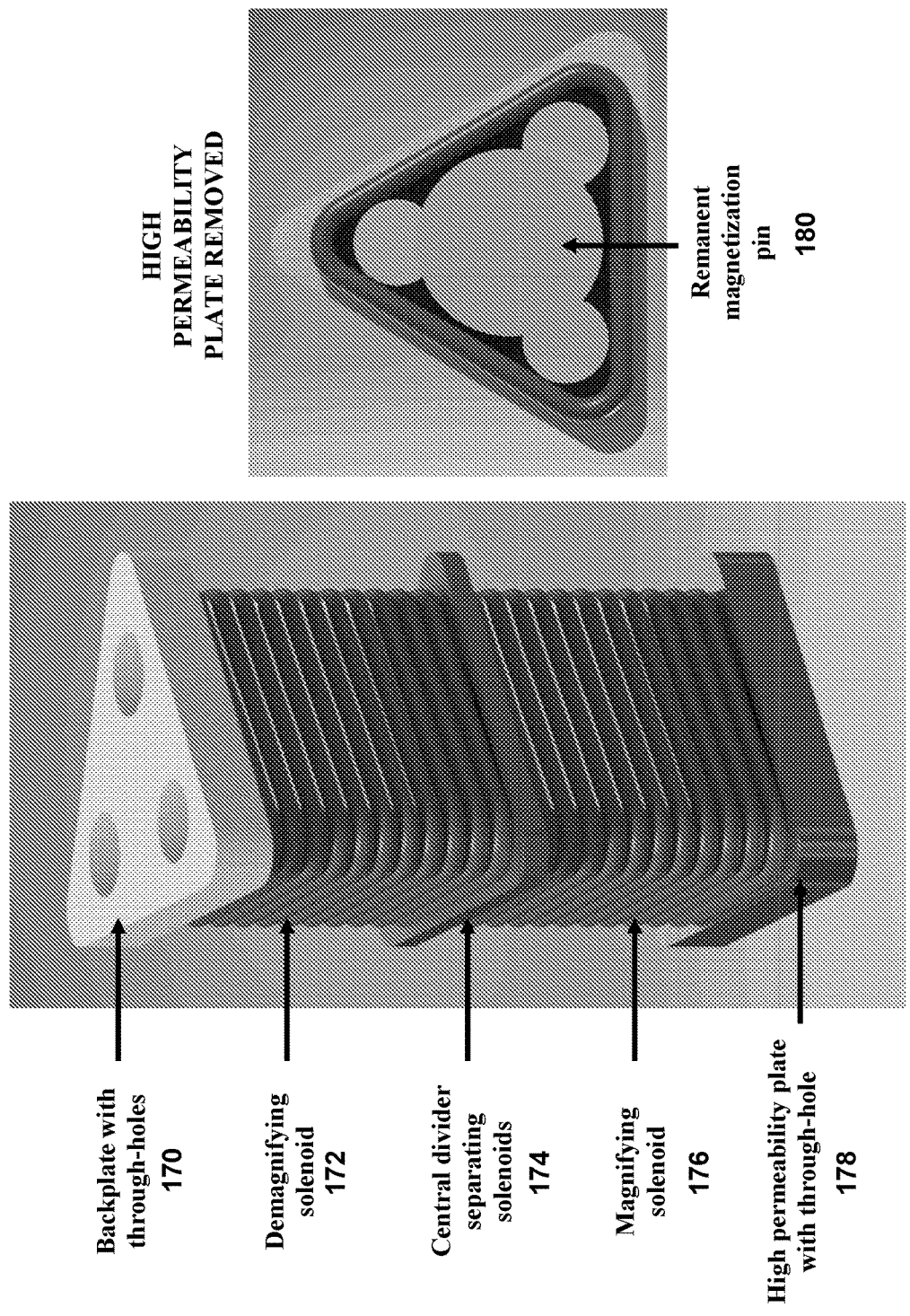

FIG. 1 (I) – Remanent Magnetization Valve with Dual Solenoids: In addition to the single solenoid designs presented in FIG. 1 (A) – (H), a dual solenoid system separates the magnetization and demagnetization responsibilities for the remanent magnetization pins. A dual solenoid is shown here applied to a non-cylindrical design. The design is equally applicable to the remanent magnetization valve designs from FIG. 1 (A) – (G).

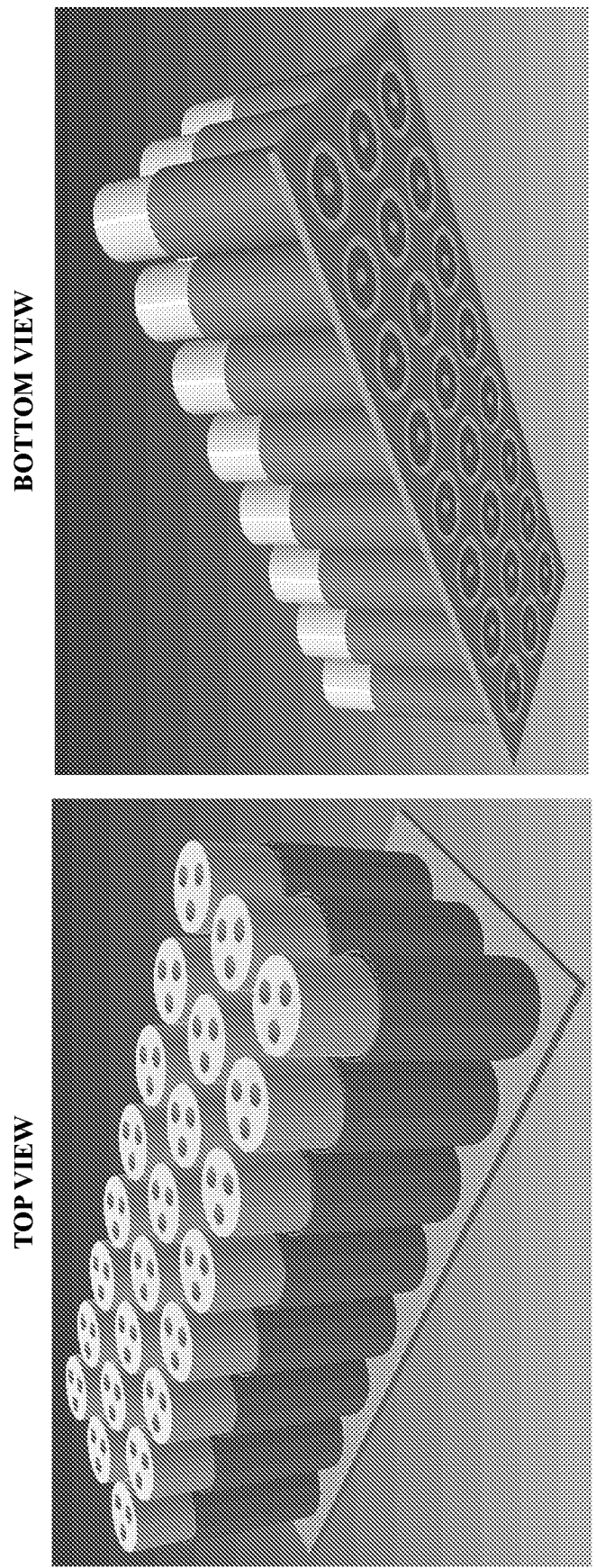
FIG. 1 (J) – Remanent Magnetization Valve Array for Scented or Unscented Fluid Release: An example 3x8 array of remanent magnetization valves. The array mates to an array of scent or other ingredients such that one or multiple ingredients can be released via valve activation.

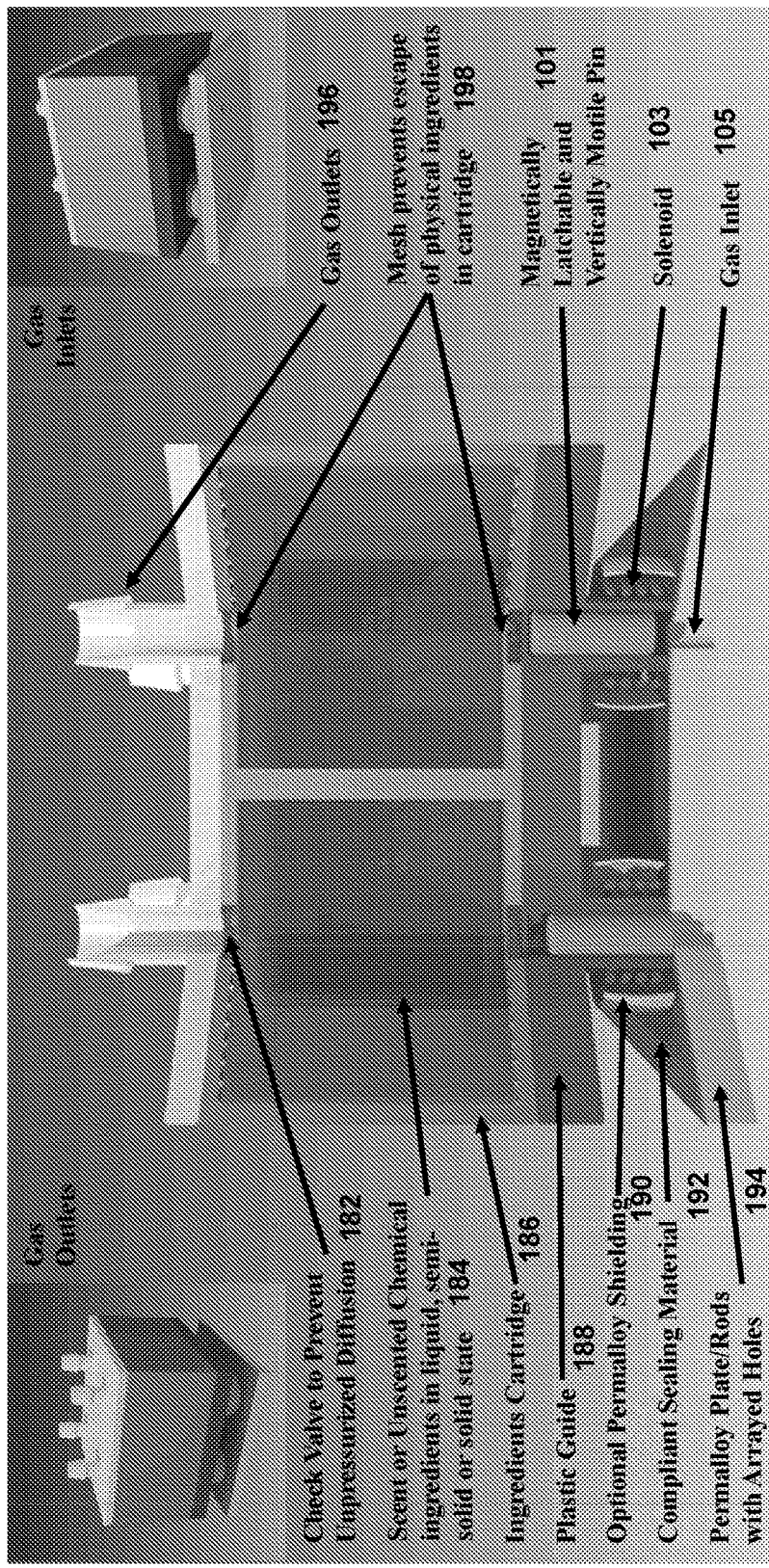

FIG. 1 (K) – Two-dimensional Array of Remanent Magnetization Valves for Scent or Unscented Fluid Release: An example 2x2 array containing four scents which may be controllably released as shown in the above cutaway view. In the closed state, magnetized latchable pins snap against Permalloy plate (with size-matching hole or rod) to compress a compliant seal. To open, a selected pin is demagnetized and gas pressure through the plate aids in separation. Carbon or other gas purification filters at the inlet prevent contamination of the scent. Cylindrical pins are held in place by non-circular (square, triangular, or other) pin guides permitting gas flow around the pin edges when pin is pushed back from seal against Permalloy. For scent release, gas flow is pushed through an optionally removable/replaceable scent cartridge located adjacent to the remanent magnetization switch array and then scented gas delivered through check valves to the scent outlets. Valves positioned in the array (e.g., 10 x 10 or 8 x 20, etc.) can be programmably and selectively actuated (only one or more for combination scents) by wireless signals (such as Wi-Fi) or hard wired signals with compatible software, so that a particular device is magnetized/demagnetized and gas flow initiated/stopped.

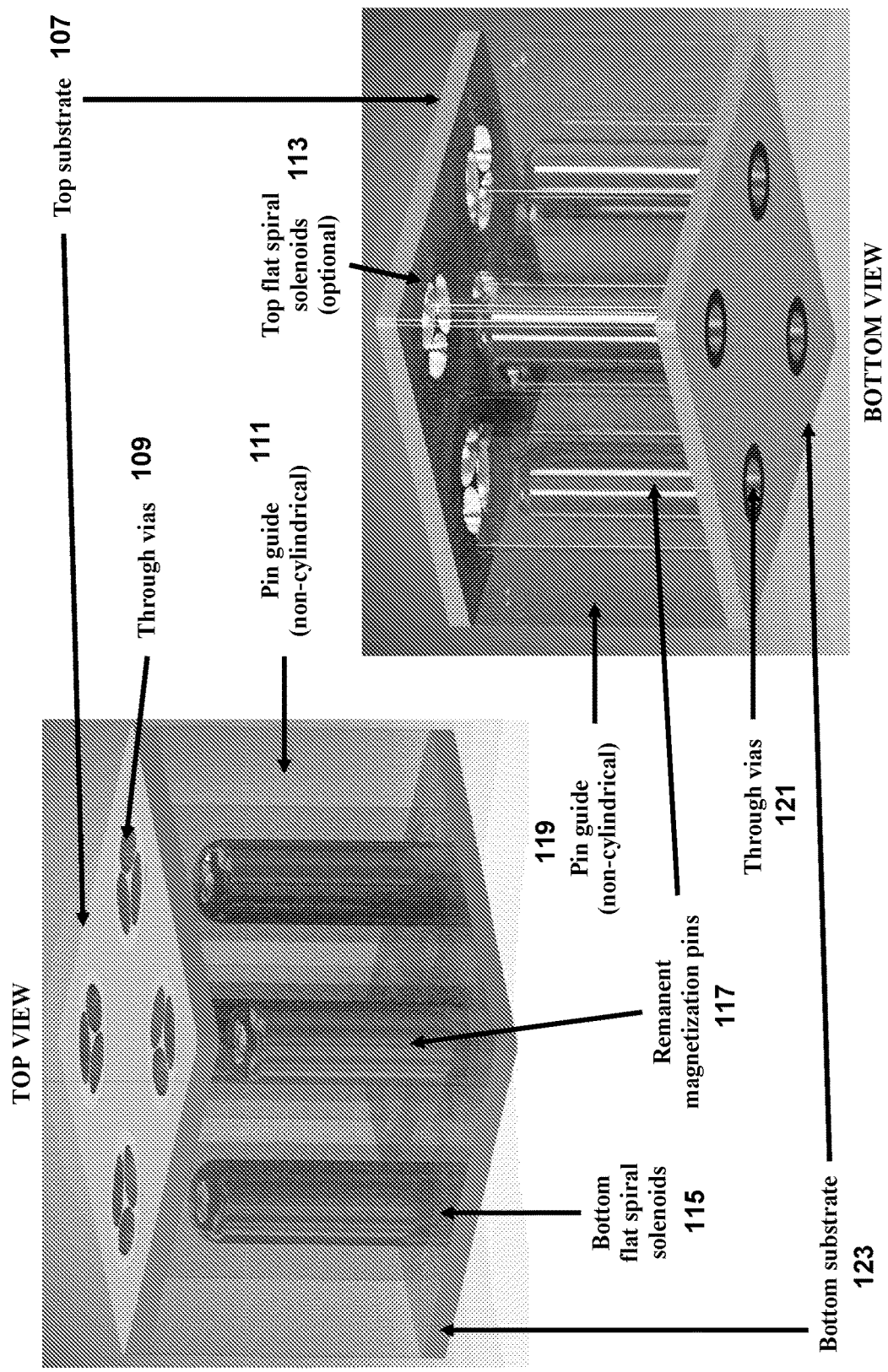
FIG. 1 (L) – Remanent Magnetization Valves with Two-dimensional Solenoids: For convenient miniaturization and production by standard lithographic process, flat spiral solenoids on substrates at the top and bottom of the non-cylindrical pin-guide may be used for magnetization and demagnetization. With this design, many valves could be produced in parallel.

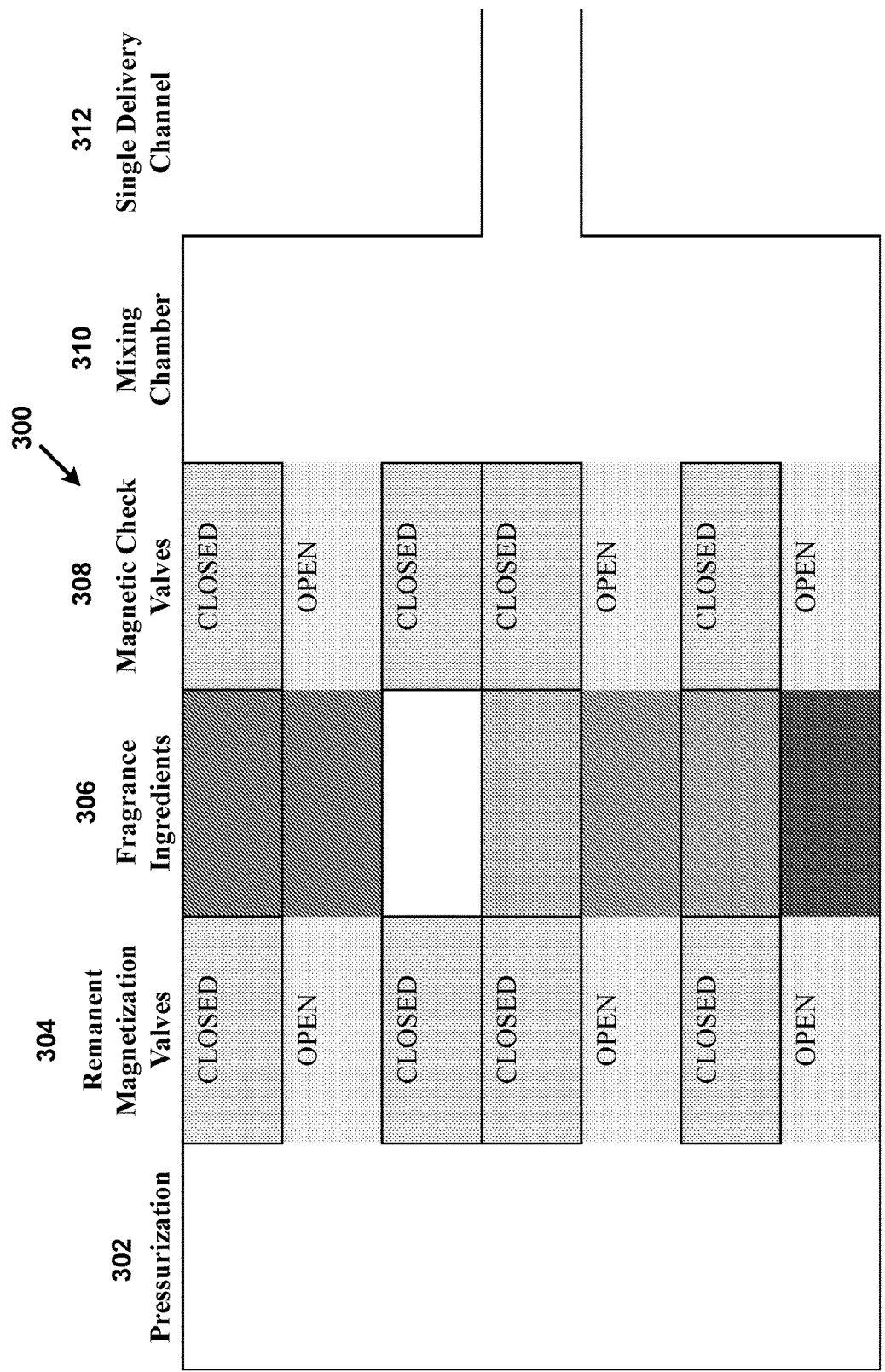
FIG. 3 (A) – Fragrance Ingredient Blending via Activation of Multiple Remanent Magnetization Valves Simultaneously: Scented or unscented fluids may be combinatorially compounded by activating multiple valves simultaneously or in timed duty cycling, passing fluid through cartridge chambers, and then mixing after selection.

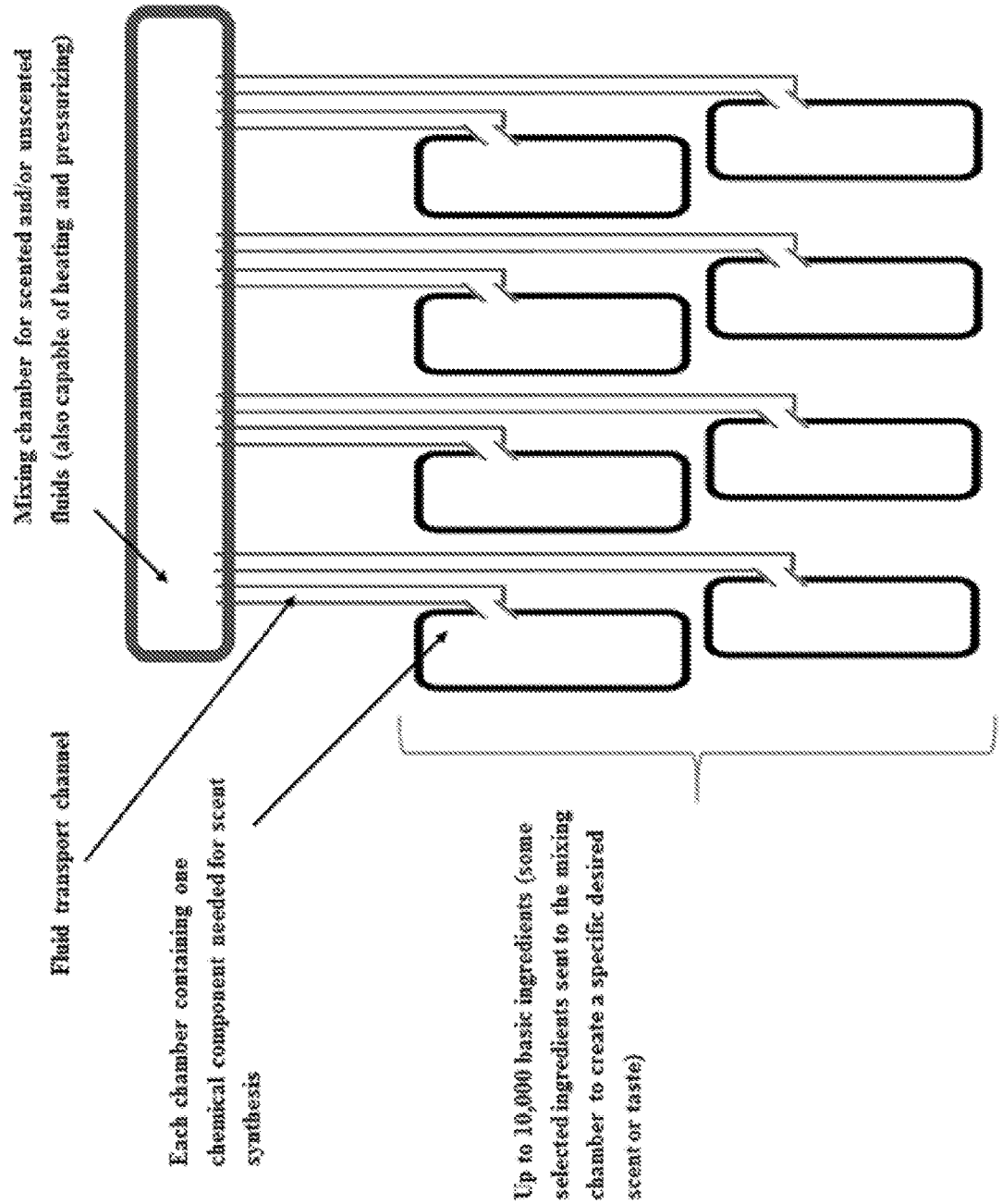
FIG. 3 (B) – Remotely Located Ingredients: Fluids are transported via transport channel to a mixing chamber for compounding.

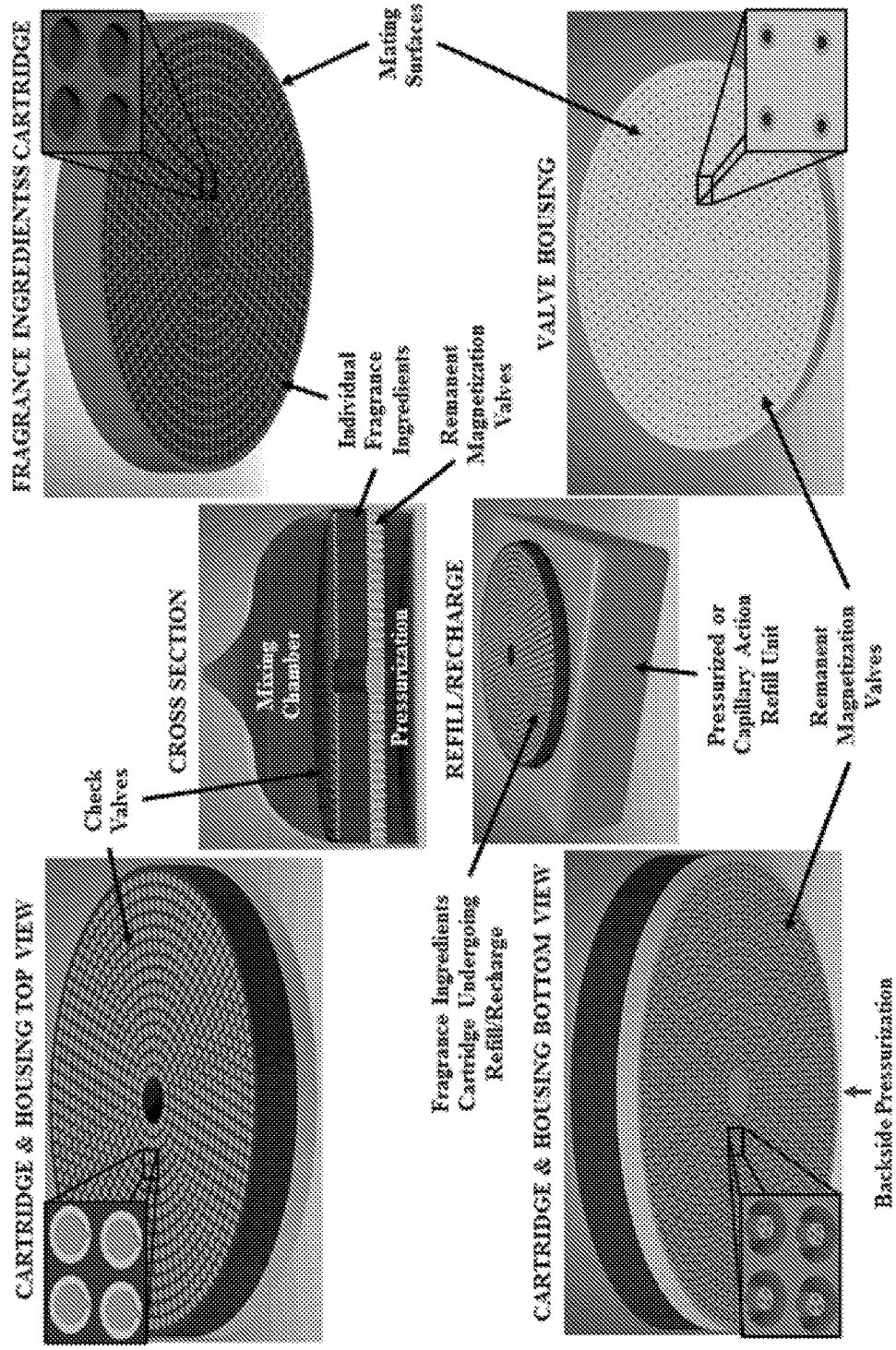

FIG. 3 (C) – Flat Flavor/Fragrance ("Scent") and/or Other Ingredient Container Layout for Rapid Ingredient Mixing: A disk shaped or other two-dimensionally shaped cartridge comprising up to 1000s of individual fragrance ingredients mates with an array of remanent magnetization valves. Multiple selections simultaneously permit combinatorial mixing of ingredients. Containers are selected by valve activation. Ingredients may be replenished by inserting cartridge into a refill or recharge unit utilizing capillary action or pressurized refill.

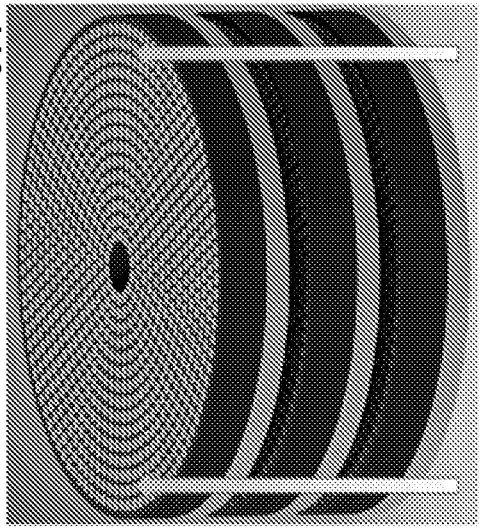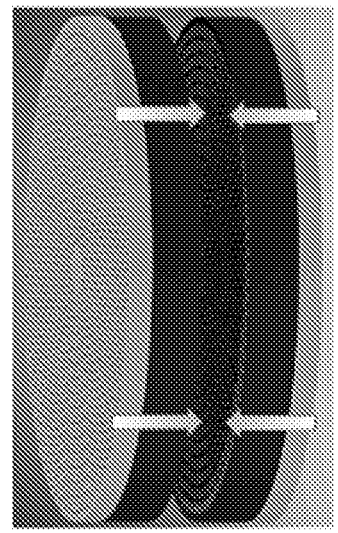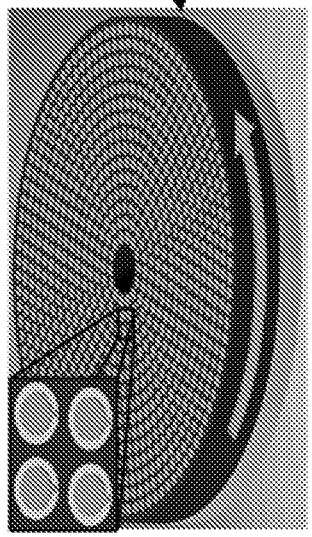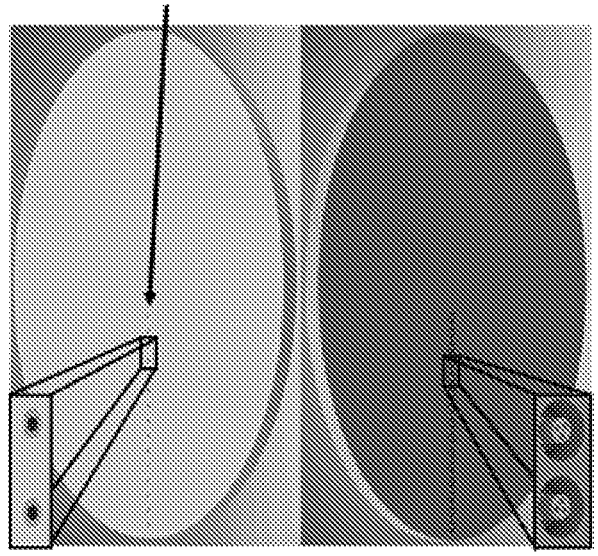
FIG. 3D

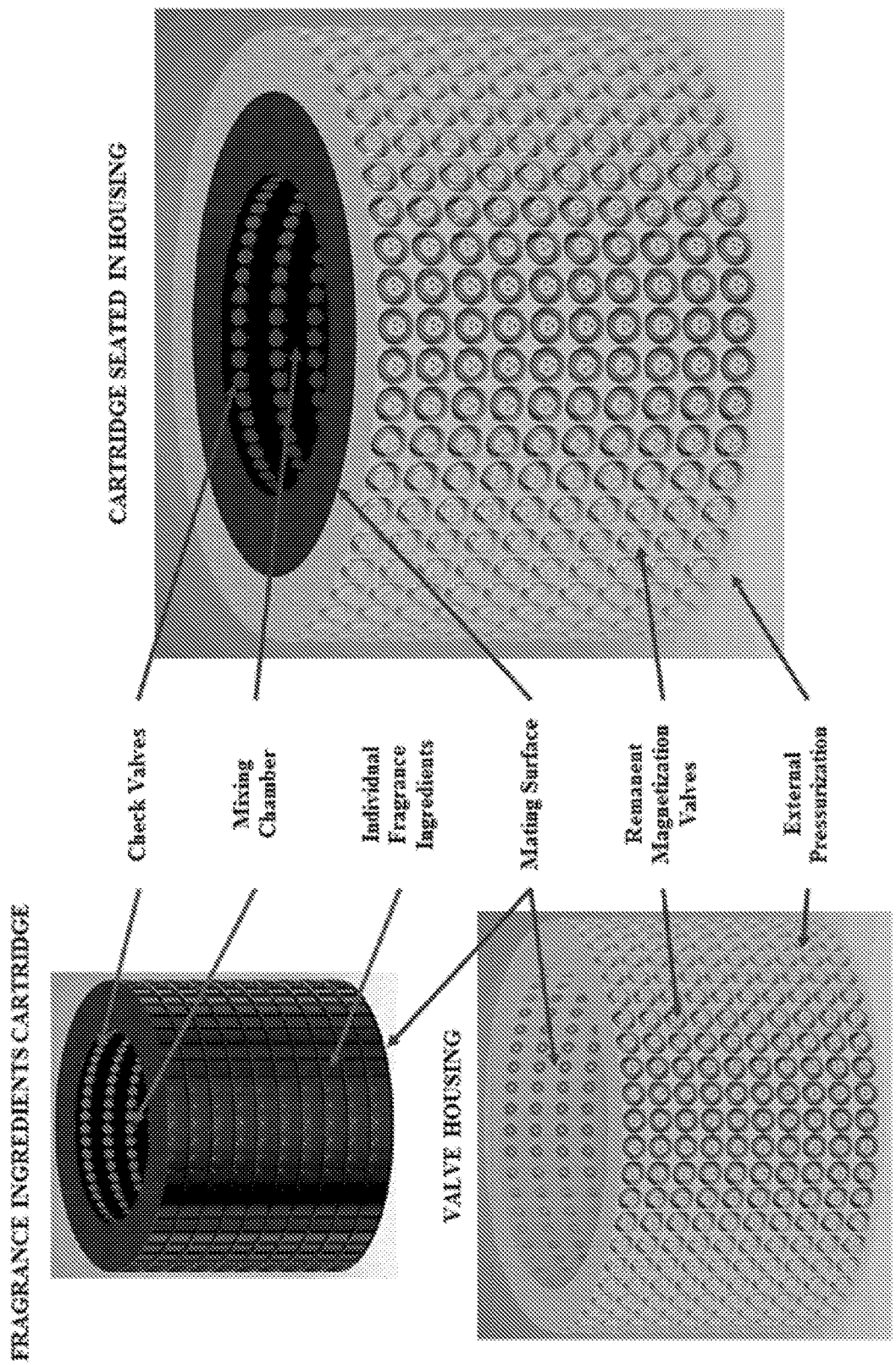

FIG. 3 (E) – Ring-type Scent or Other Ingredient Container Layout for Rapid Ingredient Mixing: A cylindrical cartridge comprising up to 1000s of individual fragrance or flavor or other ingredients mates with an array of remanent magnetization valves. Containers are selected by valve activation. Multiple selections simultaneously permit combinatorial mixing of ingredients.

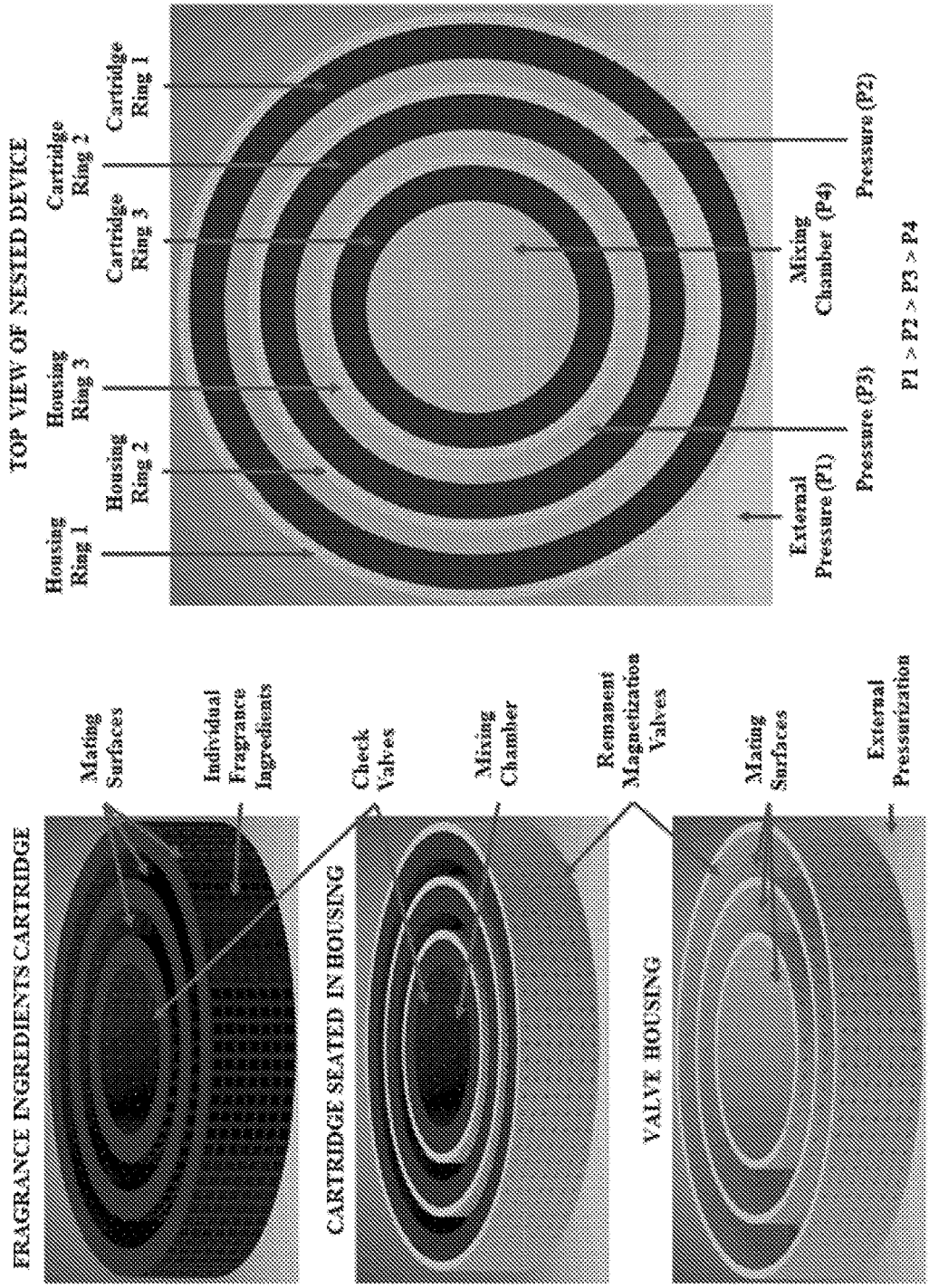

FIG. 3 (F) – Nested Ring-type Fragrance and Fragrance or Other Ingredient Container Layout for Rapid Ingredient Mixing: A cylindrical cartridge comprising multiple rings of individual flavors or fragrances. Multiple simultaneous selections permit combinatorial mixing of ingredients. Similar to the disk-type structure of FIG. 3 (D), ringed valve arrays may be rotated to minimize the number of valves in use if desired.

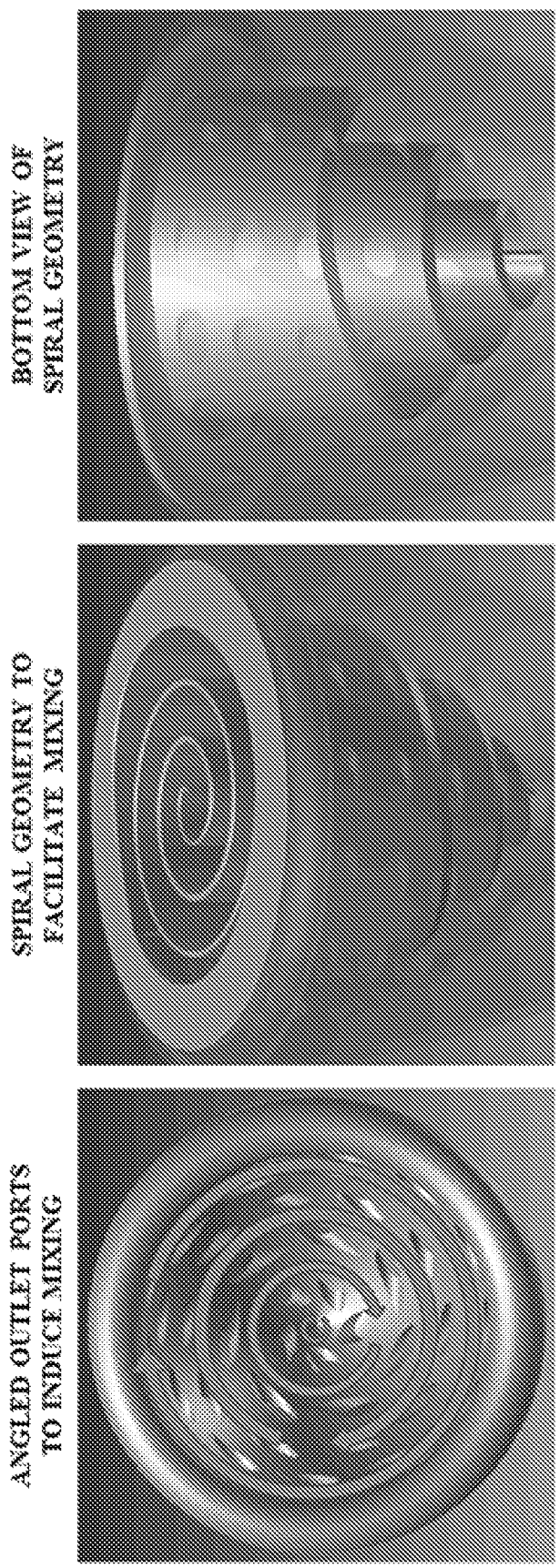
FIG. 3 (G) – Assisted Ingredient Mixing via Geometry or Agitation: Flavor and fragrance or other ingredient mixing may be accomplished via direct agitation or geometrically induced mixing.

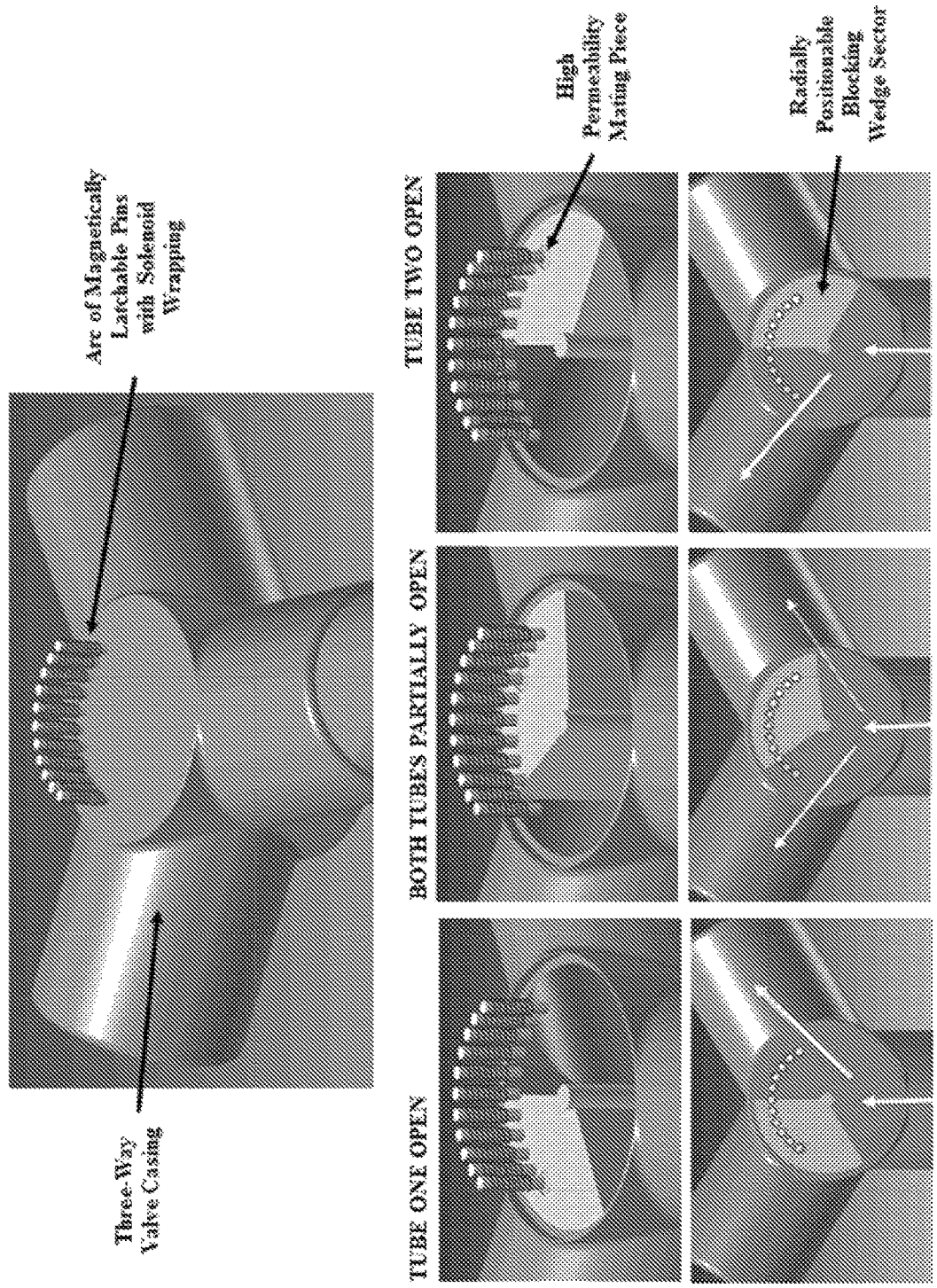
FIG. 3 (H) – Latchable Remanent Magnetization Mixing/Dividing Valve: An arc of magnetically latchable pins controls an internal blocking wedge as shown in the lower cutaway views with top-casing removed to show the interior components.

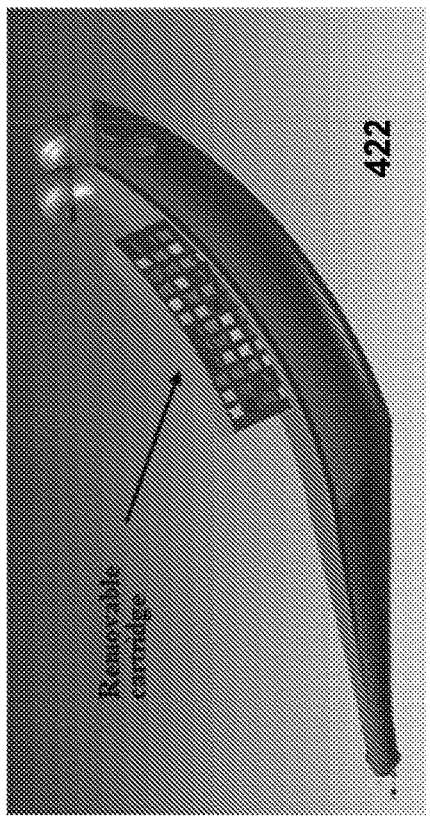
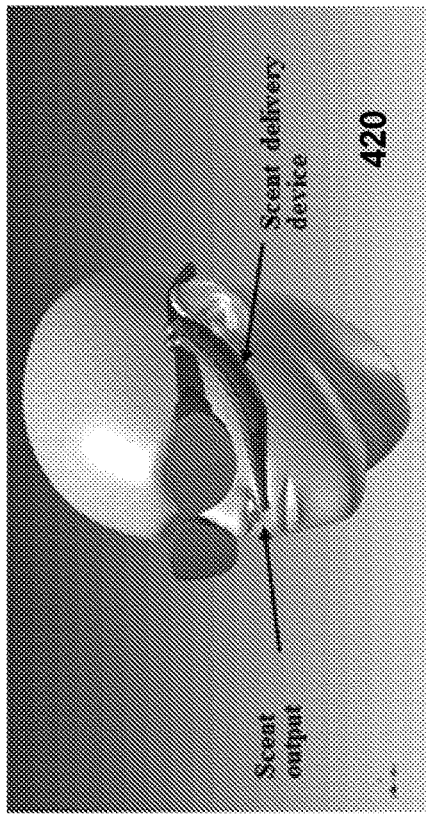
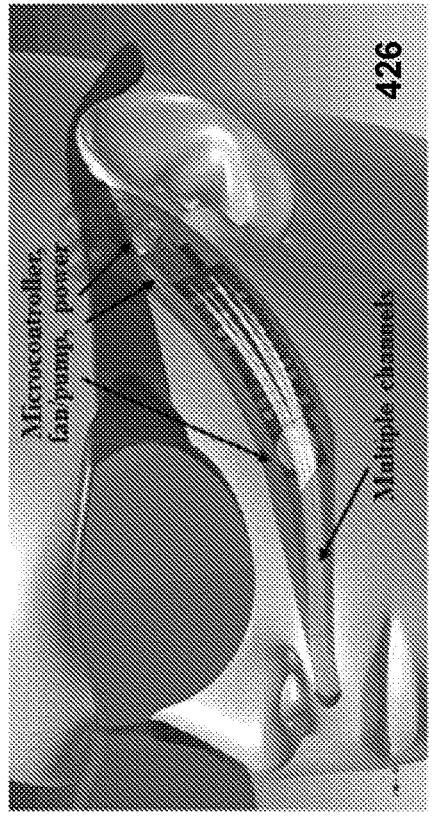
FIG. 4 (E) – Scent Delivery with Midline Cartridge Location for VR or AR Headgear: Scented gas is created by directing gas flow through a removable/replaceable scent cartridge with open scent container selected by remanent magnetization switch and into its dedicated tube or channel leading to a scent diffuser near the user's nostrils.

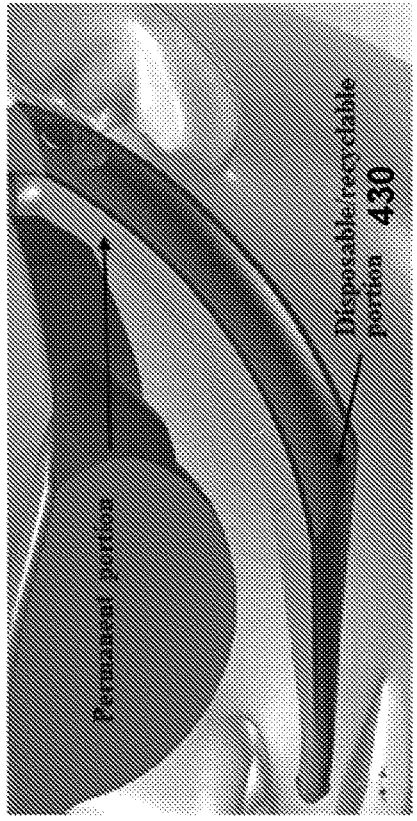
Fully disposable/recyclable self-contained scent delivery may also be used with VR or AR headgear.

Fully disposable scent delivery device 428

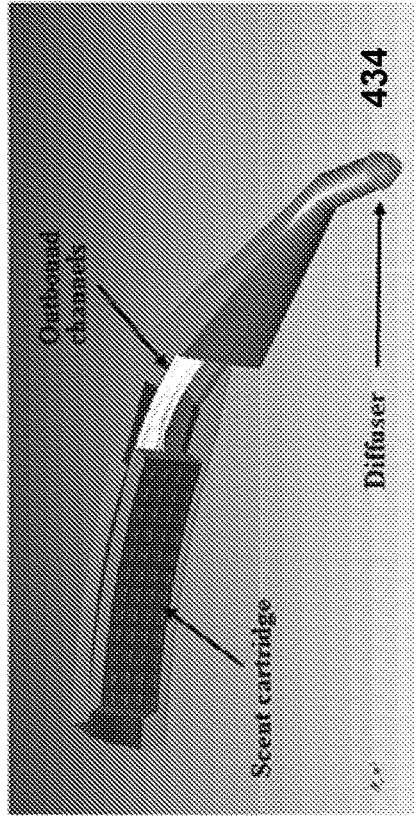
Partially disposable scent delivery device with replaceable portion slotting into permanent portion.

Disposable/recyclable portion 430

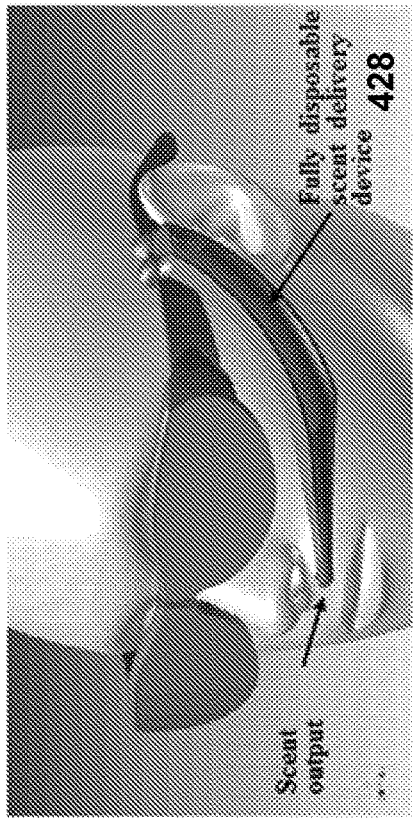
The permanent portion of the scent delivery device containing battery, fan, microelectronics, and switches.

Microcontroller & Fan 432
Switches
Battery

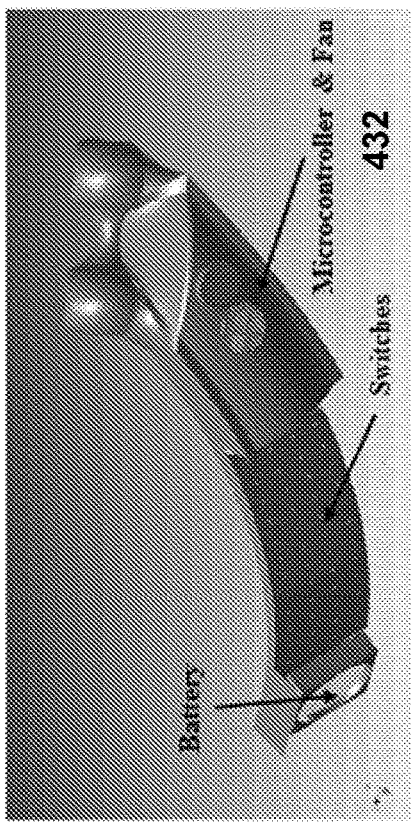
Disposable/recyclable portion containing cartridge, outbound channels, and diffuser to be slotted into permanent portion.

434
Scent cartridge
Diffuser

FIG. 4 (F) – Fully or Partially Disposable Scent Delivery Unit for VR or AR Devices: Scent release is accomplished by pushing gas flow through the disposable/recyclable cartridge, outbound channels, and diffuser near the nostrils. Scent is selected by remanent magnetization switches in the permanent portion comprised of fan, battery, microelectronics, and switches.

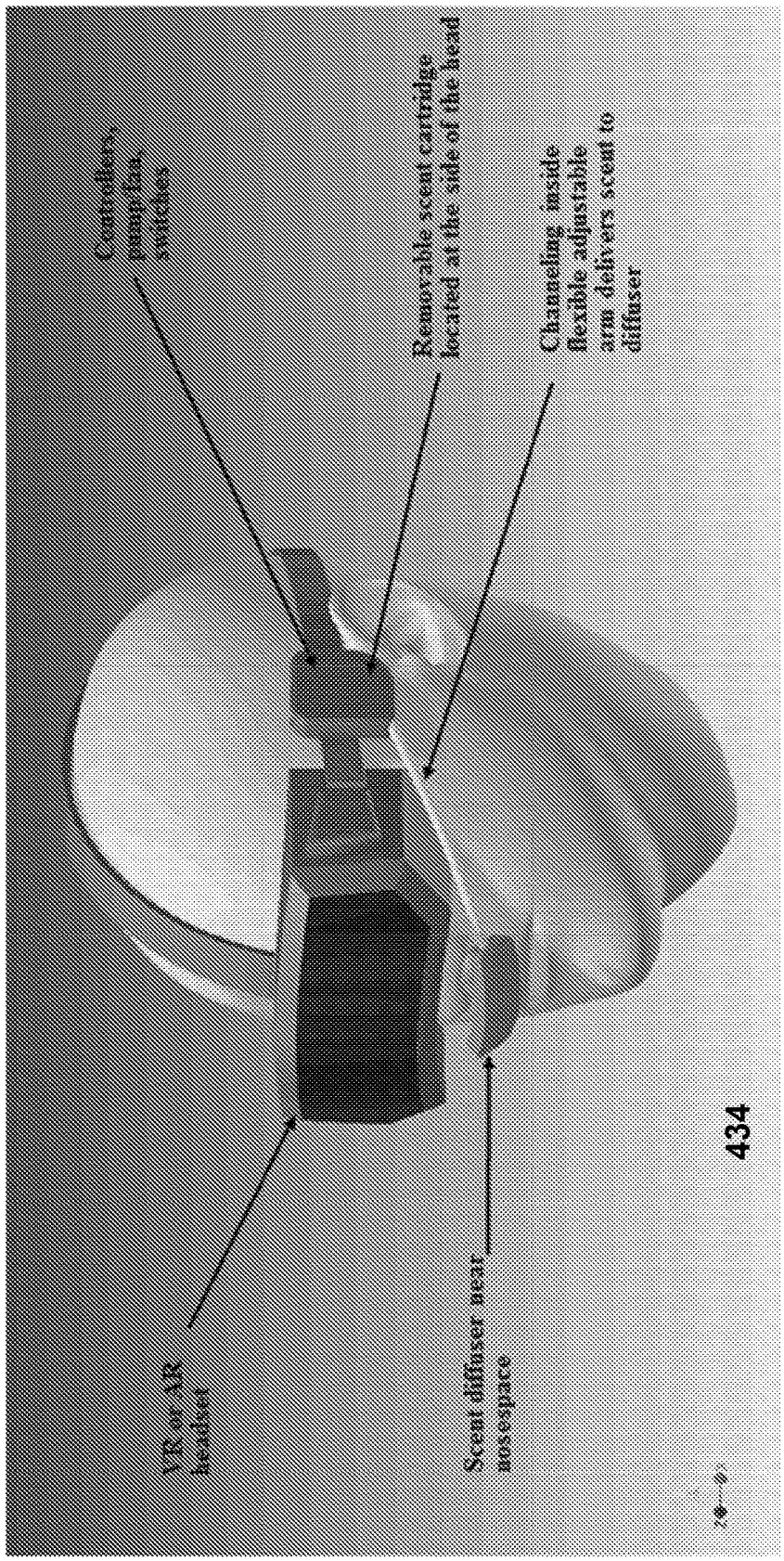

FIG. 4 (G) – Side-mounted Scent Delivery Device: Self-contained controllable scent delivery device with side-mounted replaceable/refillable cartridge attached to VR or AR headgear, or worn separately attached to the head via strap(s). Scent release is accomplished by pushing gas flow through a removable/replaceable scent cartridge located at the side of the head with an open scent container selected by remanent magnetization switch and then scented gas delivered through separate channelling to a scent diffuser near the user's nostrils. All scent release from headset, eyewear, or other configuration devices can be programmably actuated by wireless signals (such as Wi-Fi) or hard wired signals. The control software can be either stored in the hardware components or can be utilized through wireless signals. A symmetrical cartridge could also be positioned on the opposite side of the head with delivery arm leading into the same diffuser.

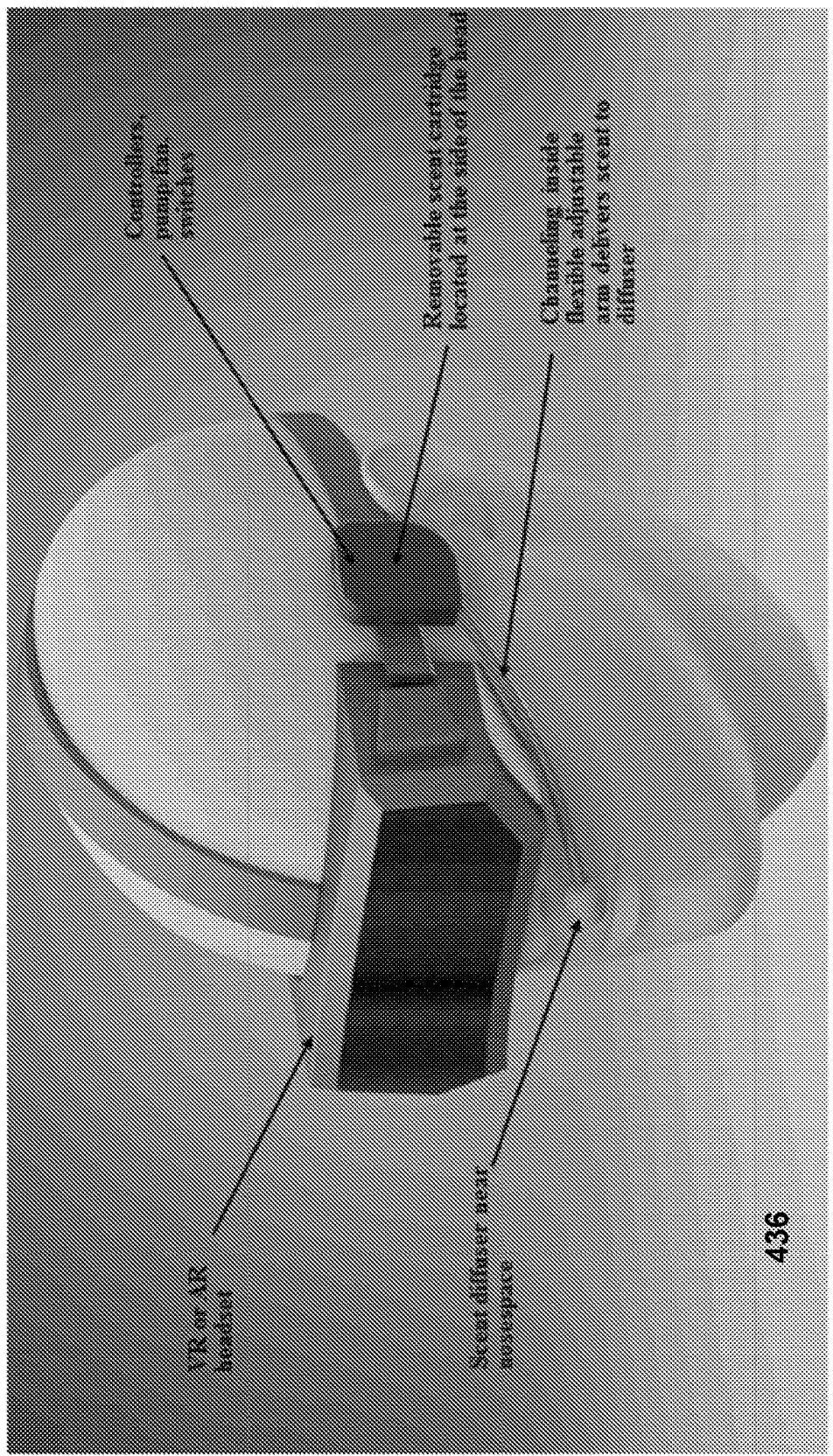

FIG. 4 (H) – Side-mounted Scent Delivery Device with Small Diffuser: Self-contained controllable scent delivery device with side-mounted replaceable/refillable cartridge attached to VR or AR headgear, or worn separately attached to the head via strap(s). Scent release is accomplished by pushing gas flow through a removable/replaceable scent cartridge located at the side of the head with an open scent container selected by remanent magnetization switch and then scented gas delivered through separate channelling to a scent diffuser near the user's nostrils. All scent release from headset or other configuration devices can be programmably actuated by wireless signals (such as Wi-Fi) or hard wired signals. The control software can be either stored in the hardware components or can be utilized through wireless signals.

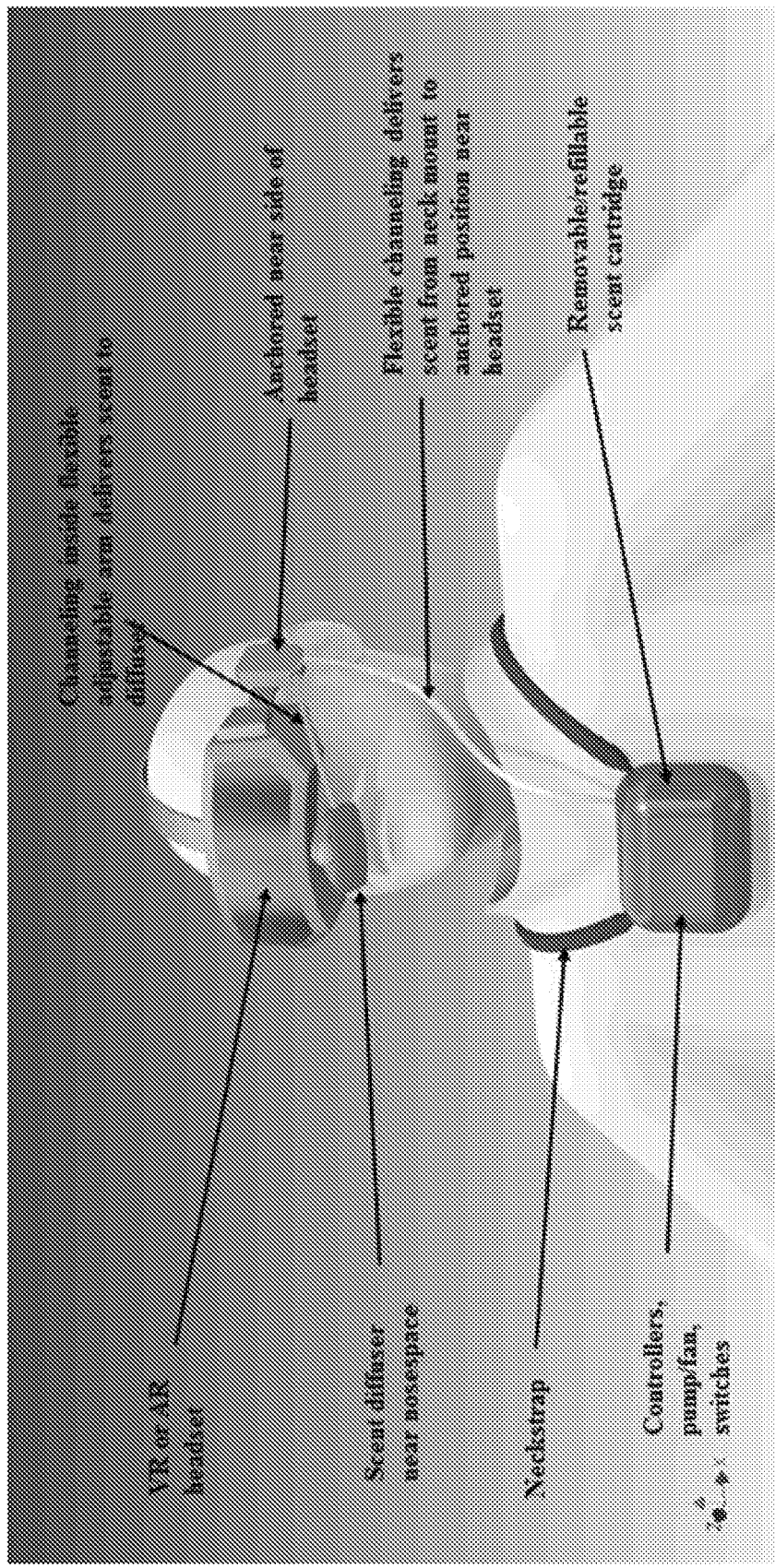

FIG. 4 (I) – Neckworn Scent Device Configuration: Self-contained controllable scent delivery from a neck-mounted replaceable/refillable cartridge. Side mounted scent cartridge and delivery arm with diffuser may be attached to VR or AR device or worn separately. Scent release is accomplished by pushing gas flow through a removable/replaceable scent cartridge suspended from the user's neck up through scent-specific channeling to an anchored position at the side of the head and then to a scent diffuser near the user's nostrils. Control mechanisms and fan/pump are located with the suspended cartridge. As an alternative, a larger scent container could be rear mounted as a backpack to allow for a greater number or longer-lasting amount of scents.

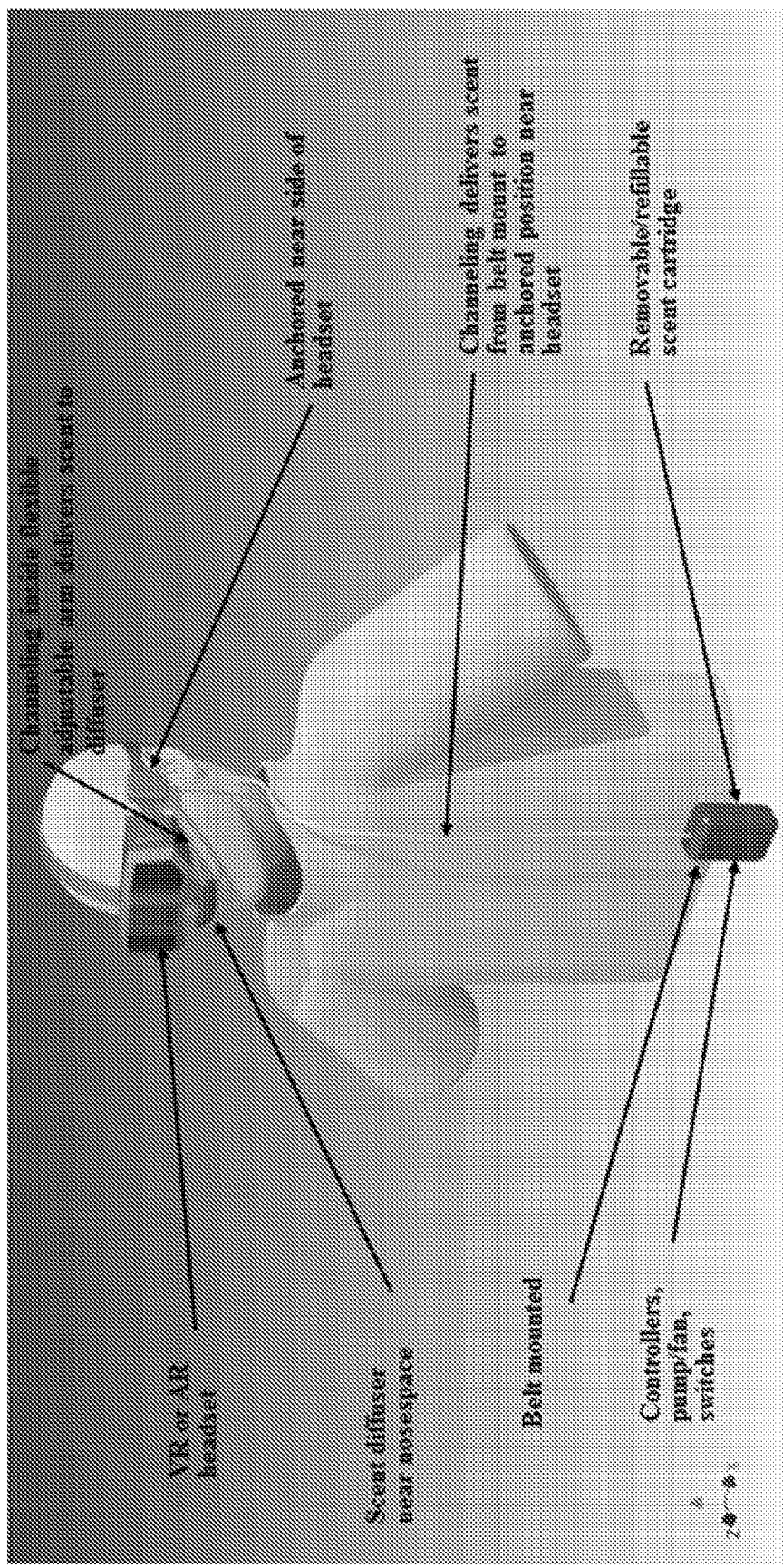

FIG. 4 (J) – Belt-mounted Scent Device: Self-contained controllable scent delivery from a belt-mounted replaceable/refillable cartridge. Configuration can be worn and used with or without VR or AR headset. Scent release is accomplished by pushing gas flow through a removable/replaceable scent cartridge suspended from the user's belt up through scent-specific channeling to an anchored position at the side of the head, or alternatively routed to it, and then to a scent diffuser near the user's nostrils. Control mechanisms and fan/pump are located with the suspended cartridge.

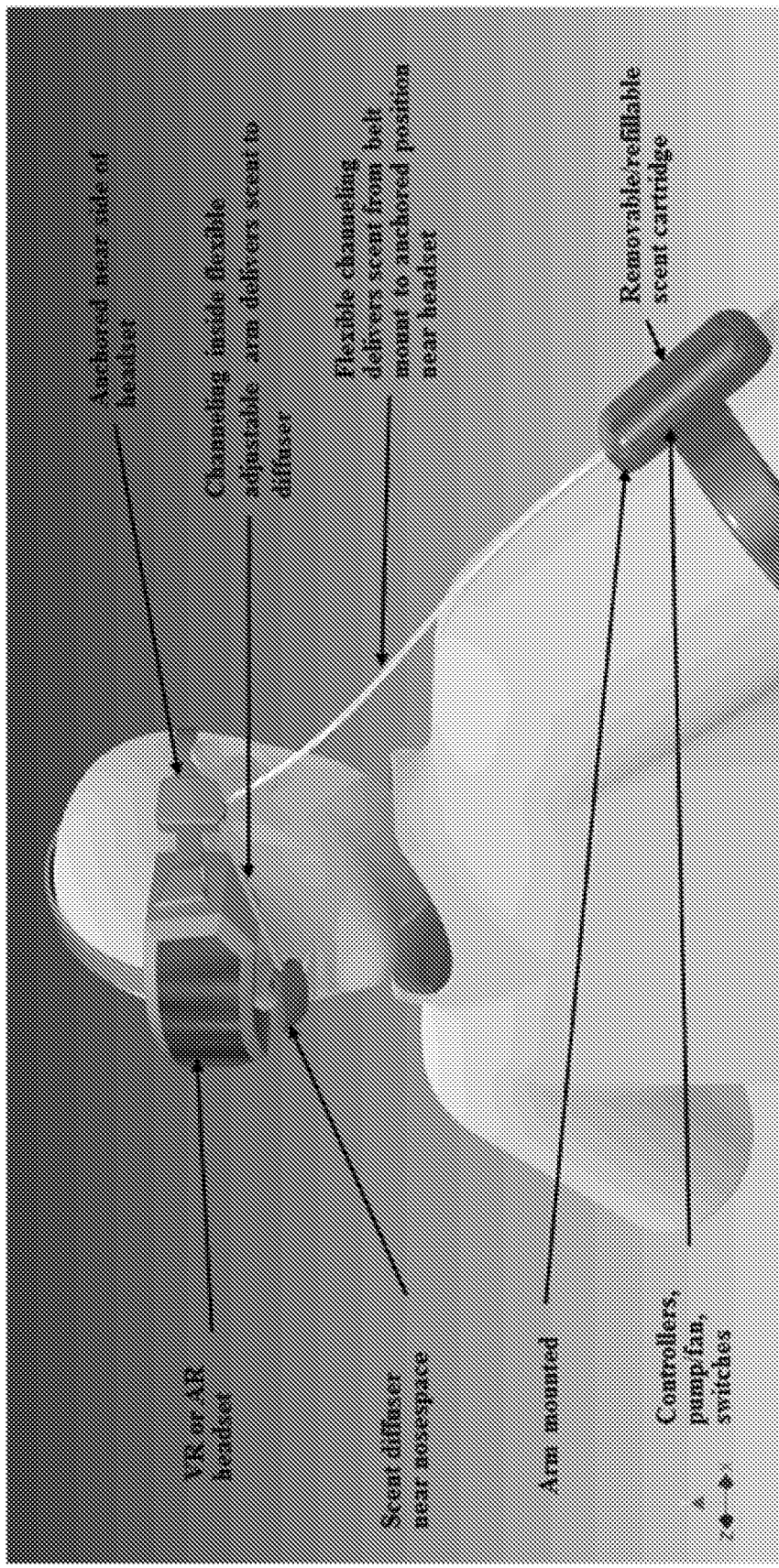

FIG. 4 (K) – Arm-mounted Scent Device: Self-contained controllable scent delivery from an arm-mounted replaceable/refillable cartridge. Device can be configured for use with or without VR or AR devices. Scent release is accomplished by pushing gas flow through a removable/replaceable scent cartridge suspended from the user's arm up through scent-specific channelling to an anchored position at the side of the head and then to a scent diffuser near the user's nostrils. Control mechanisms and fan/pump are located with the suspended cartridge.

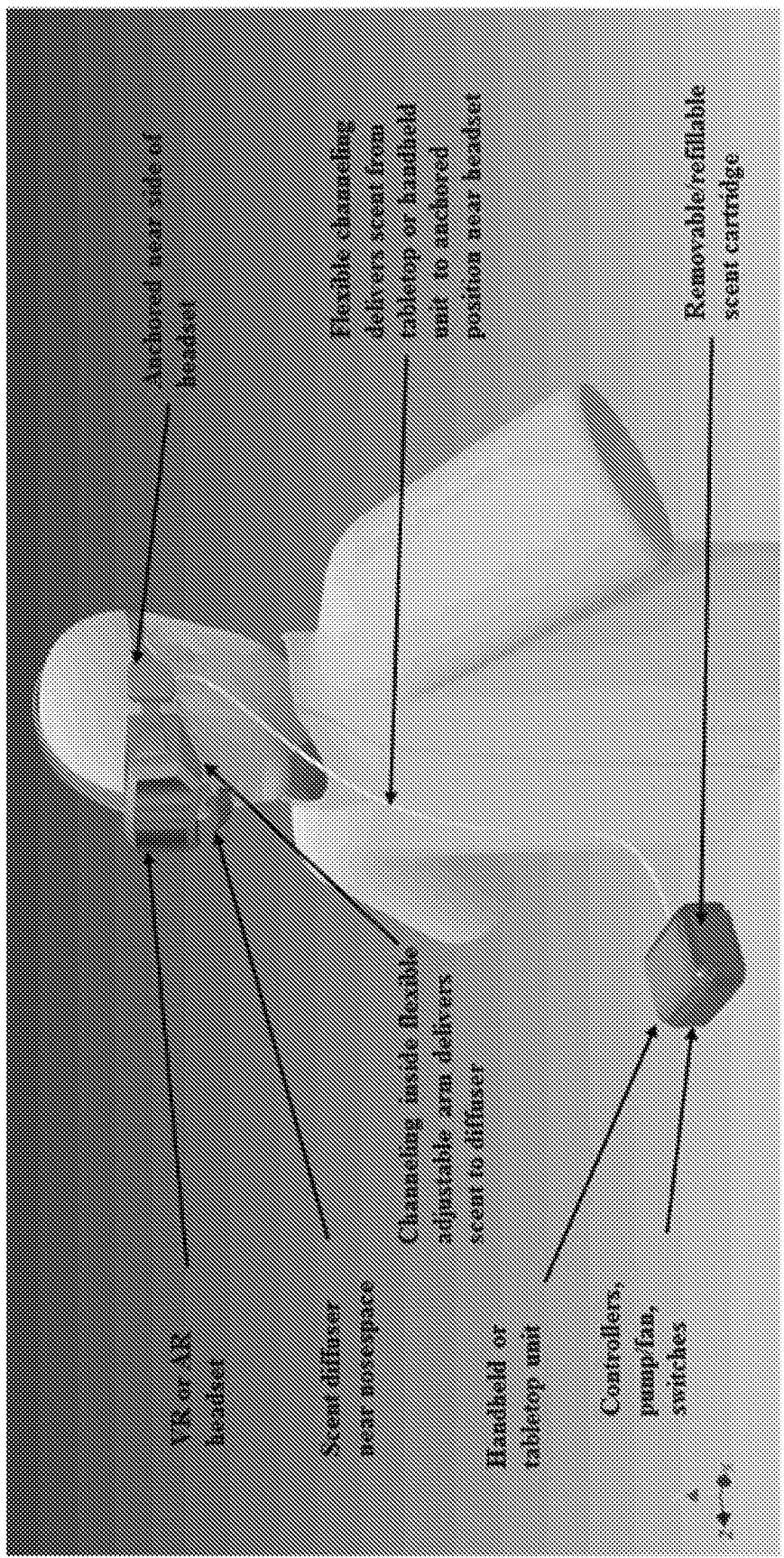

FIG. 4 (L) – Portable Tabletop Scent Devices: Self-contained controllable scent delivery from a tabletop replaceable/refillable cartridge. Device can be configured for use with or without VR or AR headset. Scent release is accomplished by pushing gas flow through a removable/replaceable scent cartridge in a tabletop or handheld unit up through scent-specific channeling to an anchored position at the side of the head and then to a scent diffuser near the user's nostrils. Control mechanisms and fan/pump are located with the scent cartridge.

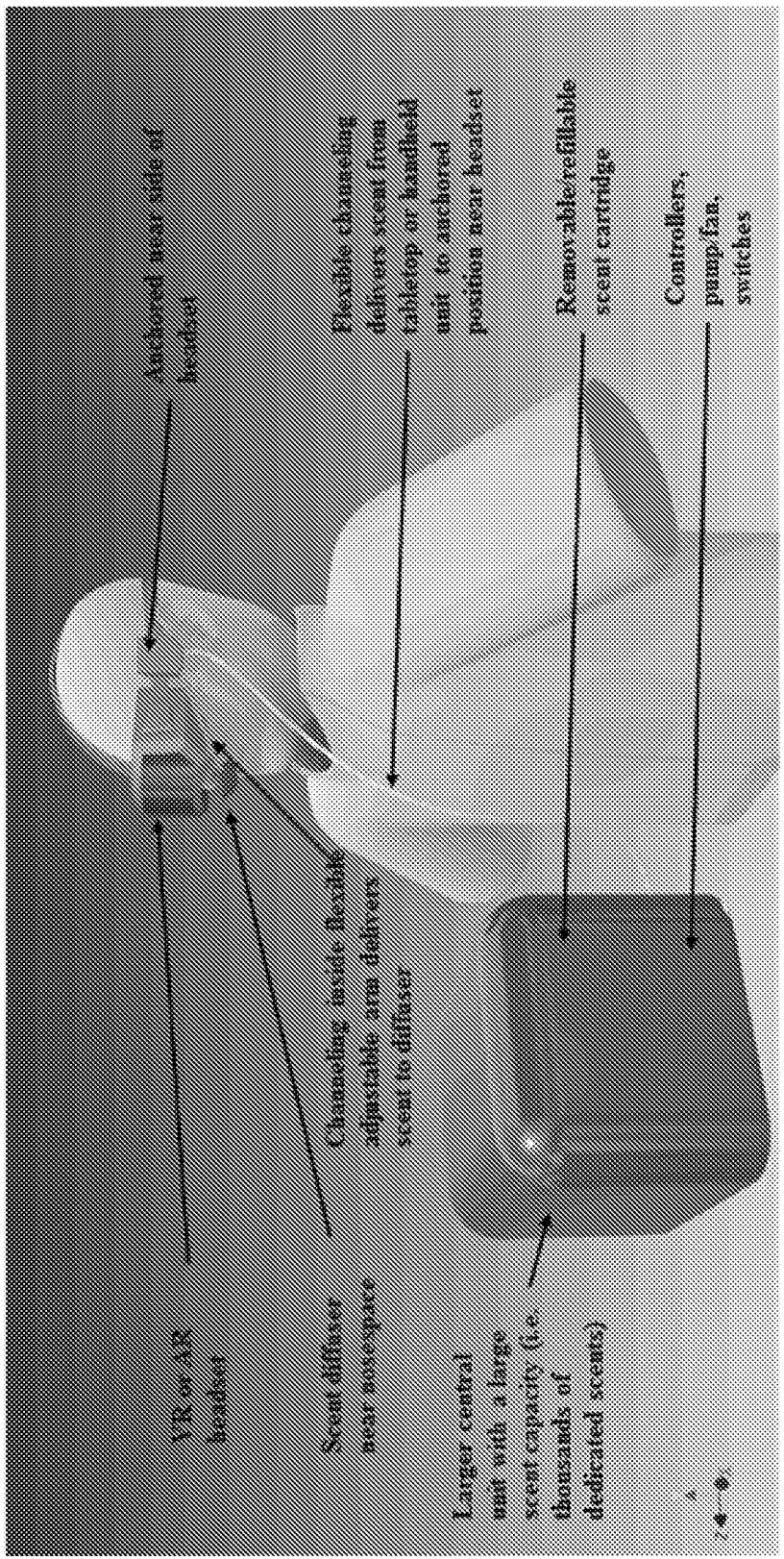

FIG. 4 (M) – High Capacity Scent Device: Self-contained controllable scent delivery from a large central unit with a large scent capacity (i.e. thousands of dedicated scents). Device can be configured for use with or without VR or AR headset (e.g. for normal viewing of televisions or desktop computer monitors). Scent release is accomplished by pushing gas flow through a scent cartridge in the large central unit up through scent-specific channeling to an anchored position at the side of the head and then to a scent diffuser near the user's nostrils. Control mechanisms and fan/pump are located in the large central unit with a large capacity of dedicated scents.

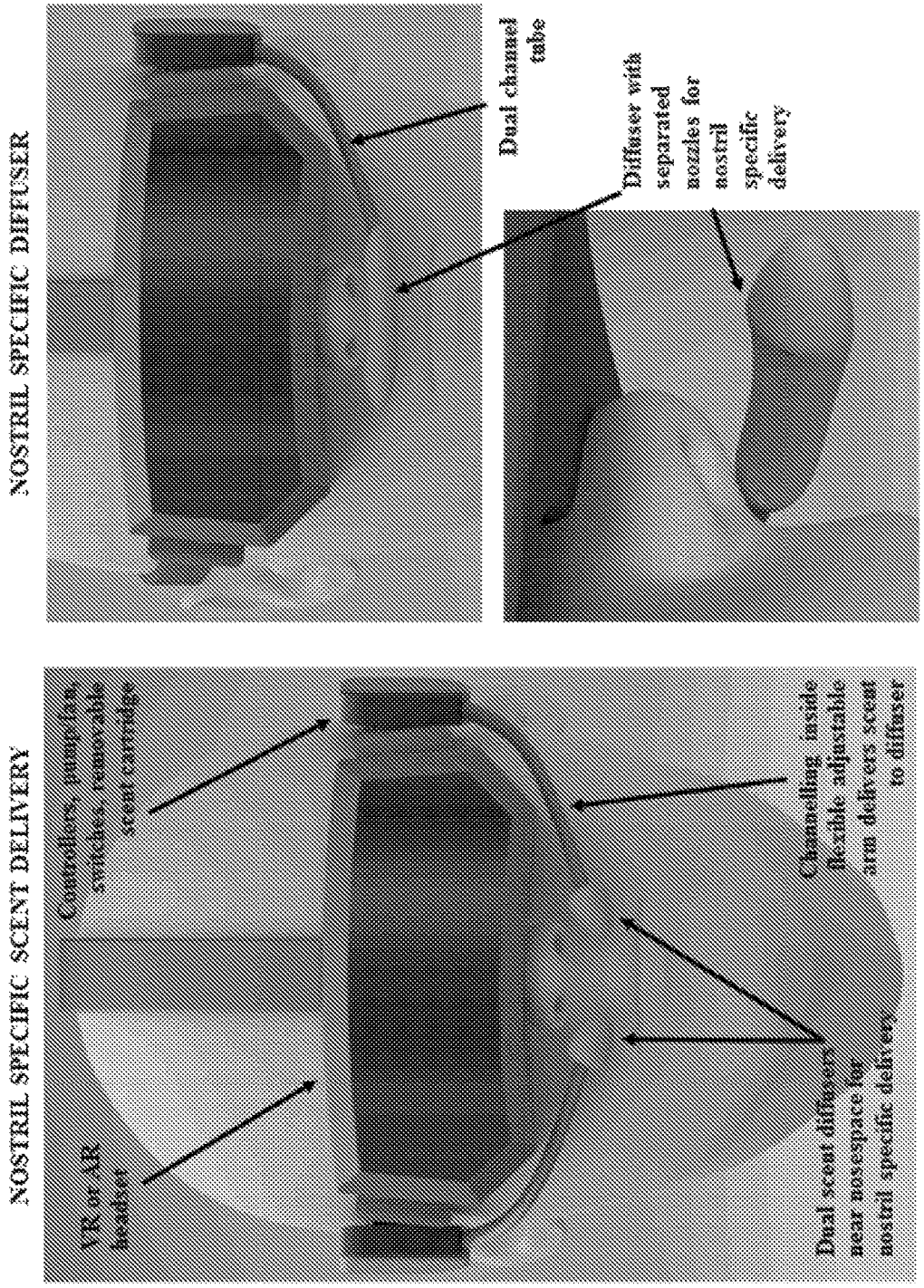

FIG. 4 (N) – Three-dimensional Scent Delivery with Dual or Triple Scent Diffuser Outputs: For directional scents, employing dual or triple scent streams with varying scent compositions and concentrations allows for precise control of scent (location of origin and other) perception. Delivery into the nosespace may be via fully separated channelling, or a combined or bundled channel with separated outputs.

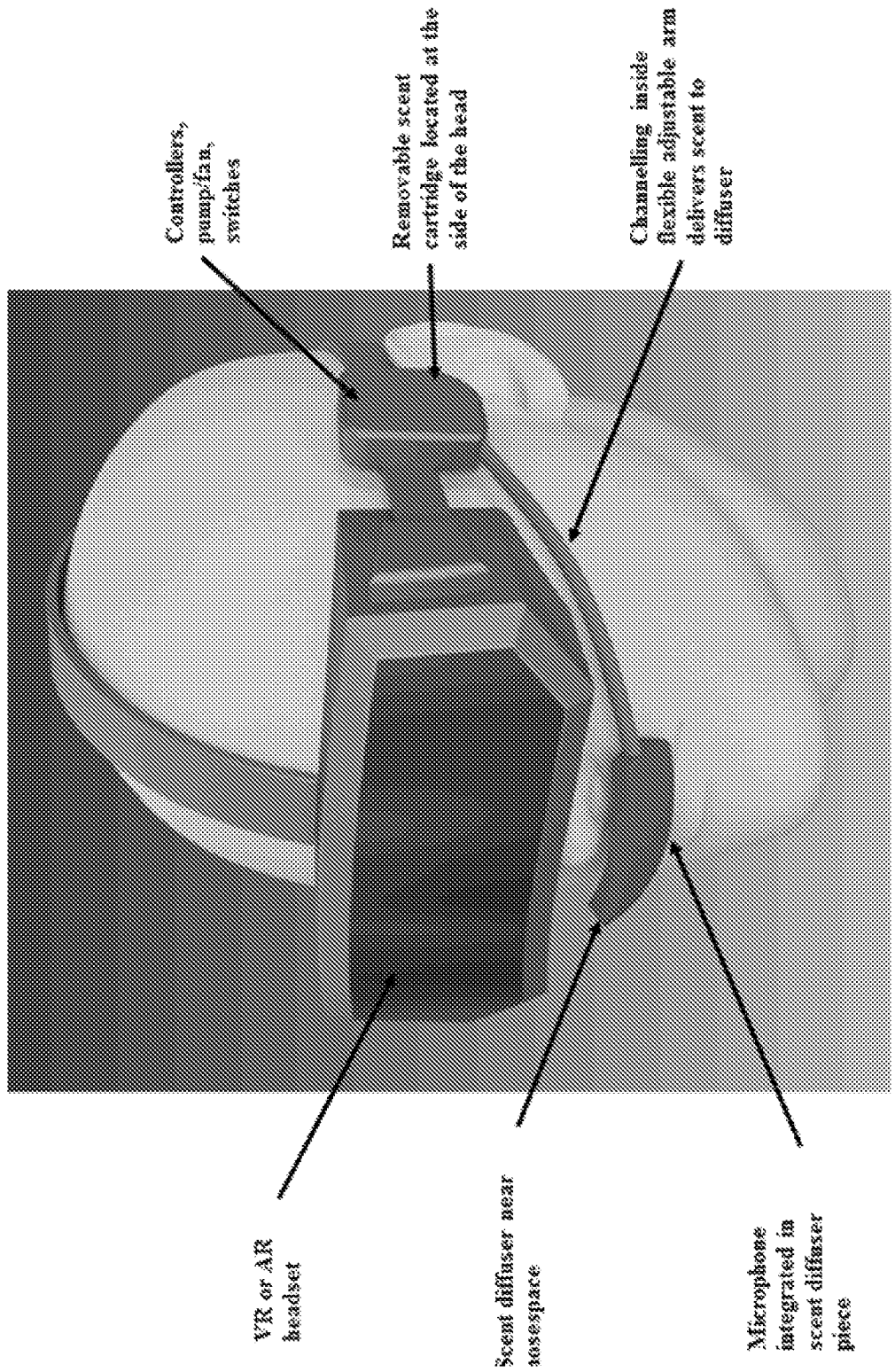
FIG. 4 (O) – Scent Delivery Armature with Integrated Microphone: Inclusion of a microphone into or adjacent to the diffuser of a scent delivery headset provides for combined audio and scent functionality.

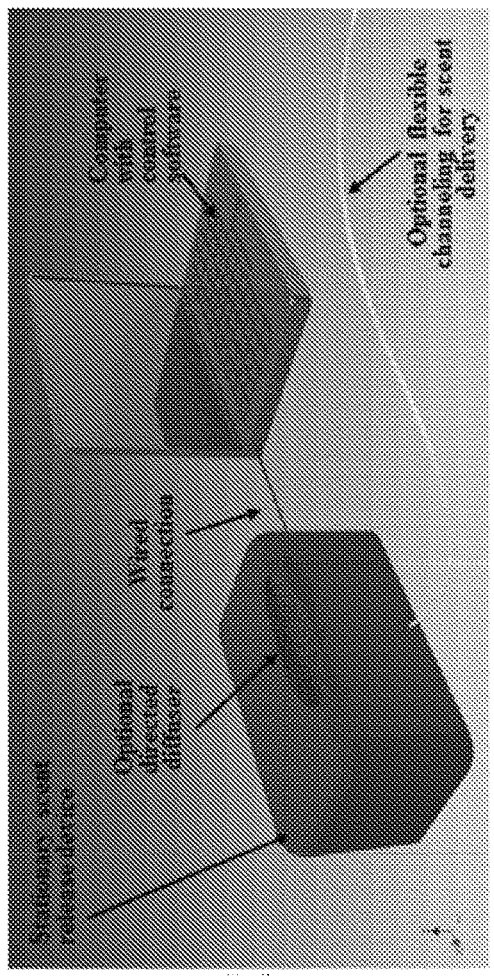

FIG. 4 (P) – Wired Stationary Configuration for Scent Delivery: Signals from an adjacent computer are carried to scent release device by wire connection initiating scent release on command. Computer or release device contains control software that programmably releases the desired scent(s). Release may be directed by adjustable exit port or diffuser to a targeted space. Wired connections for scent release can be extended to various other applications beyond desktop applications, for example, brick and mortar and point of sale shopping experiences, live entertainment, teleconferencing, etc..

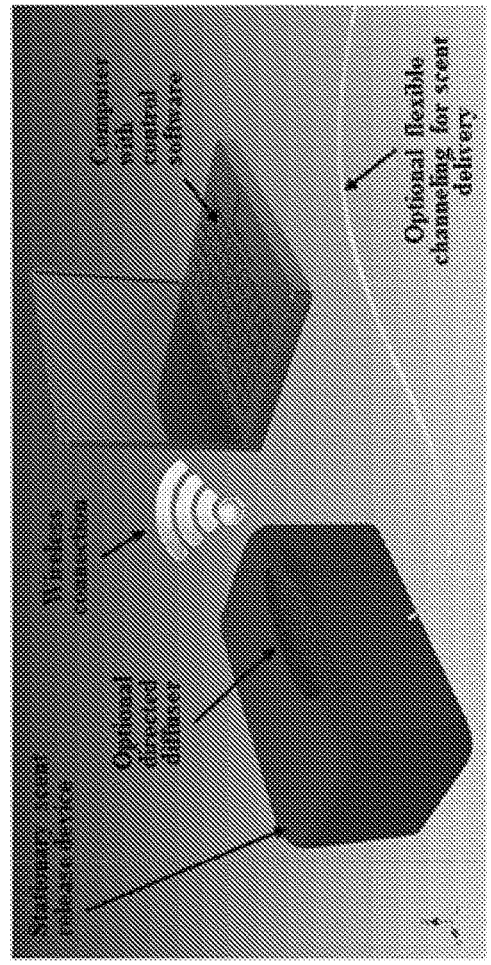

FIG. 4 (Q) – Wireless Stationary Configuration for Scent Delivery: Wireless signals from a nearby computer, or transmitting sensors such as beacons are communicated to scent release device to initiate scent release on command. Computer or release device contains control software that is an integral part of the invented device, and is programmed to selectively release the desired scent(s) in certain fashion. Release may be by directed by adjustable exit port or diffuser to a targeted space. Wireless connections for scent release include desktop use as well as such applications as brick and mortar in-store display or point of sale or product shopping, teleconferencing, etc.. Device can also be miniaturized for wearable applications such as device worn around the neck and angled towards user's nose space.

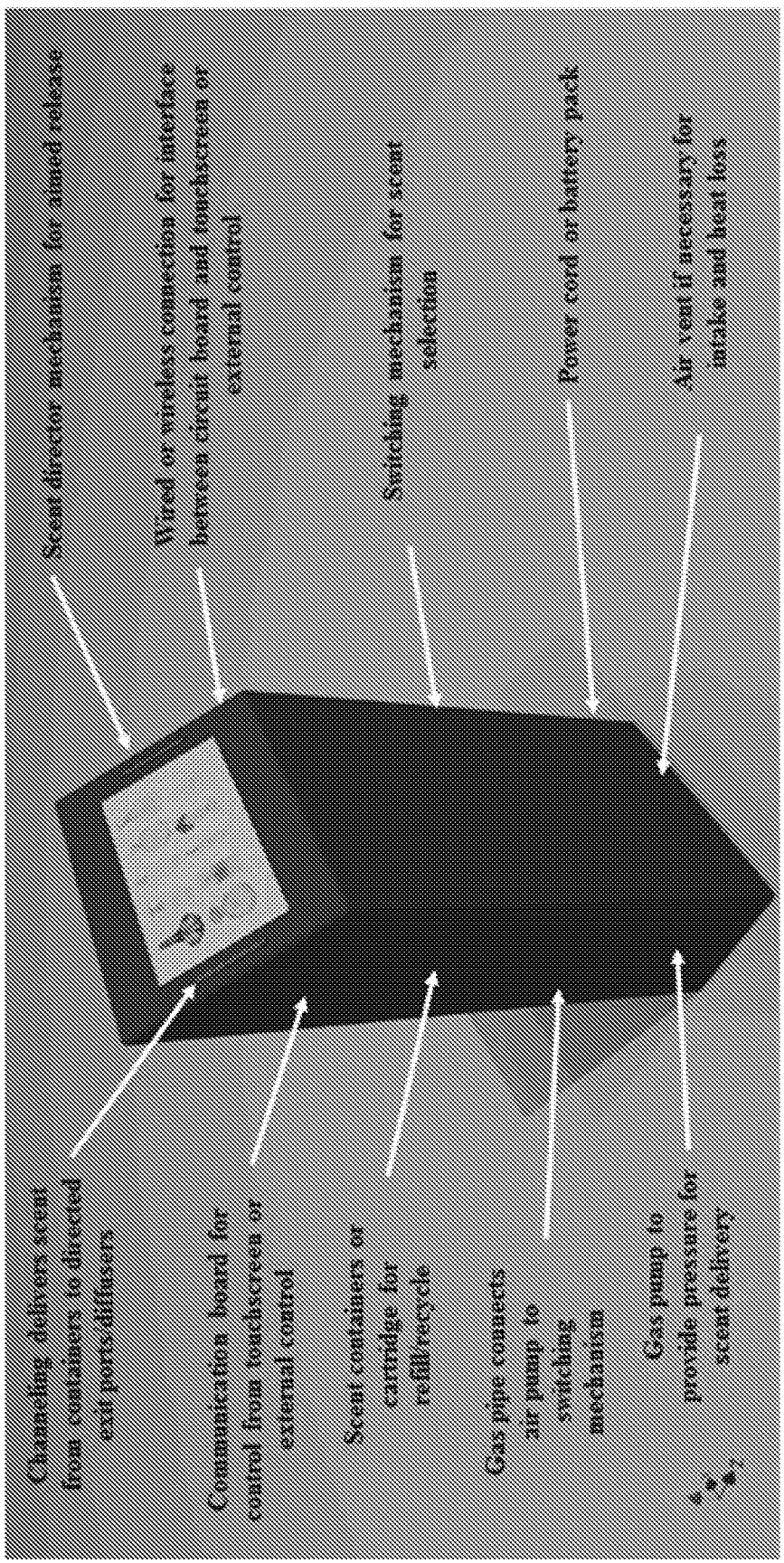

FIG. 4 (R) – Mobile or Stationary Device with Flexible Dimensions and Placement as a Unit: Self-contained scent delivery unit of flexible dimensions and placement. Unit may be a large floor-based stand alone, a smaller tabletop seated unit, or other dimensionally flexible configuration. Unit may have integrated user interface or external connection to any wired or wireless enabled media device. Scent may be replenish by refill or cartridge replacement/recycle.

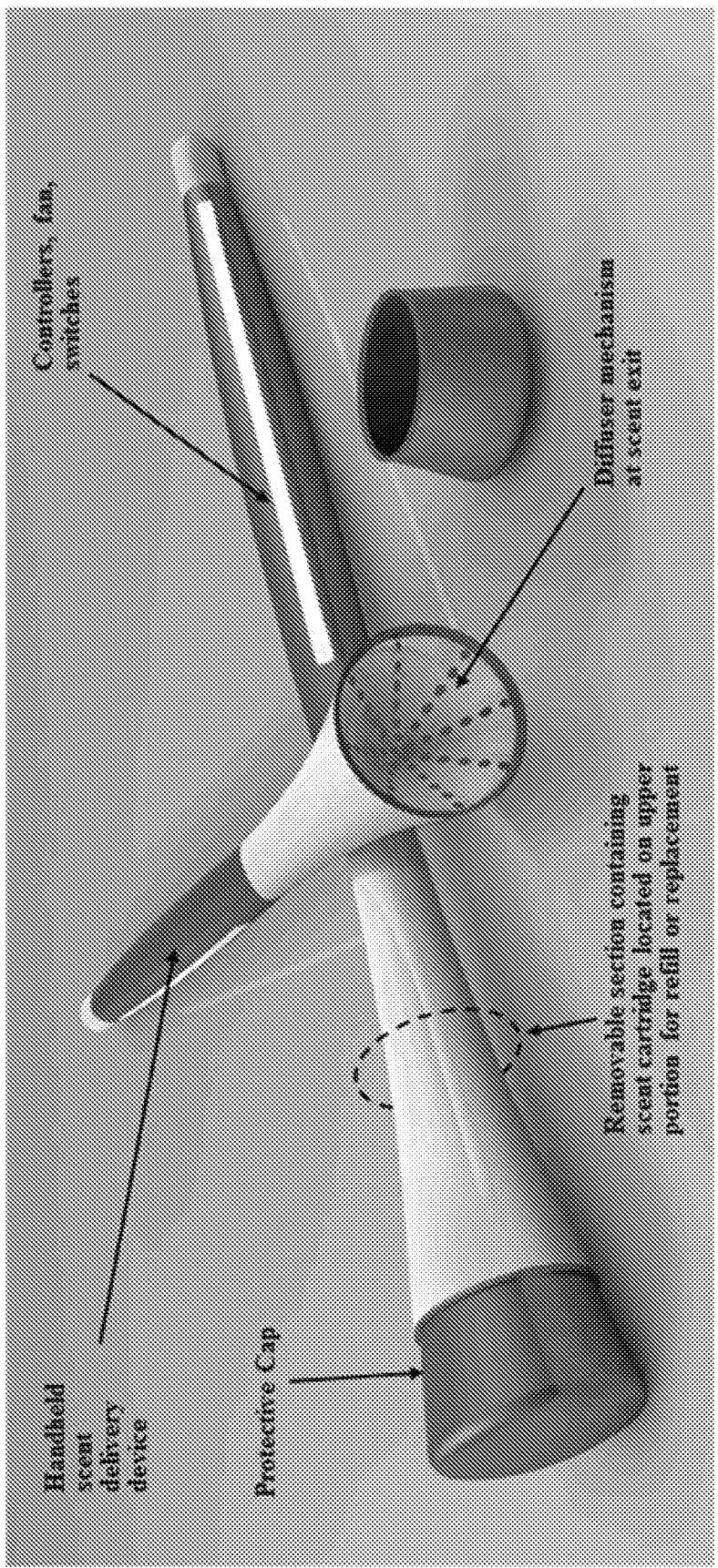

FIG. 4 (S) – Handheld Scent Delivery Device: Self-contained controllable scent delivery from a handheld device with detachable replaceable or refillable cartridge. Scent release is accomplished by pushing gas flow through a removable/replaceable scent cartridge located at upper portion of the handheld with a scent container selected by remanent magnetization switch and scented gas delivered through separate channeling to a scent diffuser at the end of the device. Scent can be programmably actuated by wireless signals (such as Wi-Fi) or wired signals from any communications or media device with suitable software. Device can hold up to hundreds of dedicated and predetermined scents.

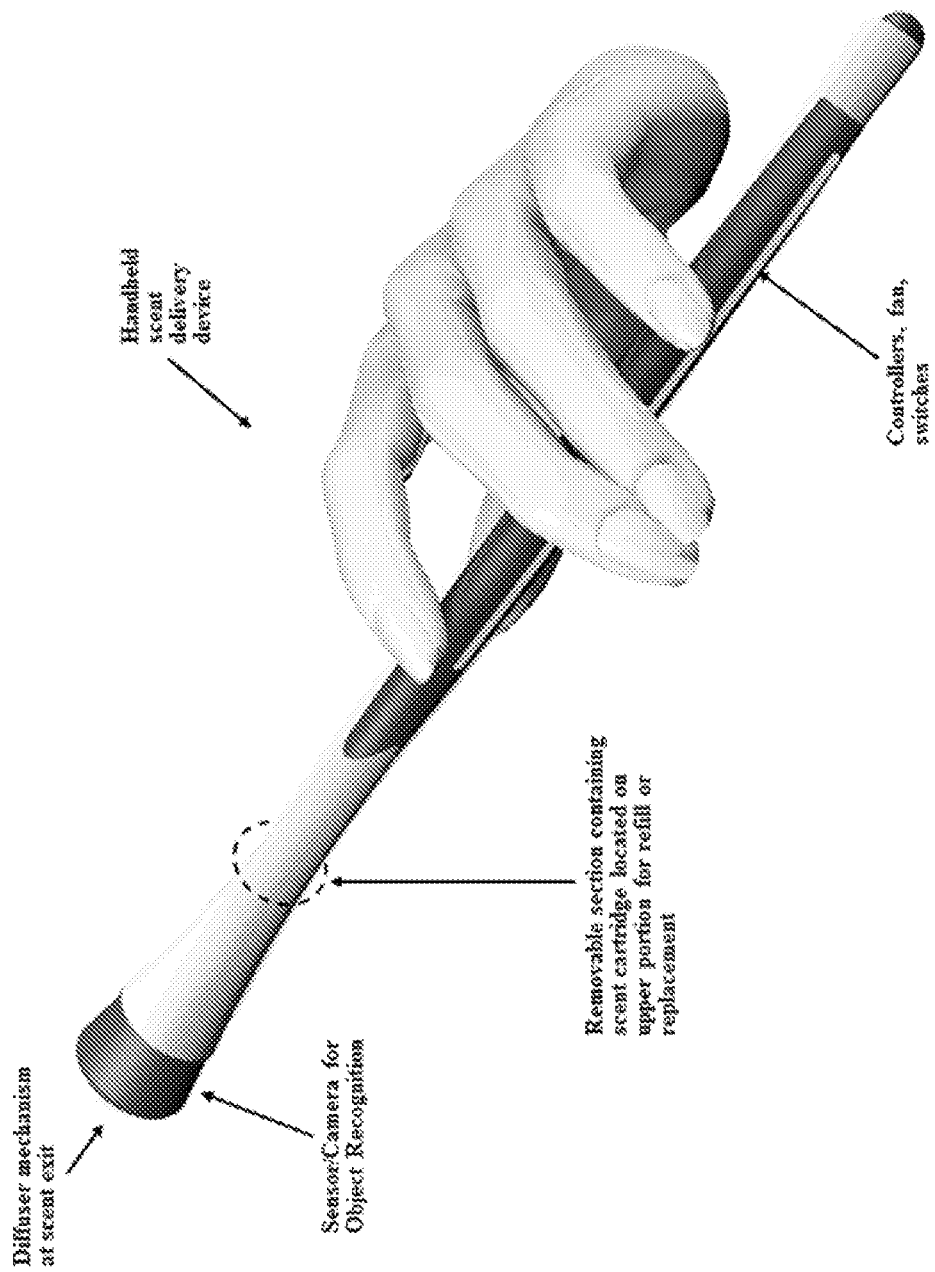
FIG. 4 (T) – Handheld Scent Delivery Device with Object Recognition: With incorporated camera, the handheld device can optionally identify a product and trigger a specified scent. The device can, wired or wirelessly, programmably synchronise to any digital/wireless, electronic, projected, or live media.

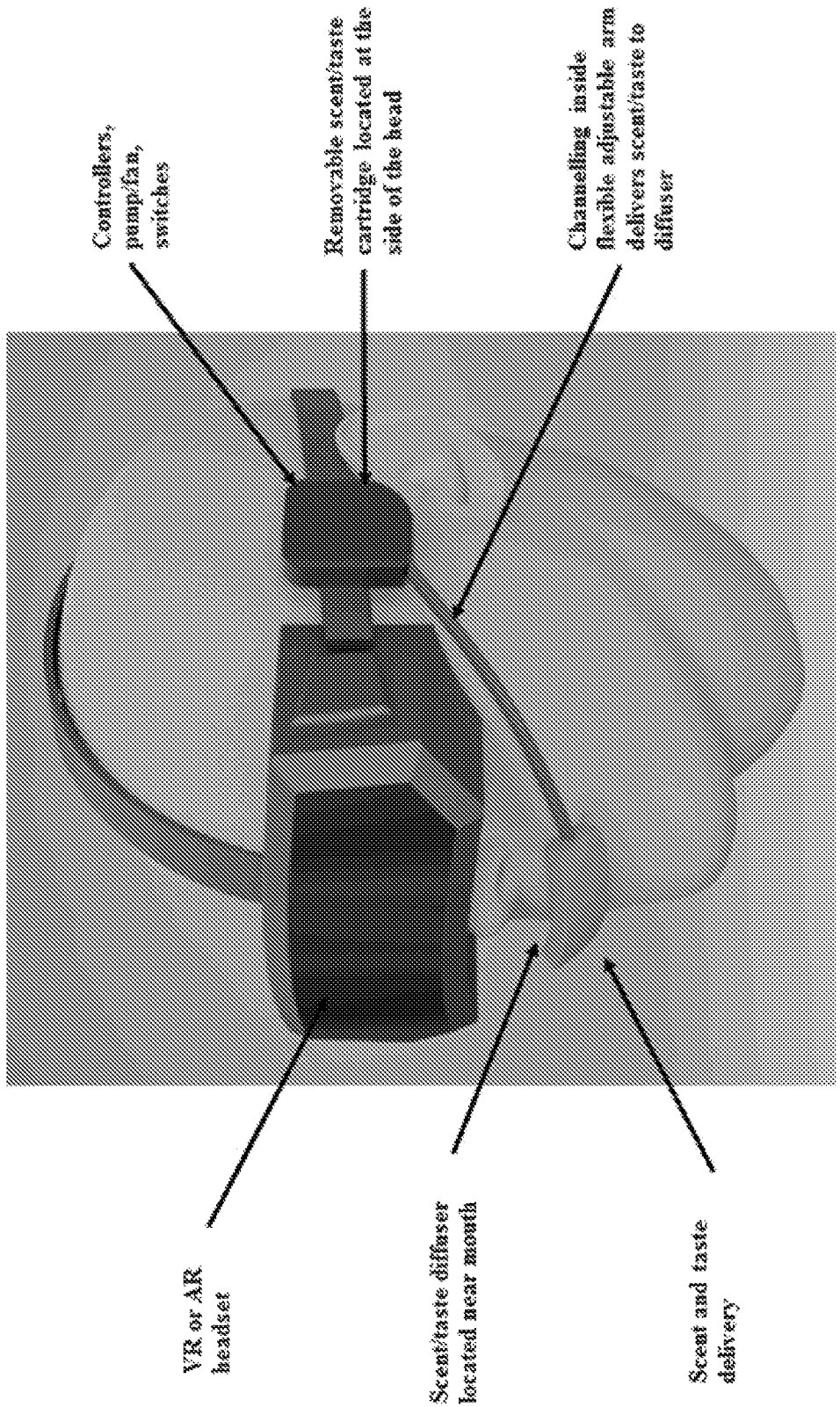
FIG. 4 (U) – Scent Delivery Armature with Integrated Flavor/Taste Delivery: Flavor/Taste distribution may be incorporated into the conveniently located diffuser dispersal mechanism.

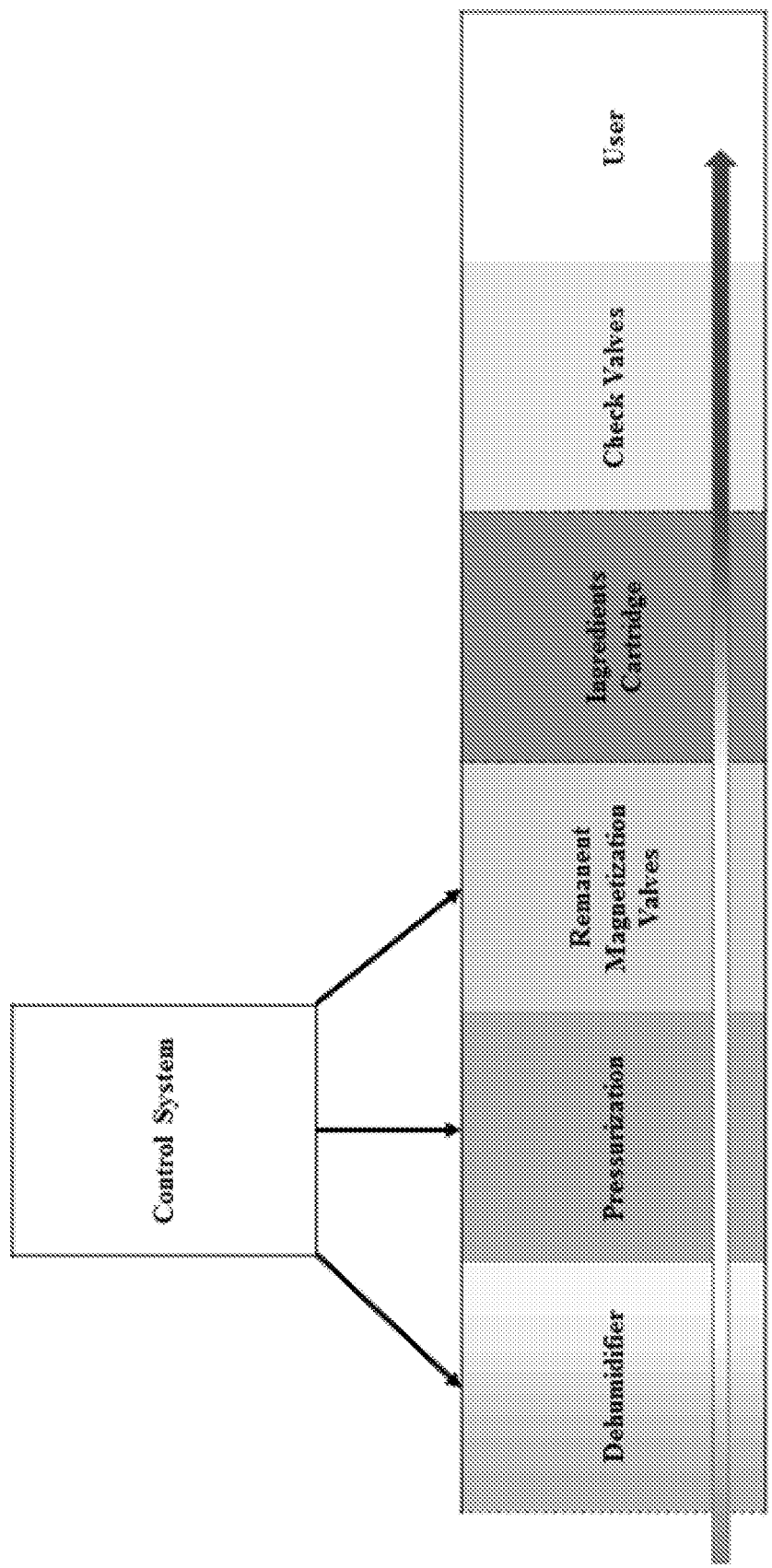
FIG. 4 (V) – Intake Dehumidifier for Multi-climate Operation: As humidity levels may directly impact the quality of fluid production from a scent or other fluid delivery device, optionally, a dehumidifier may be included at the intake port of the device. Such dehumidifier may be always activated, manually activated, or sensor activated.

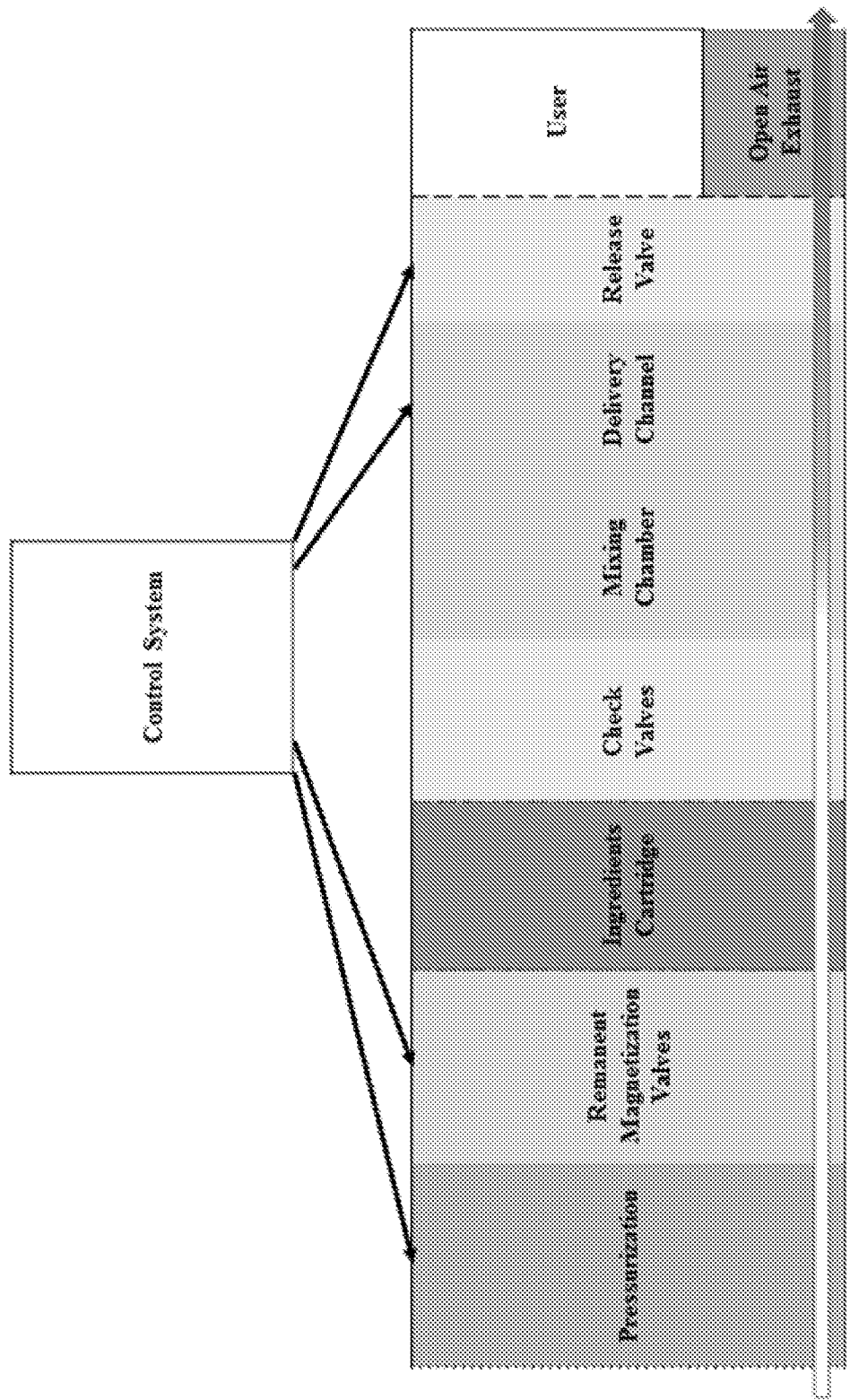

FIG. 4 (W) – Exhaust Mechanism to Vent during Cleaning: For any of the various cleaning mechanisms described herein (see FIG. 5 (A) – (G), an alternative exit valve through which any waste particulate may be discharged is a necessity. Including an additional dual remanent magnetization valve near the device output allows for diverting the flow during and immediately following cleaning. The exhaust valve may be applied to either ready-made cartridge systems or combinatorial blending systems.

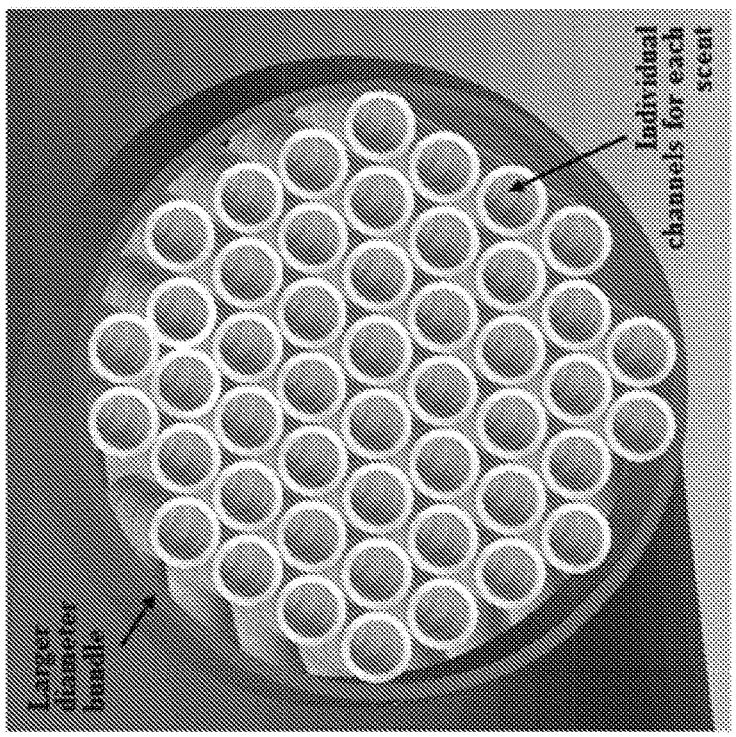

FIG. 5 (A) – Bundled Scent-Specific Delivery Tubes: To prevent cross-contamination of types of fluids, each fluid delivered from a container loaded with that fluid material has a single specific tube that is not shared with any other fluid.

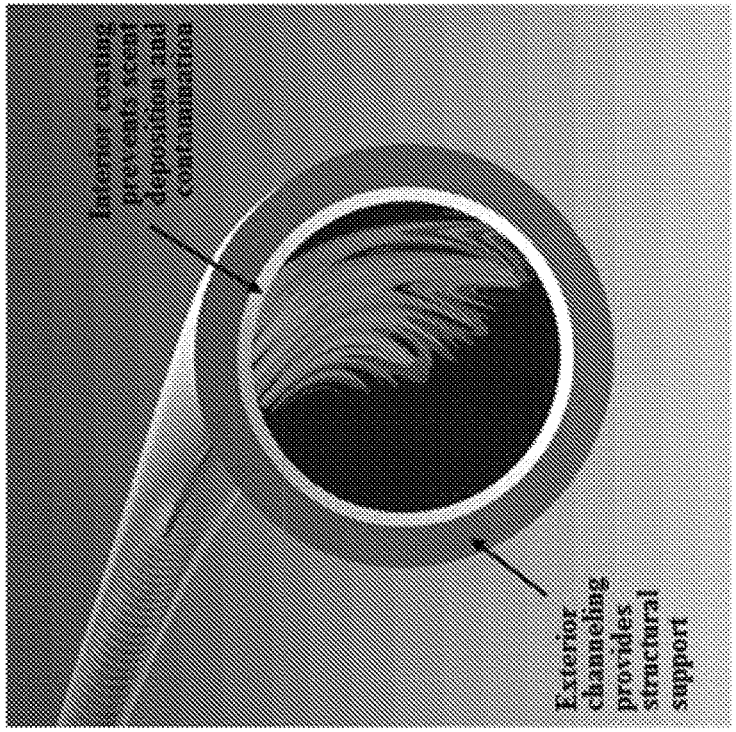

FIG. 5 (B) – Nonporous Residue-Resistant Single Tube: A single residue-resistant fluid delivery tube or channel can accommodate the sequenced release and delivery of many individual differently scented or unscented gases, mists or liquids without deposition on the inside surface of the delivery channel thereby preventing cross-contamination of fluids. A single, fluid delivery channel can significantly reduce the overall size of the device. Tube ( or channel of other geometry] interior can be coated with a hydrophobic and/or lipophobic material/texture or smooth metal/ceramic layer deposition and plating that prevents or minimizes scent accumulations/contaminations.

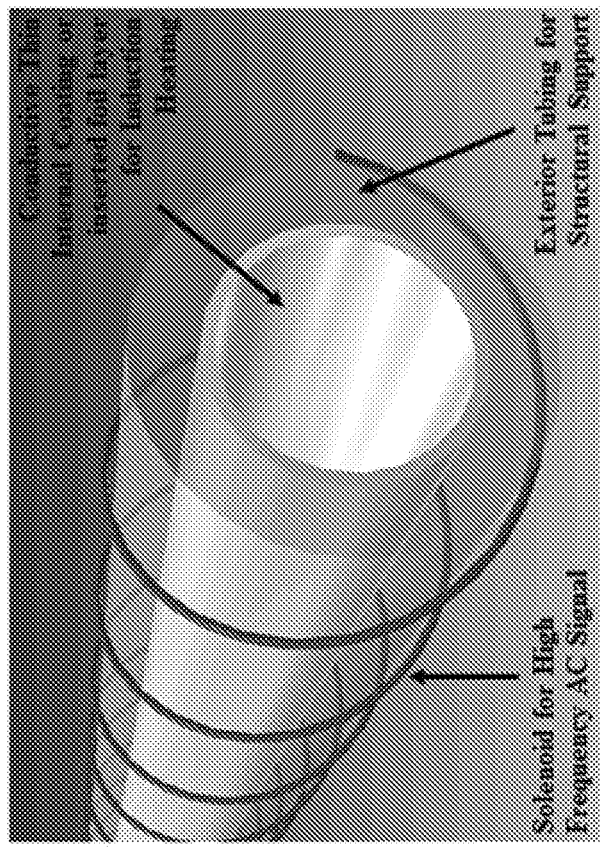
FIG. 5 (D) – Inductive Heating Multi-flow channel: Internal deposition is cleaned by inductive heating of the channel interior.
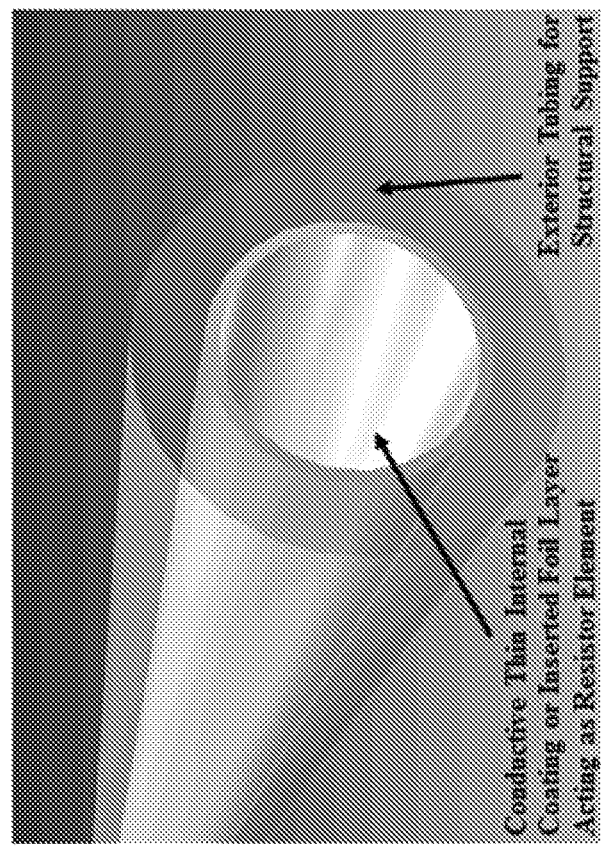
FIG. 5 (C) – Resistive Heating Multi-flow channel: Internal deposition is cleaned by resistive heating of the channel interior.

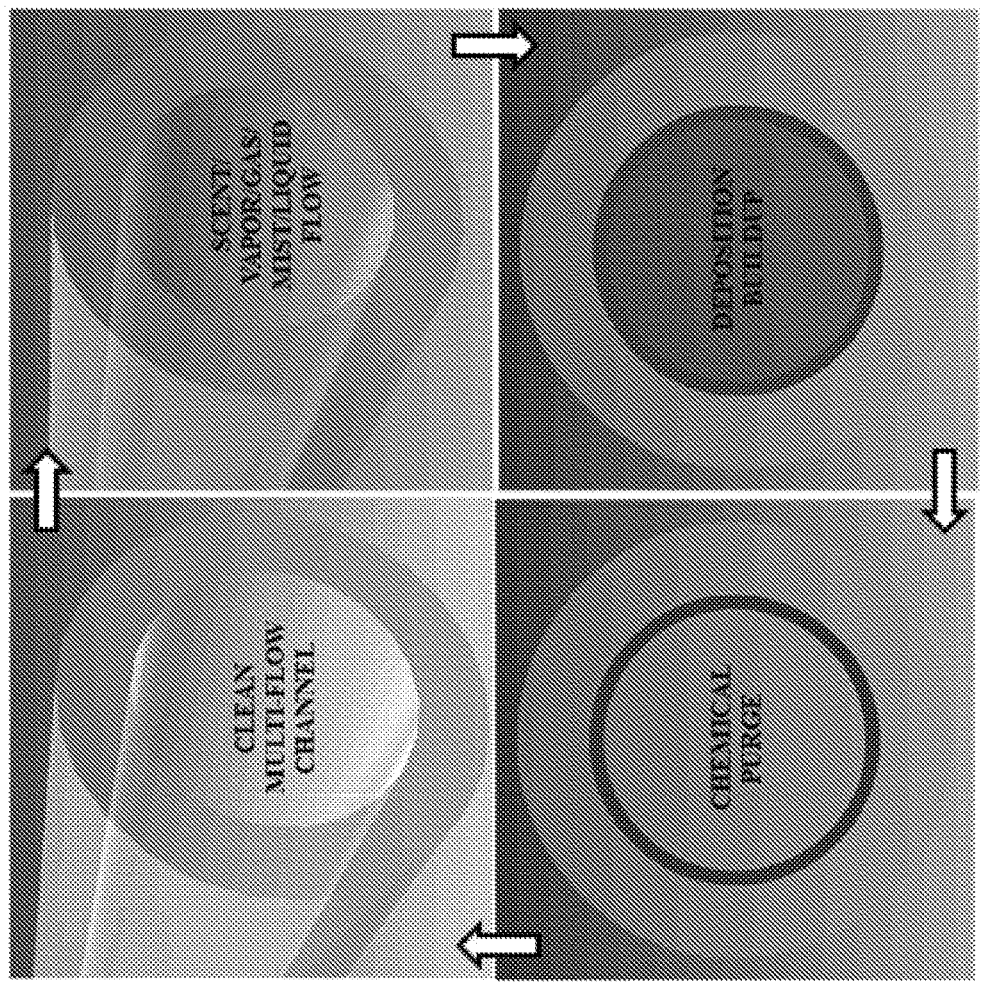
FIG. 5 (E) – Internal Deposition Cleaning by Chemical Purge for Multi-flow channels: Cyclic cleaning with a chemical purge is one viable strategy, perhaps in concert with the other listed options, for automated cleaning of deposition build-up in a multi-flow channel

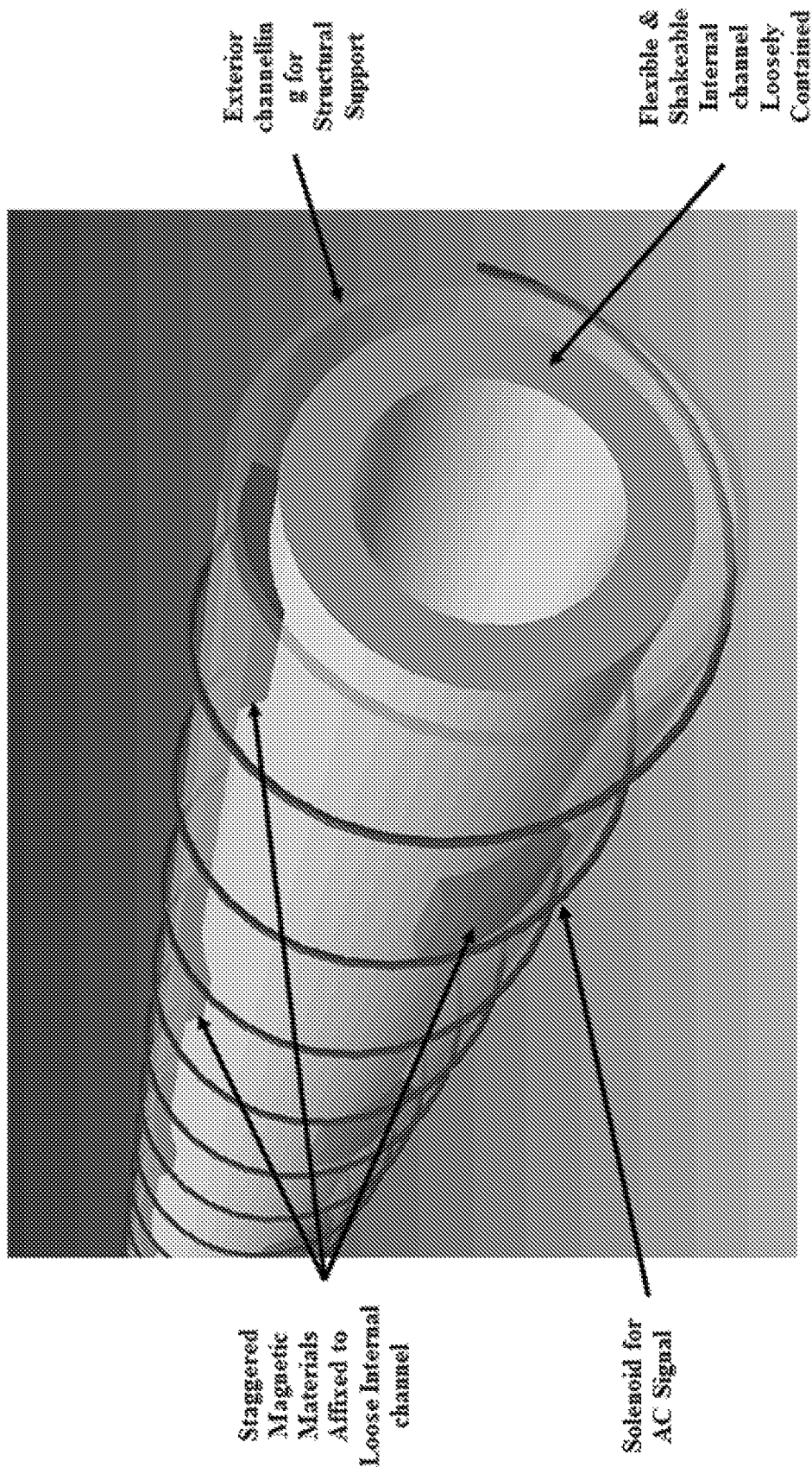
FIG. 5 (F) – Internal Deposition Cleaning by Electromagnetic Shuddering for Multi-flow Tubes: An AC signal produces sufficiently violent shuddering of the internal magnet-affixed tube to loosen deposition build-up. In the case of scent delivery, combination with unscented gas flow through the multi-flow tube, reg

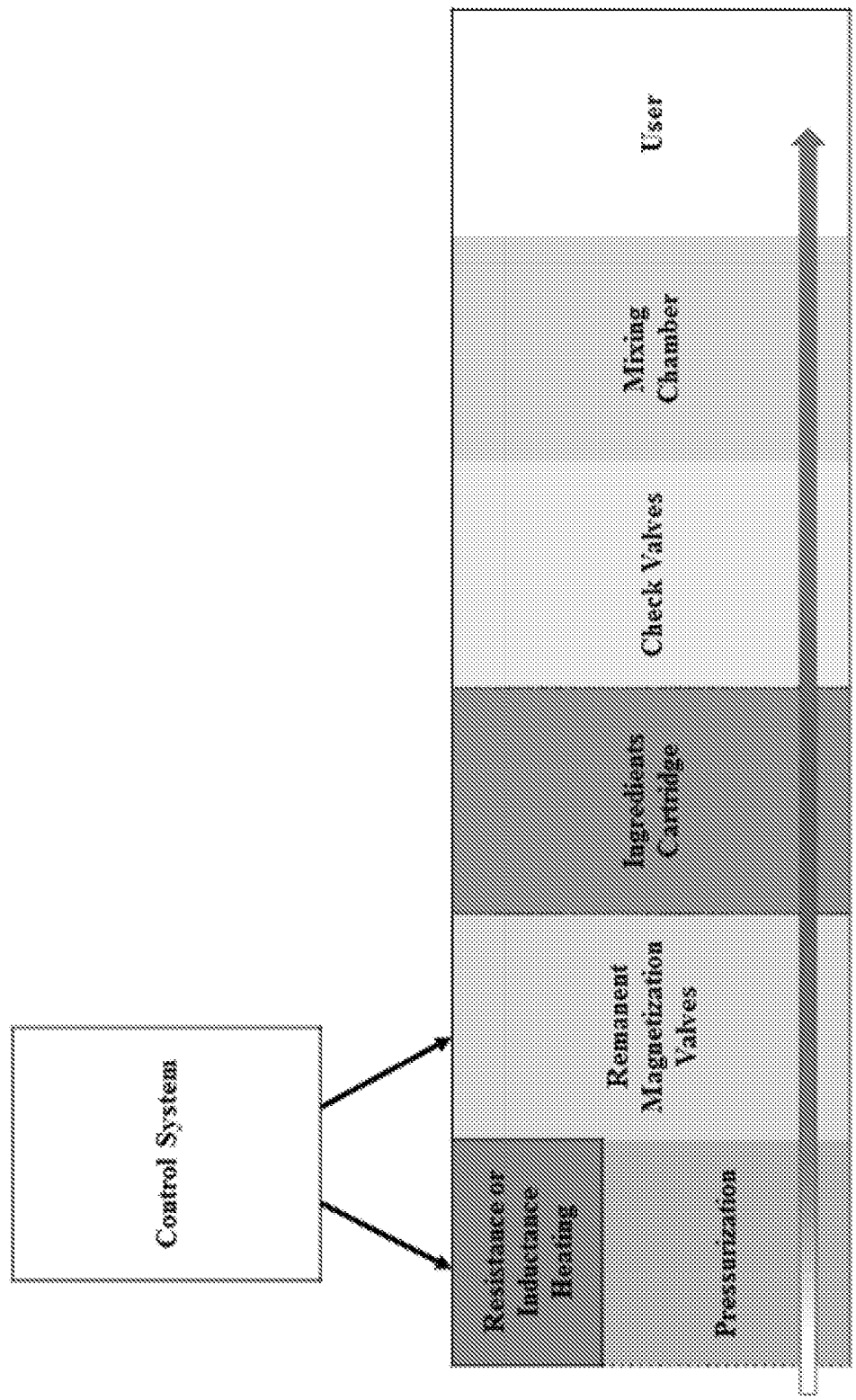

FIG. 5 (G) – Pre- or Intermittent-heating Mechanism for Cleaning System Components: Occasional comprehensive or intermittent internal cleaning of one or a combination of a fluid delivery system's pressurization chamber(s), valves, cartridge(s), and any other chambers with which fluid streams with differing compositions (such as multiple streams with individuated scented gases) interact may be accomplished by the incorporation of a heating mechanism at the intake. In typical applications this cleaning hardware and method would be paired with an exhaust valve prior to release as in FIG. 4 (W).

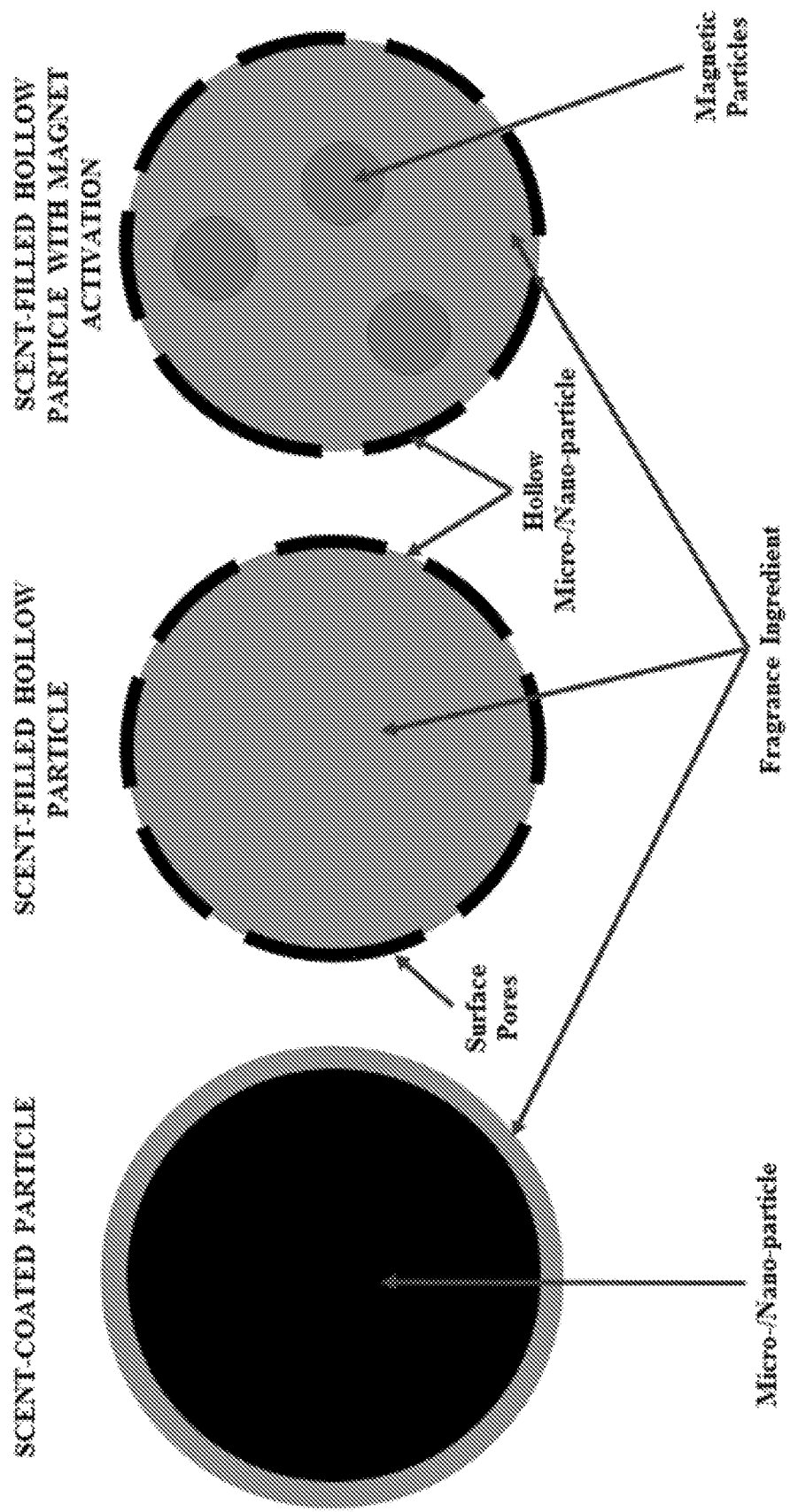

FIG. 6 (A) – Coated or Hollow Porous Micro-/Nano-particles for Scent Ingredient Retention, Optionally with Magnetic Particle Activation: Coated micro- or nano-particles allow for the high surface area to volume ratios necessary for scent delivery. Moving to a hollow, porous particles allows for longer play durations while retaining the high surface area advantage. Inclusion of magnetic inner particles permits activated release via exposure to an electromagnetic field.

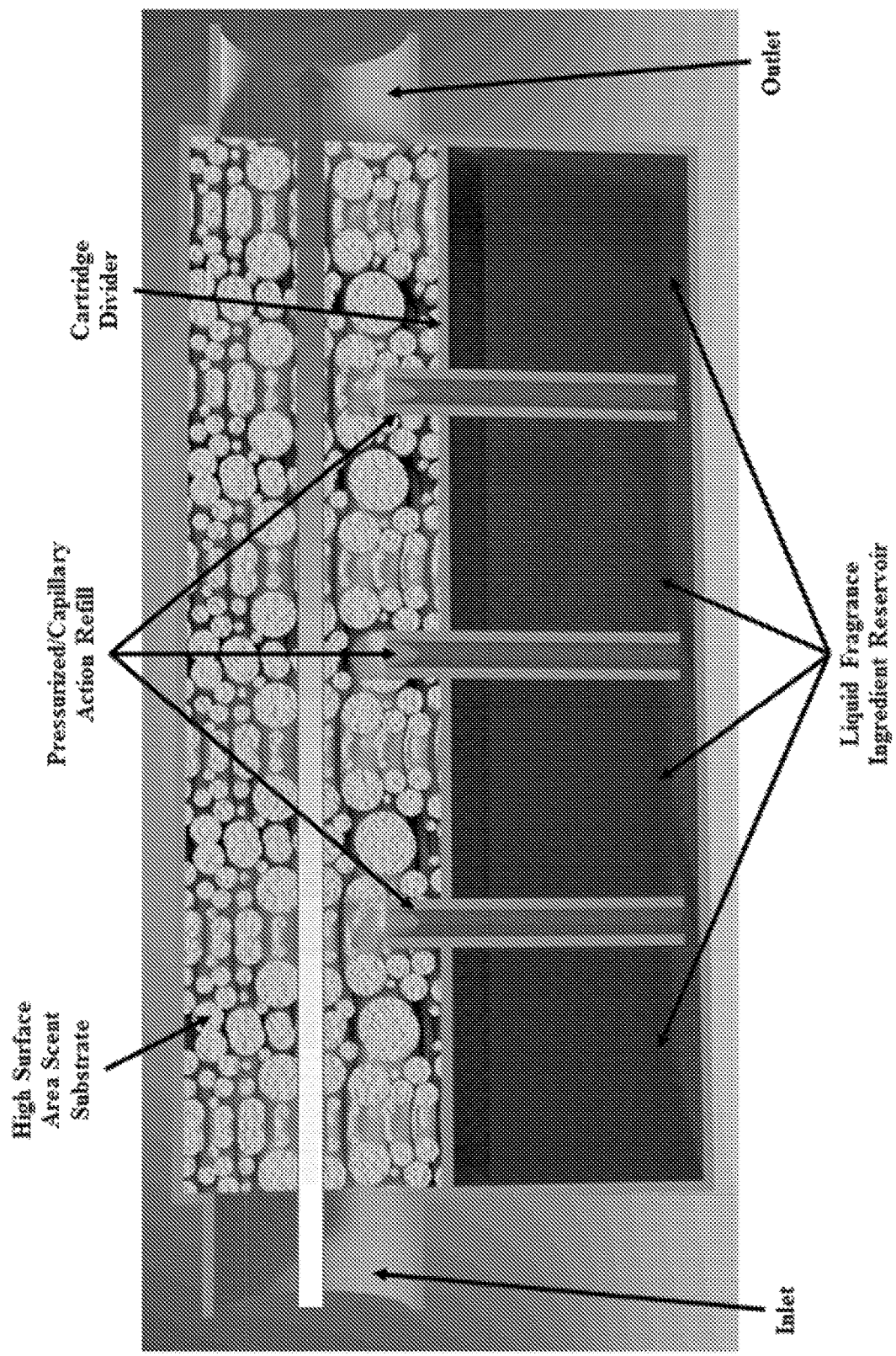
FIG. 6 (B) – Divided Cartridge Containers: For longer-term cartridge deployment, a scent liquid ingredient reservoir is included to periodically or continually replenish the adjacent scent substrate. Transfer from the liquid chamber may be accomplished by capillary action, pressurization, or similar.

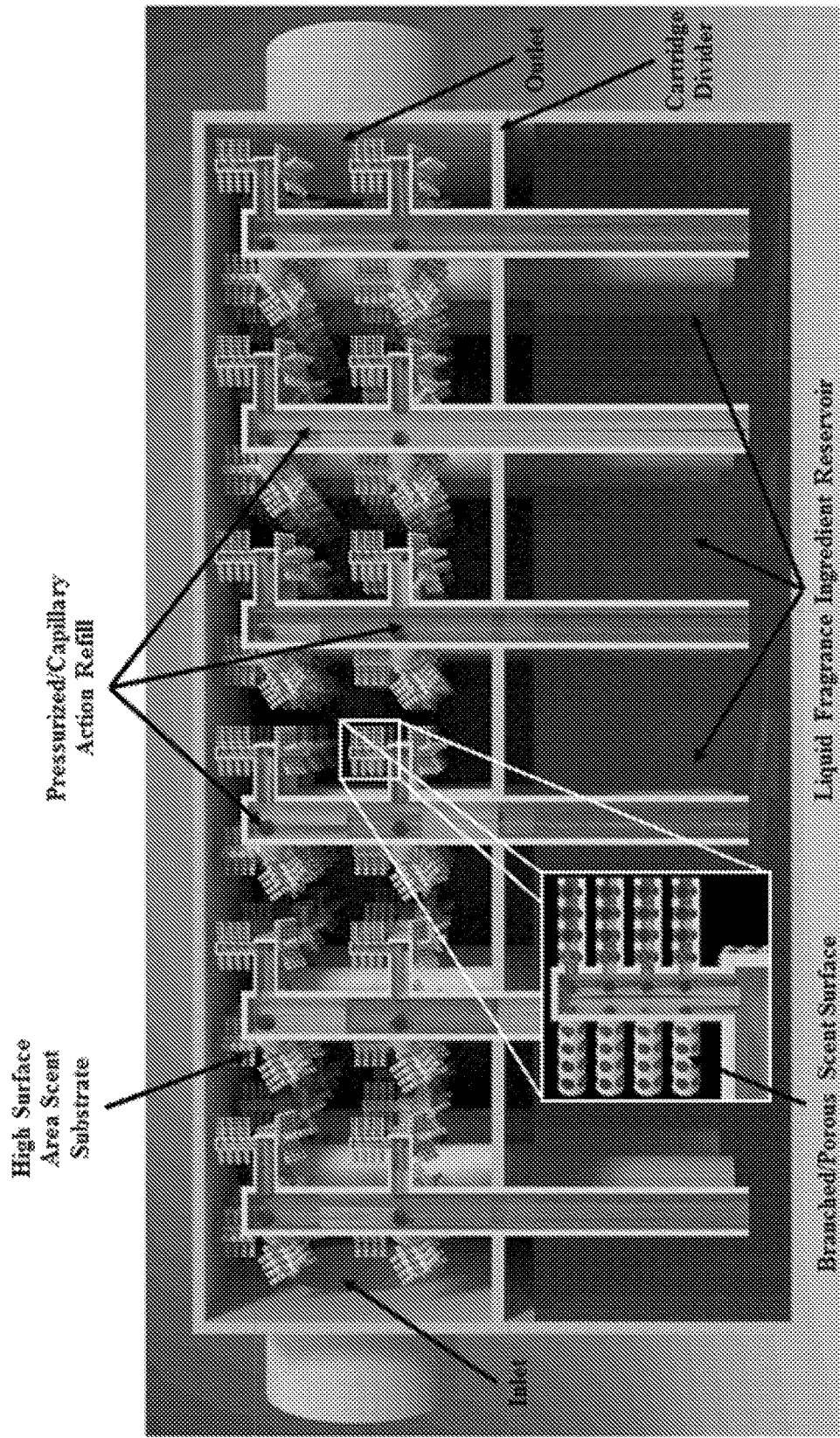

FIG. 6 (C) – Divided Cartridge Container with Branched Liquid Feed: For longer-term cartridge deployment, a liquid scent ingredient reservoir is included to periodically or continually replenish the adjacent scent substrate consisting of multi-branched porous micro- or nano-cylinders to maximize surface area. As depicted above only 3 levels of branching are shown. However, as implemented branching may continue to additional smaller steps. Transfer from the liquid chamber may be accomplished by capillary action, pressurization, or similar.

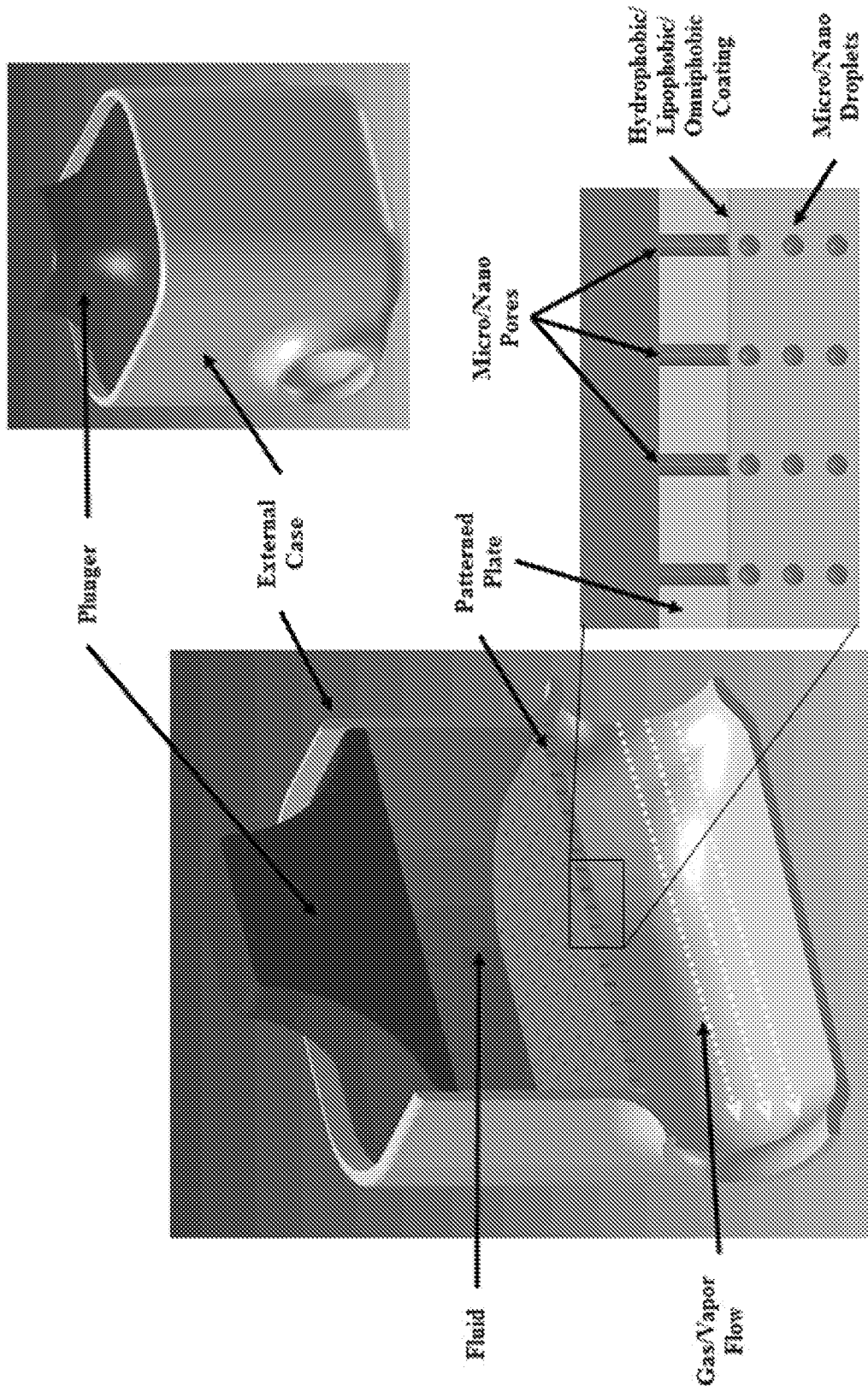
FIG. 6 (D) – Mist Generation by Forcing Liquid through Small Diameter Patterned Plate: Drop separation may be promoted via resistive heating, inductive heating, or use of catalytic surfaces.

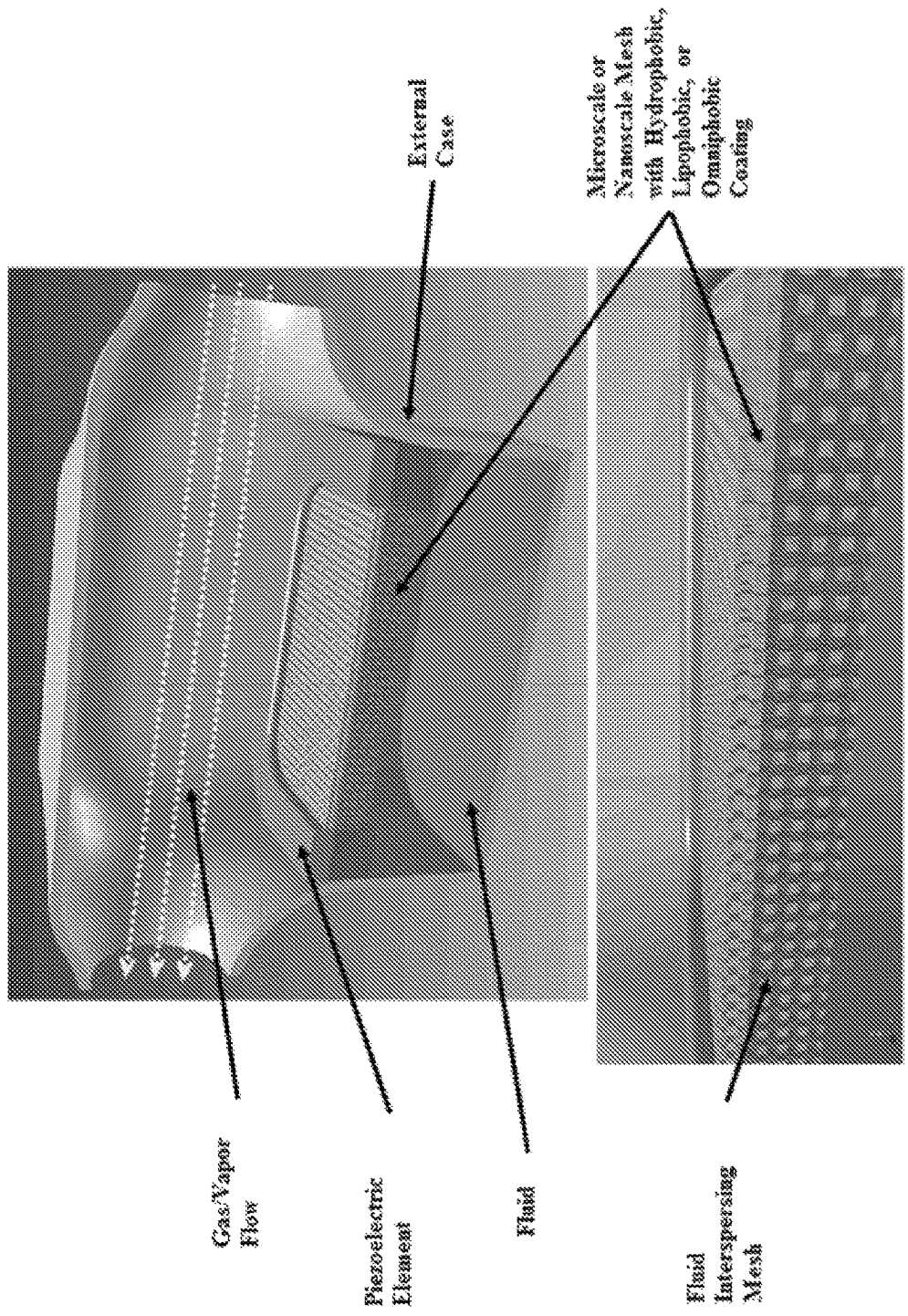
FIG. 6 (E) – Mist Generation by Piezoelectric Shaking of Hydrophobic, Lipophobic, or Omniphobic Mesh: Drop separation may be promoted via resistive heating, inductive heating, or use of catalytic surfaces.

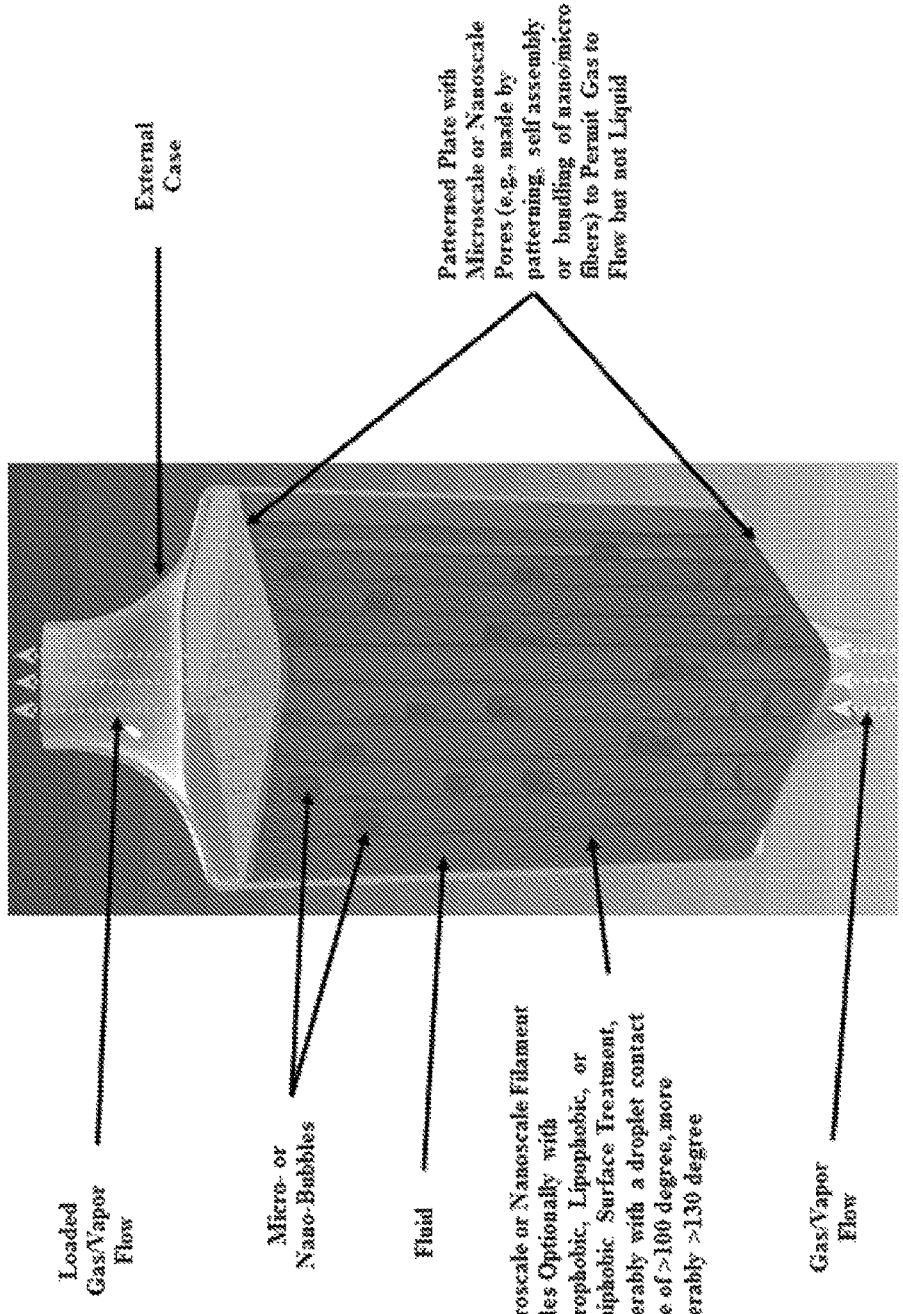
FIG. 6 (F) – Continuous Vaporization through Micro- or Nano-bubble Dispersion with Filament Guides: Treatment to promote hydrophobic, lipophobic, or omniphobic surfaces on the filament array may further promote bubble formation.

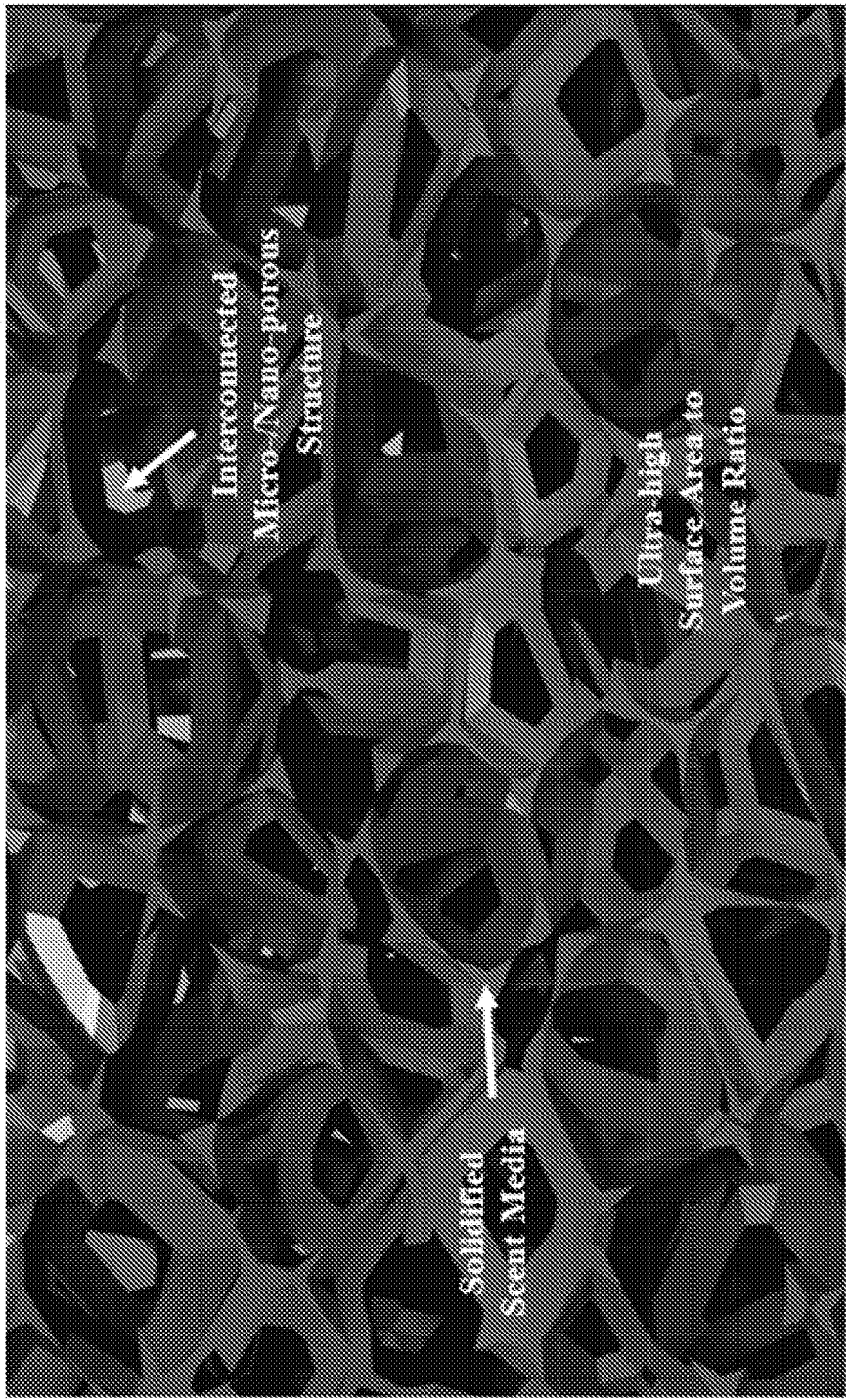

FIG. 6 (G) – Ultra-high Concentration SCENT Ingredients for Extended Playable Scent Duration: SCENT ingredient specific, solid, interconnected, and nonporous media allows for extended lifetimes and miniaturization. Alternative gas compositions (i.e. combinations and/or concentrations of oxygen, nitrogen, argon, etc.) to limit oxidization over extended use or to enhance sensory perception.

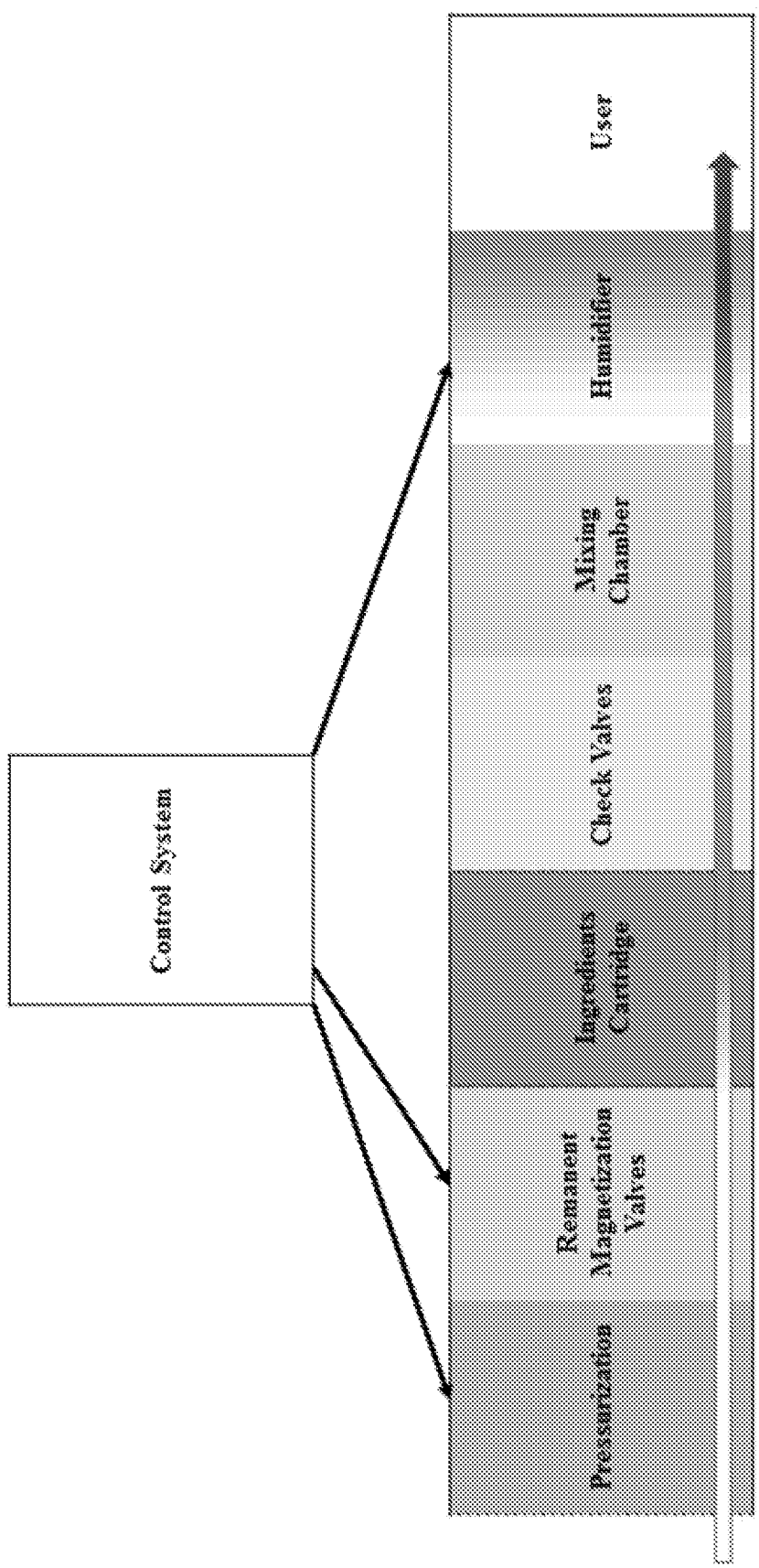
FIG. 7 (A) – Humidifying at the Exit Port or during Mixing for Long-term Comfort: To preclude unpleasant chapping of lips or nostrils from an extended use duration of a scent delivery device, a humidifier may be optionally included prior to scent output. Such humidifier may be always activated, manually activated, or sensor activated.

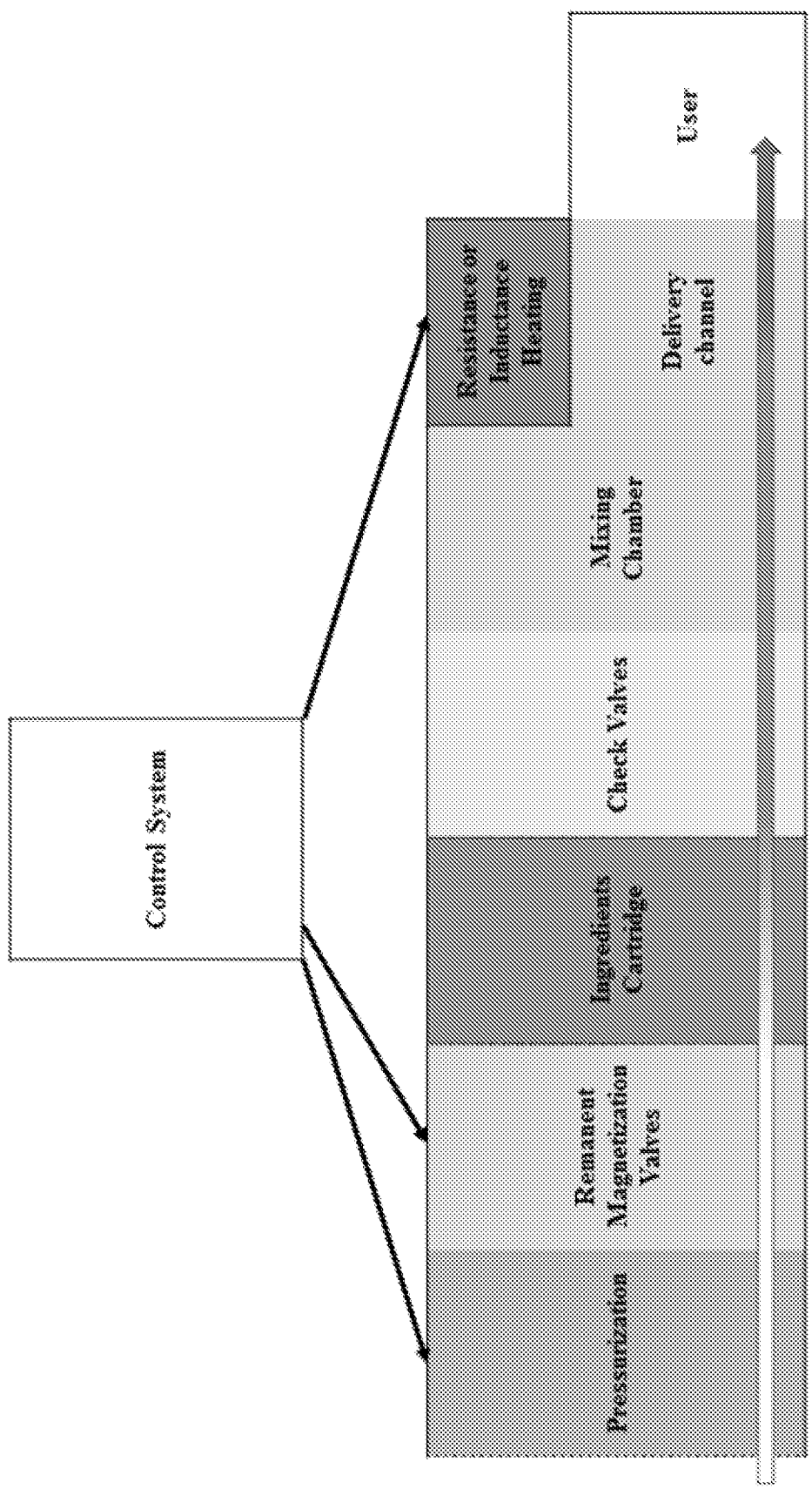
FIG. 7 (B) – Modulated Heating Mechanism as an Additional Sensory Component: For sensory applications that require it, scent delivery may optionally be heated via controlled resistive or inductive heating.

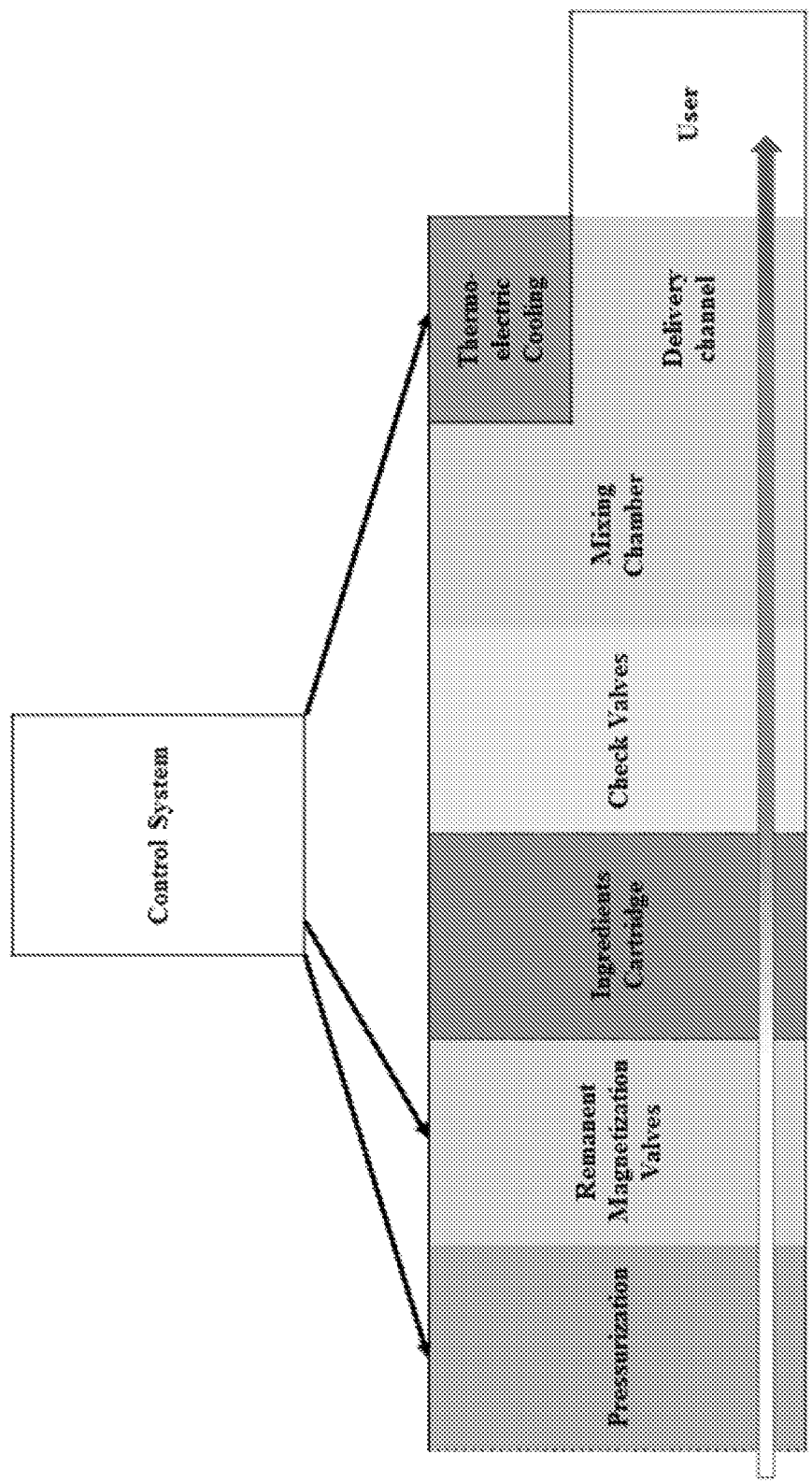
FIG. 7 (C) – Modulated Cooling System as an Additional Sensory Component: For sensory applications that require it, scent delivery may optionally be cooled via controlled thermoelectric or similar cooling.

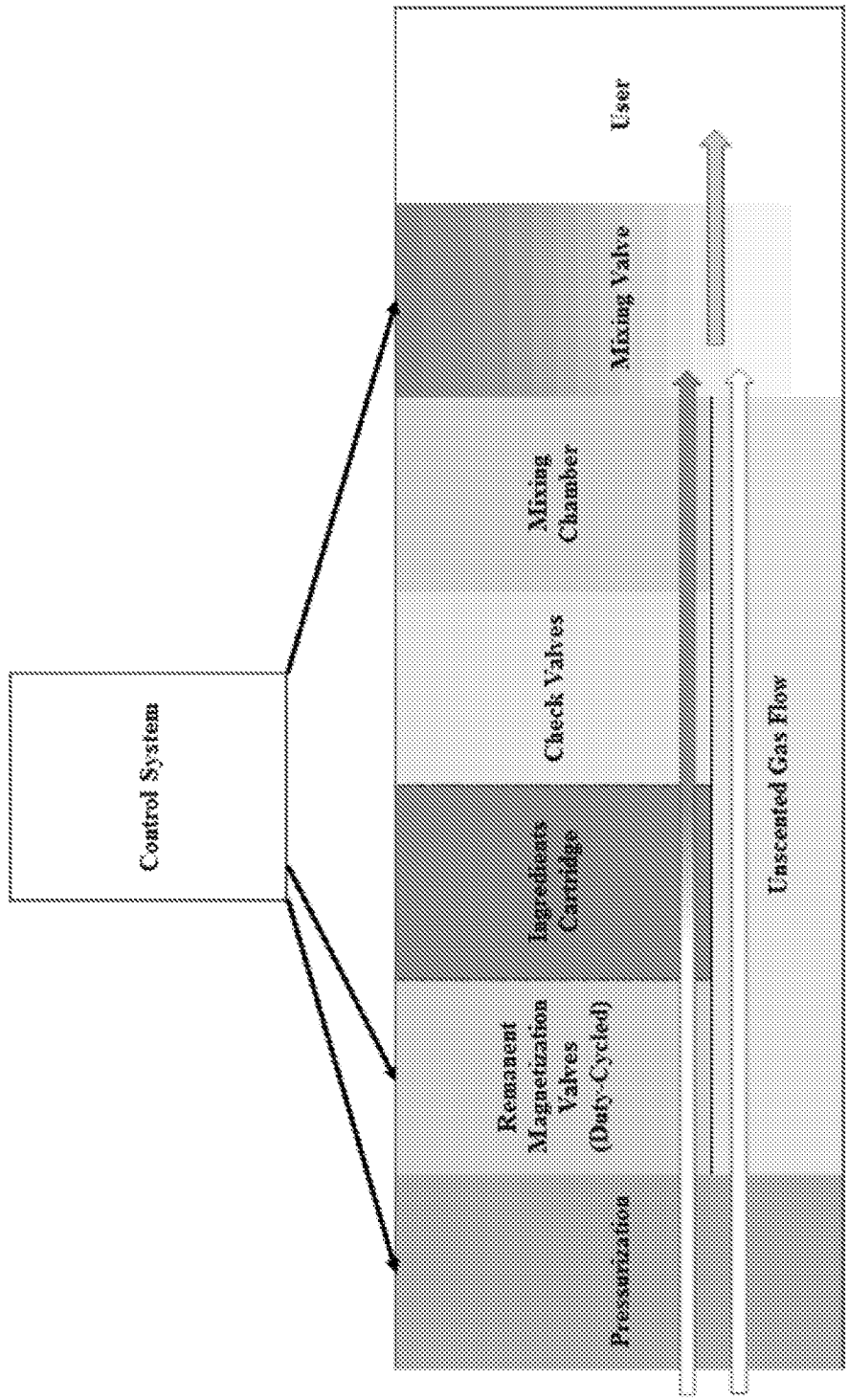

FIG. 7 (D) – Scent Volume is Controlled via High Frequency Cycling of Remanent Magnetization Valves, Pressure Variation, or Metered Dilution with Unscented Gas: Similar to volume control for audio deployments or brightness control for video deployments, scent delivery may optionally include an intensity control system relying on dilution levels, duty-cycling, or pressurization.

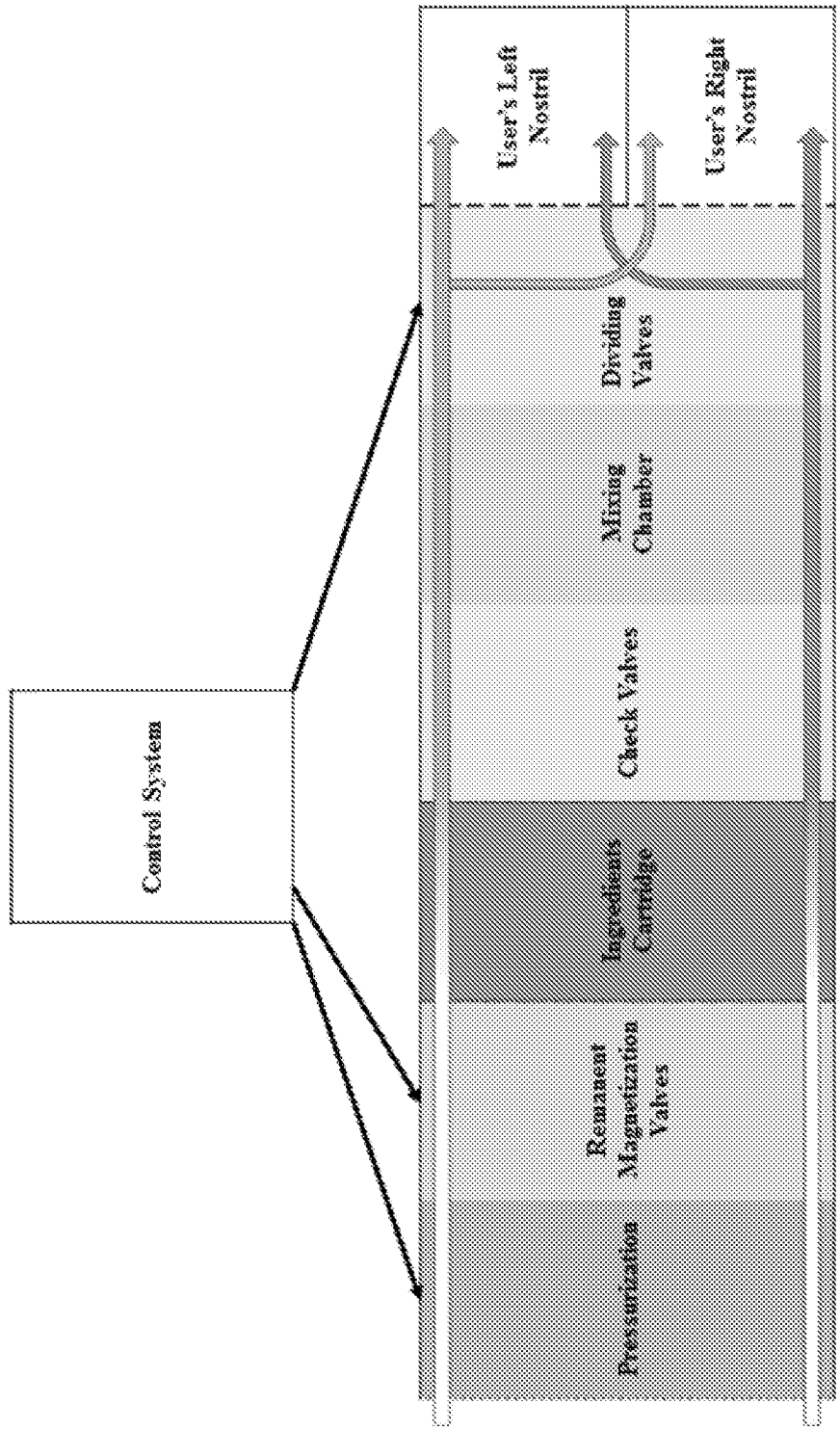

FIG. 7 (E) – Dual Nostril Feed for 3D Scent Delivery: For directional scents, employing dual scent streams with varying scent compositions allows for precise control of scent perception. A dividing valve may be used for variable control as indicated or separated channels could be fitting as dictated by the application. Additionally, channels can be further subdivided for multiple channel delivery to each nostril.

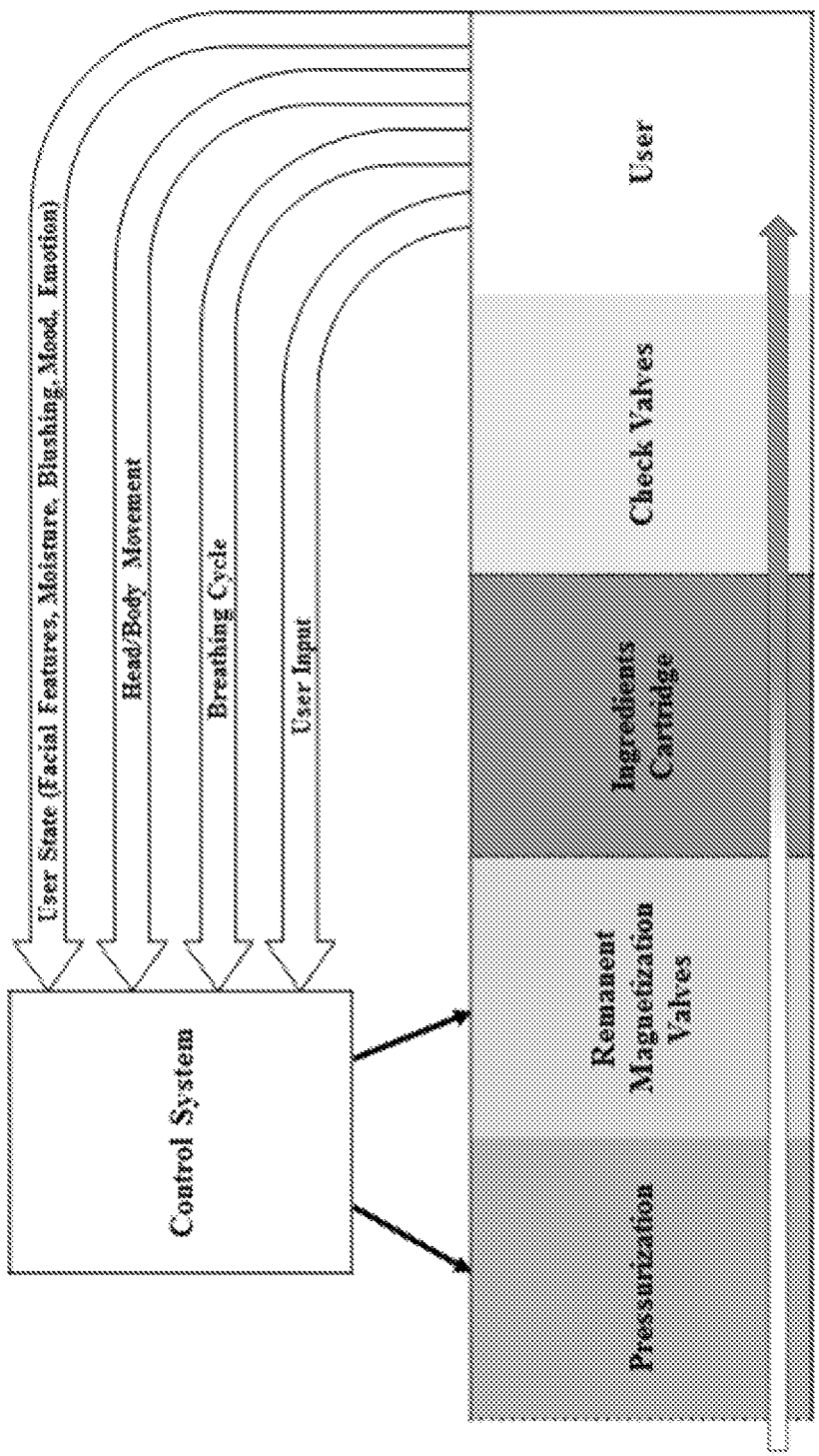

FIG. 7 (F) – Integrated Biosensors: Camera/sensors (or link to one in AR/VR device) for optical / motion capture and detection of facial features and expressions, movement of the head or body (to interpret emotion as well as to use for interpretation of the distance and location in 3D virtual space of a scent from the user, and breathing (the last of which can be used to synchronize scent delivery to an individual's breathing or breathing cycle).

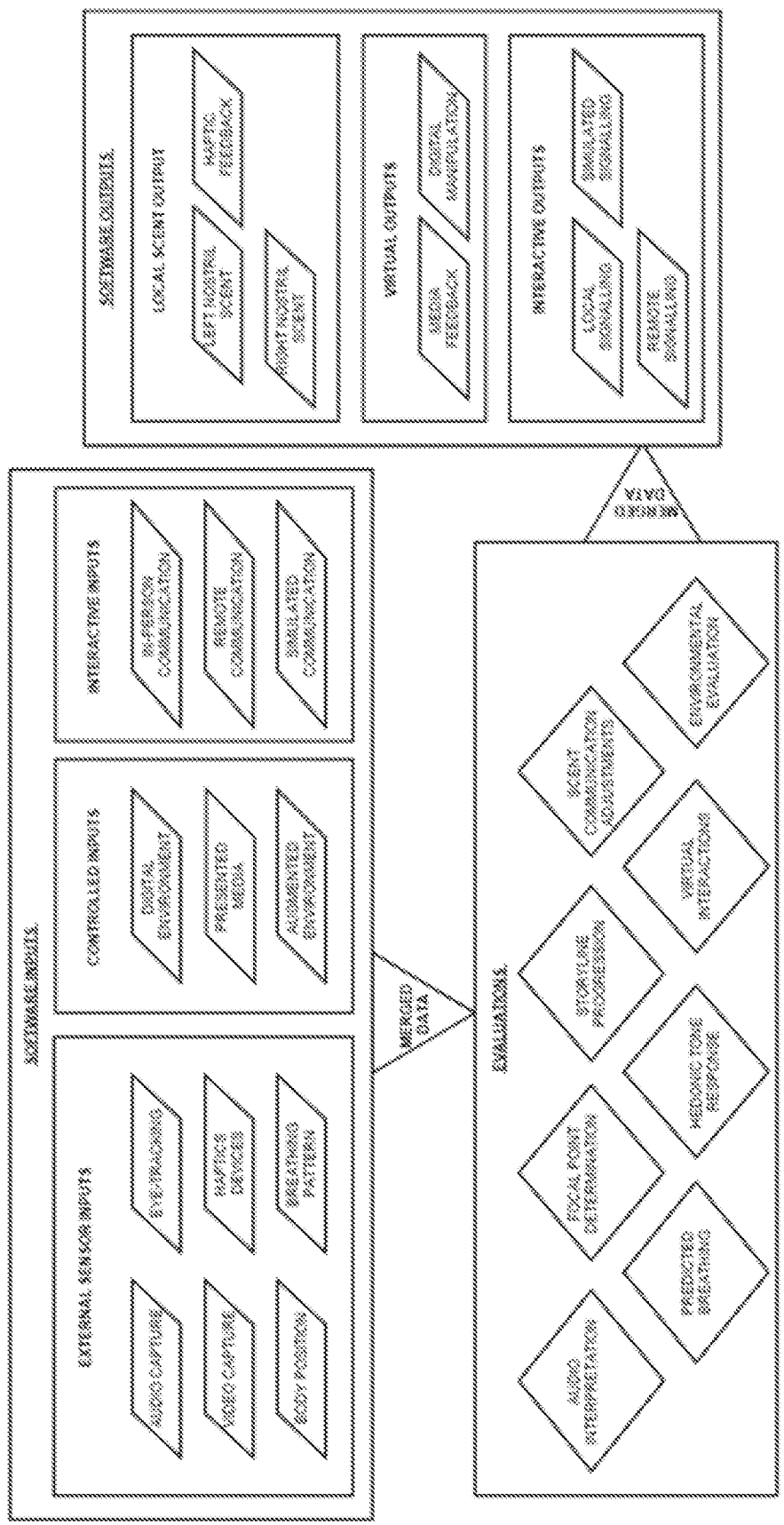

FIG. 7 (G) – Programmatic Functions for an Enhanced Scent Experience: Basic layouts of software inputs, functions, and outputs for a fully functional, responsive, integrated scent delivery device which actively or programmatically adjusts scent outputs according to user feedback, virtual or digital media and/or user(s) interactions, interactivity or exchanges between users, and designed parameters.

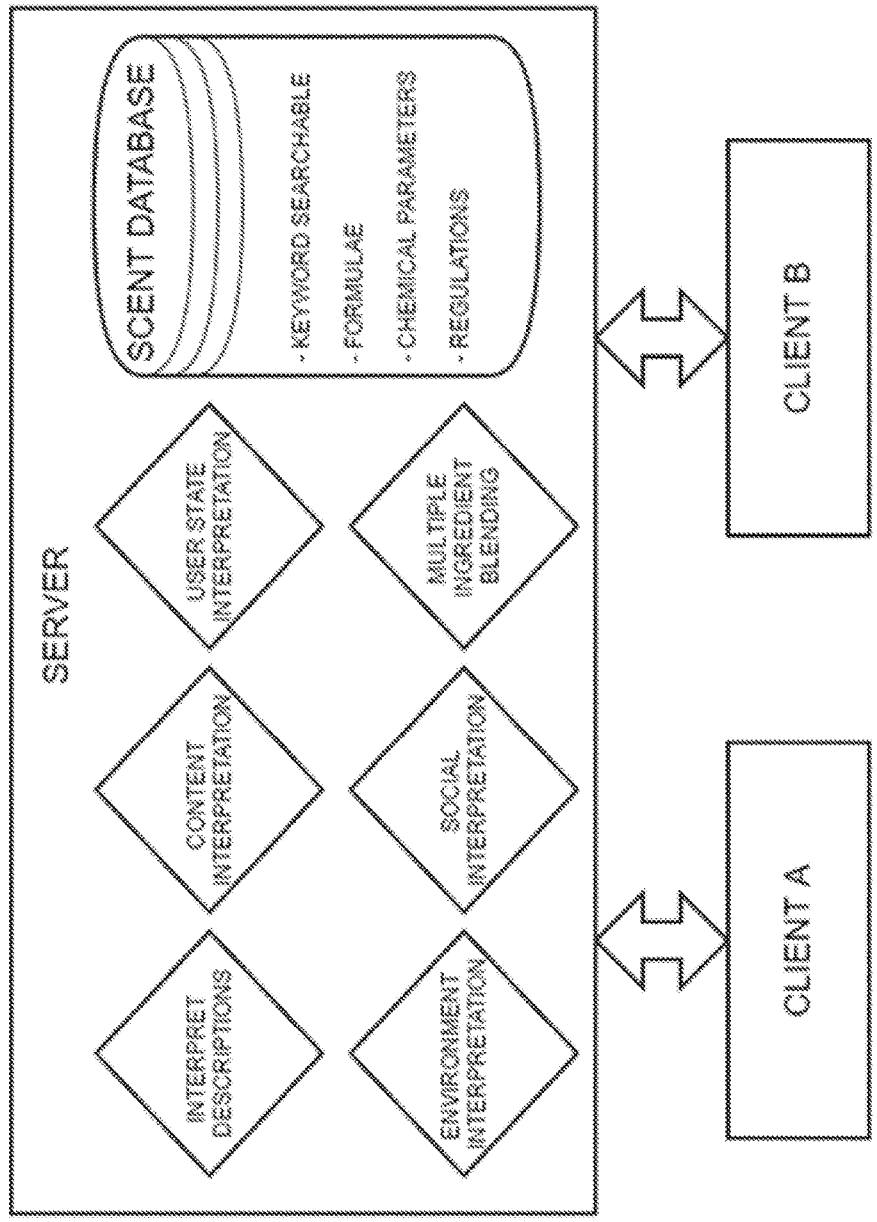

FIG. 7 (H) – User Scent Design, Exchange, Transmission: Consumers, commercial or other types of users may design new scents or programmatically select scents from a database drawing from tabulated formulae, chemical parameters, and pertinent regulatory restrictions (i.e. restricted use of chemicals or chemical concentrations for delivery) for wired or wireless instructions (transmission) to other user devices with compliant software to trigger timed or real-time blending or cartridge selection and device release. Instructions may be transmitted from one or a group or users to others for purposes, for example, of (i) sharing or exchange of scents (ii) synchronization with the play of scented media of any type (egg books, email, films, videogames, music, etc.), (iii) for online shopping, etc. Programmatic interpretation of descriptions, content, user state, environment, social, psychometric, and chemical blending parameters enable programmatic or automated digital scent creation and device delivery.

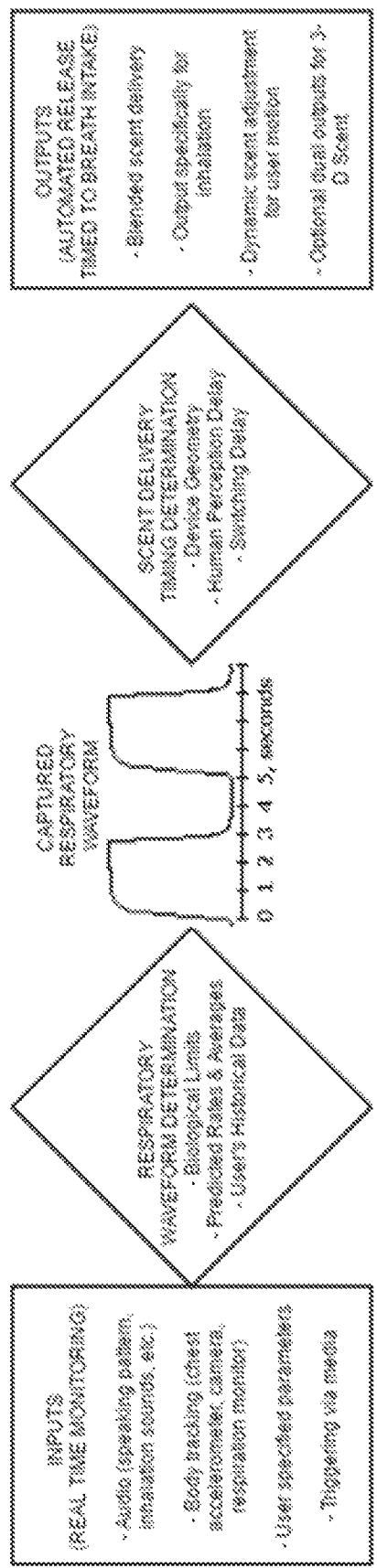

FIG. 7 (I) – Scent Delivery Dynamic, Synchronous with Breathing: Active monitoring of a scent device user (e.g., his/her audio, body position, reactions) allows for a programmatic determination/estimation of their respiratory waveform. Knowledge of the anticipated or real-time intervals between delivery activation and perception (accounting for device geometry, human perception, and switching time) allows for output adjustments such that scent is only supplied during breath intake (inhalation). Further dynamic adjustments incorporate 3-D delivery, motion adjustments, and blending formulae.

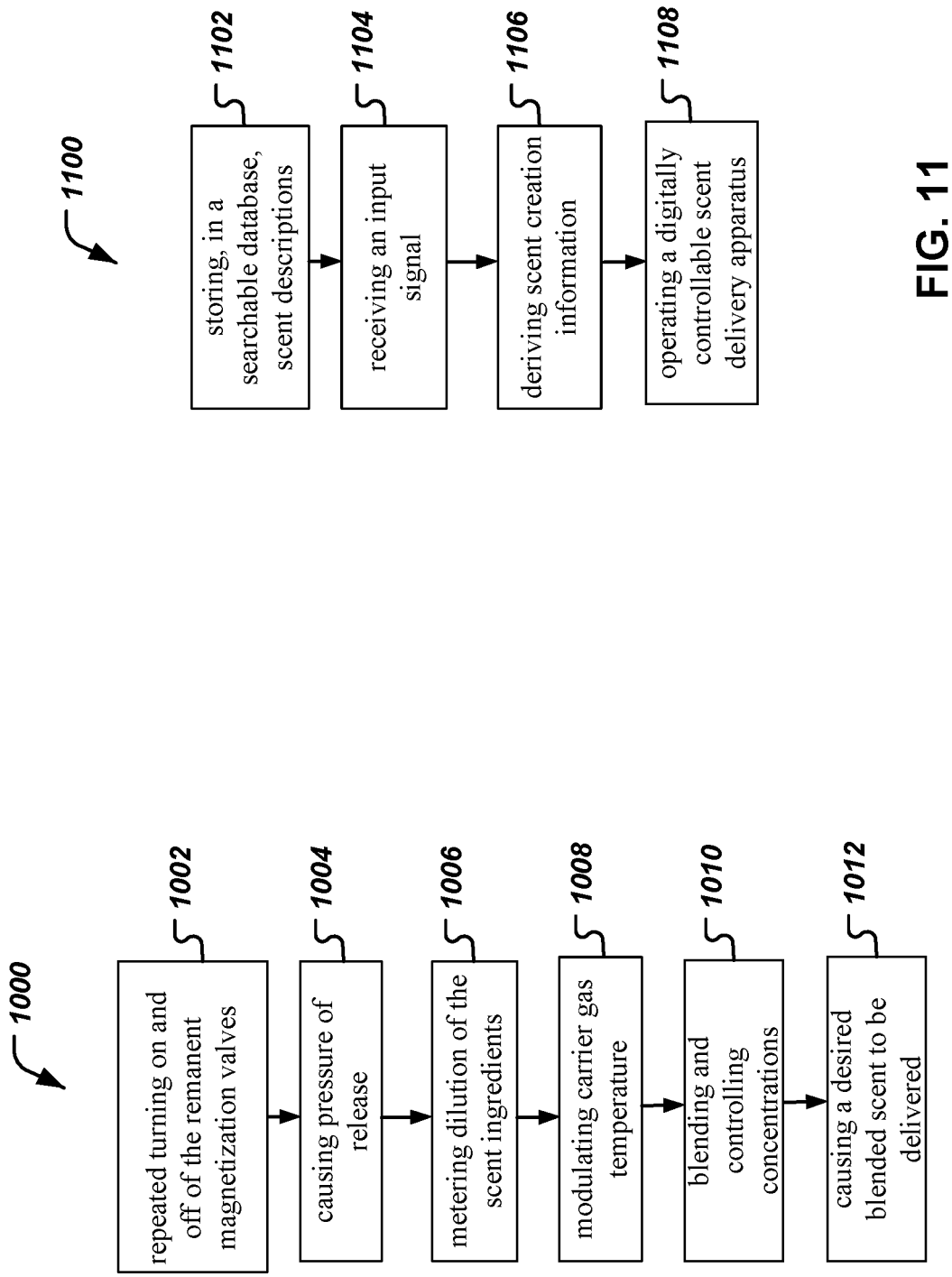

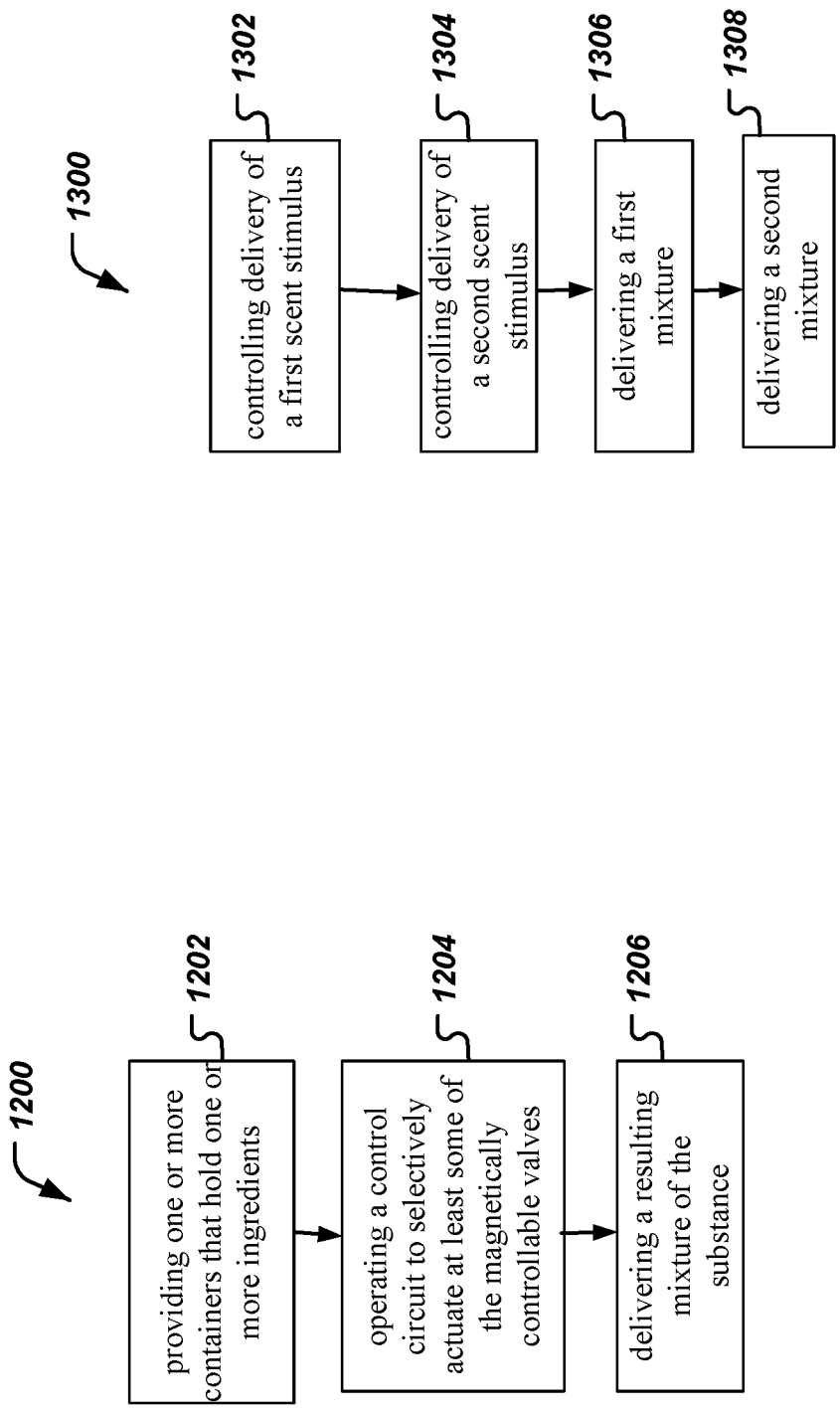

SWITCHABLE DIGITAL SCENT GENERATION AND RELEASE, AND VAPOR AND LIQUID DELIVERY METHODS AND SYSTEMS

CROSS-REFERENCE TO RELATED APPLICATIONS

This patent document is a 371 U.S. National Phase Application of PCT Application No. PCT/US2016/026971, entitled "SWITCHABLE DIGITAL SCENT GENERATION AND RELEASE, AND VAPOR AND LIQUID DELIVERY METHODS AND SYSTEMS" filed on Apr. 11, 2016, which claims the benefit of priority of U.S. Provisional Patent Application No. 62/145,918, entitled "SWITCHABLE SCENT, VAPOR, AND LIQUID RELEASE AND DELIVERY SYSTEMS AND METHODS" filed on Apr. 10, 2015 and U.S. Provisional Patent Application No. 62/174,450, entitled "AUGMENTED SWITCHABLE SUBSTANCE RELEASE AND DELIVERY SYSTEMS" filed on Jun. 11, 2015. The entire contents of the aforementioned patent applications are incorporated by reference as part of the disclosure of this patent document. This application is related to the PCT application by the same inventors, application serial number PCT/US14/035054, entitled "SWITCHABLE GAS AND LIQUID RELEASE AND DELIVERY DEVICES, SYSTEMS, AND METHODS."

TECHNICAL FIELD

This patent document relates to systems, devices, processes and methods for release and delivery of fluids (e.g., gas, vapor, mist, or liquid) and other substances, including without limitation scented fluids.

BACKGROUND

Various technologies have been developed for controlled release of gases, vapors, mists, and liquids with applications for entertainment, education, engineering, advertising, medical treatment and therapy, military, and other purposes. For example, technologies that can provide sensory input to the user or observer such as scent, wind, or mist have been introduced into virtual reality (VR) and augmented reality (AR) applications to provide a more immersive, sensory or realistic experience. Design of scent delivery devices that allow reliable, rapid switching of mixed or unmixed scented gas flux in a repeatable manner by synchronizable, remote actuation could have a significant impact on the effectiveness of the virtual, holographic, mixed reality or augmented reality and live experiences, as well as providing additional benefits for medicinal drug delivery in vaporized, nebulized, atomized, liquid, powder or other form. Rapidly switchable, compact blendable fluid control offers the promise for on-demand synthesis of up to thousands of basic ingredients according to prescribed formulae and has application in a broad array of fields as a research and education tool, a manufacturing or processing method, and commercial as well as consumer products and applications. Furthermore, such devices should offer practical, economic, compact, mechanically and electrically reliable, and efficient on-demand control, and precision-timed gas, vapor, mist, liquid, powders or other substance delivery for effective use by individual users or groups.

SUMMARY

Techniques, systems, and devices are disclosed for rapidly and easily switching the dispensing and delivery of fluids (herein defined as liquids, vapors, mists or gases) and other substances on-demand.

The present technology includes techniques, processes, systems, and devices to provide highly compact, multiple-gated, scented or unscented fluid release and delivery, including rapid switching for on-demand combination and dispensing of such substances. In some implementations, for example, the disclosed techniques, systems, and devices deliver a scented gas into a localized space (e.g., such as the nosespace of an individual), which can add the sense of smell to virtual, mixed or augmented reality or holographic ("VAR") applications such as VAR shopping, simulations, engineering or scientific design, therapy, training, remote education, social interaction and other, interactivity, entertainment or other media.

The subject matter described in this patent document can be implemented in specific ways that provide one or more of the following features. For example, the disclosed technology includes devices that allow convenient, remote, electrically actuatable fluid release based on latchable magnetic switches, piezoelectric, or thermally actuatable switches. For a capability to selectively release one or more of many different types of fluids, X-Y or X-Y-Z matrix operational release systems may also be utilized for the presently disclosed embodiments, similarly as described in the related PCT application PCT/US14/035054.

The disclosed technology is simple and inexpensive, fast to operate, and is capable of miniaturizing delivery apparatuses, processes, systems, and/or mechanisms while maximizing the number of different scented or unscented fluids, or other substances that can be stored, combined, dispensed and cycled or sequenced in an automated fashion or on-demand. The latchable nature of the disclosed devices is very convenient as there is no need to continuously use electricity or power when the delivery system is not activated. Exemplary applications of the present technology include the delivery of a scented gas into a localized space (e.g., such as the nosespace of an individual) as well as switchable release of vapors, mists, powders, or other suspensions for medical drug delivery. Among other things, the technology is highly suited to VAR experiences and entertainment (movies and videogames) and other VAR media, on-line shopping, and/or advertisement of products through online or brick and mortar store display environments.

In one example aspect, a digitally controllable scent creation and delivery apparatus is disclosed. The apparatus includes an array of containers, each container having an inlet through which an input carrier gas flows in, a chamber, called a scent container, for holding a material containing an elementary or a base chemical producing a characteristic odor, called a scent ingredient, or an ingredient, and an outlet through which a mixture of the input gas and the scent ingredient flows out, a flow regulation mechanism that controls gas flow through each container based on electromagnetic signals, one or more blending chambers coupled to outlets of the containers and having a delivery channel outlet, the blending chambers allowing individual outputs from the outlets of the containers to blend together homogeneously to generate a pre-determined scent and flow the pre-determined scent out through the delivery channel outlet, and a pressurization chamber coupled to inlets of the containers, and generating the input carrier gas flows.

In another example aspect, a method of delivering a digitally controlled scent-enhanced multimedia experience is disclosed. The method includes delivering a non-olfactory sensory stimulus such as sound, visual and/or other stimuli to a user, controlling a synchronous delivery of a scent stimulus from a scent device by an electromagnetic control signal that controls scent activation, scent blending, release and delivery to a user, delivering the scent stimulus to the user wherein the scent stimulus is related to the non-olfactory stimulus and enhances, augments, modifies, alters or integrates with user experience of the non-olfactory stimulus, delivering the scent stimulus to the user wherein the scent stimulus is related to the non-olfactory stimulus and the user is engaged with the non-olfactory stimulus passively or actively, or interactively, and selectively delivering the scent stimulus to the user wherein the scent stimulus is related to the non-olfactory stimulus, while the user is engaged in an activity.

These, and other, features and aspects are described in greater detail in the drawings, the description and the claims.

BRIEF DESCRIPTION OF THE DRAWINGS

FIG. 1 (A)-(L) schematically illustrate various embodiments of remanent magnetization valves: (A) remanent magnetization valve with internal mechanical spring based separation of latchable magnetic pin and high permeability ring to allow scented gas penetration; (B) remanent magnetization valve with gas flow spring utilizing pressure-based separation of movable magnetic rod component to allow scent or gas penetration; (C) remanent magnetization valve details showing notched pin guide and high permeability ring; (D) non-cylindrical remanent magnetization valve half-section illustrating flow; (E) remanent magnetization valve with cantilevered spring; (F) remanent magnetization valve with pressure activation; (G) remanent magnetization valve with gravity activation; (H) remanent magnetization with non-cylindrical solenoid; (I) remanent magnetization valve with dual solenoids; (J) a two dimensional assembled 3×8 array of remanent magnetization valves for convenient release of desired scent(s) or other gas/mist/liquid; (K) a two dimensional manufactured 2×2 array of remanent magnetization valves with mating cartridge for convenient release of desired scent(s) or other gas/mist/liquid; and (L) remanent magnetization valve array with two dimensional solenoids for typical lithographic manufacture.

FIG. 3 (A)-(H)) schematically illustrate the blending of fluids (including gases generated from or containing odor/scent generating chemical ingredients) according to combination and parameters specified by formula, or that may be programmed (via internet or other wired or wireless transmission), or manually adjusted for purposes of research and development, testing and experimentation, for on-demand production of unscented or scented compounds ("compounding") for device delivery to individuals or groups (said device hereinafter alternatively referred to as the "digital device"): (A) simultaneously activated/duty-cycled remanent magnetization valves for on-off release of fluids for blending; (B) remotely located ingredient storage containers and delivery via channel to a blending chamber (C) a disk layout of cartridge containers to facilitate rapid fluid blending; (D) alternative disk-type container layouts for rotatable alignment, mirrored, and stacked deployment; (E) a cylindrical layout of cartridge containers to facilitate rapid fluid blending; (F) a nested ring layout of cartridge containers for large capacity-ingredient systems; (G) assisted blending via geometry or agitation; and (H) a latchable remanent magnetization blending/dividing valve.

FIG. 5 (A)-(G) schematically illustrate various embodiments of channel-deposition cleaning procedures for the delivery of multiple chemical fluids or other substances consecutively or simultaneously down a single channel: (A) bundled scent-specific delivery channels for delivery of various chemical fluids or other substances; (B) nonporous residue-resistant single channel which can be used for delivery of different scented gases for a period of time with minimal deposition of scent material residue; (C) deposition cleaning of an internal coating by resistive heating; (D) deposition cleaning of an internal coating by inductive heating; (E) Deposition cleaning by automated or pre-programmed internal chemical purge; (F) Deposition cleaning by electromagnetic shuddering of the channel while undergoing gas flow; and (G) a pre- or intermittent-heating mechanism for cleaning internal system components.

FIG. 6 (A)-(G) schematically illustrate various alternatives for vaporization, atomization, or aerosolization of a liquid solution or suspension: (A) coated or hollow porous micro-/nano-particles optionally with magnetic activation; (B) divided cartridge containers with high surface area scent substrate and replenishing liquid ingredient reservoir; (C)

divided cartridge containers with hollow branched high surface area scent substrate and replenishing liquid ingredient reservoir; (D) dispersing microscale/nanoscale droplets via pressurized distribution of a fluid through a patterned plate with hydrophobic/lipophobic/omniphobic coating on the egress face with droplets being dispersed into a transverse flow of air or other vapor; (E) dispersing microscale/nanoscale droplets via three-dimensional mesh with a hydro-/lipo-/omni-phobic surface which is shaken by mechanical connection to a surrounding piezoelectric material activated in a high frequency range; (F) continuous vaporization of a fluid via micro-/nano-bubbles held separate by nanoscale lengthwise filaments as vapor flows through the liquid containment chamber; and (G) ultra-high concentration scent medium via three-dimensional high surface area porous composite materials including, for example, resins.

FIG. 7 (A)-(I) schematically illustrate various mechanisms for enhanced, comfortable or modified scent delivery perception or experience: (A) a humidifier for the exit stream to prevent irritation during extended use; (B) a modulated heating mechanism to elevate exit stream temperature; (C) a modulated cooling mechanism to reduce exit stream temperature; (D) scent volume control to reduce or increase intensity via cycling, concentration, dilution, or pressurization; (E) a dual or multiple nostril feed for three dimensional scent delivery; (F) various biosensors for active monitoring of and/or responsive feedback to a user's state, or for purposes of dynamic adjustment of scent delivery synchronous with the play of or interactivity with any type of media or user; (G) some examples of programmatic functions for enhanced, interactive or more immersive (including VAR) scent experiences including speech recognition for scent delivery, three-dimensional scent delivery, scent sharing, haptic activated scent delivery, responsive scent adjustments, contextual scent selection and creation; (H) digital exchanges of scent, and creation formulae between users; and (I) breathing pattern or interval recognition and synchronization.

Figures 8, 9:
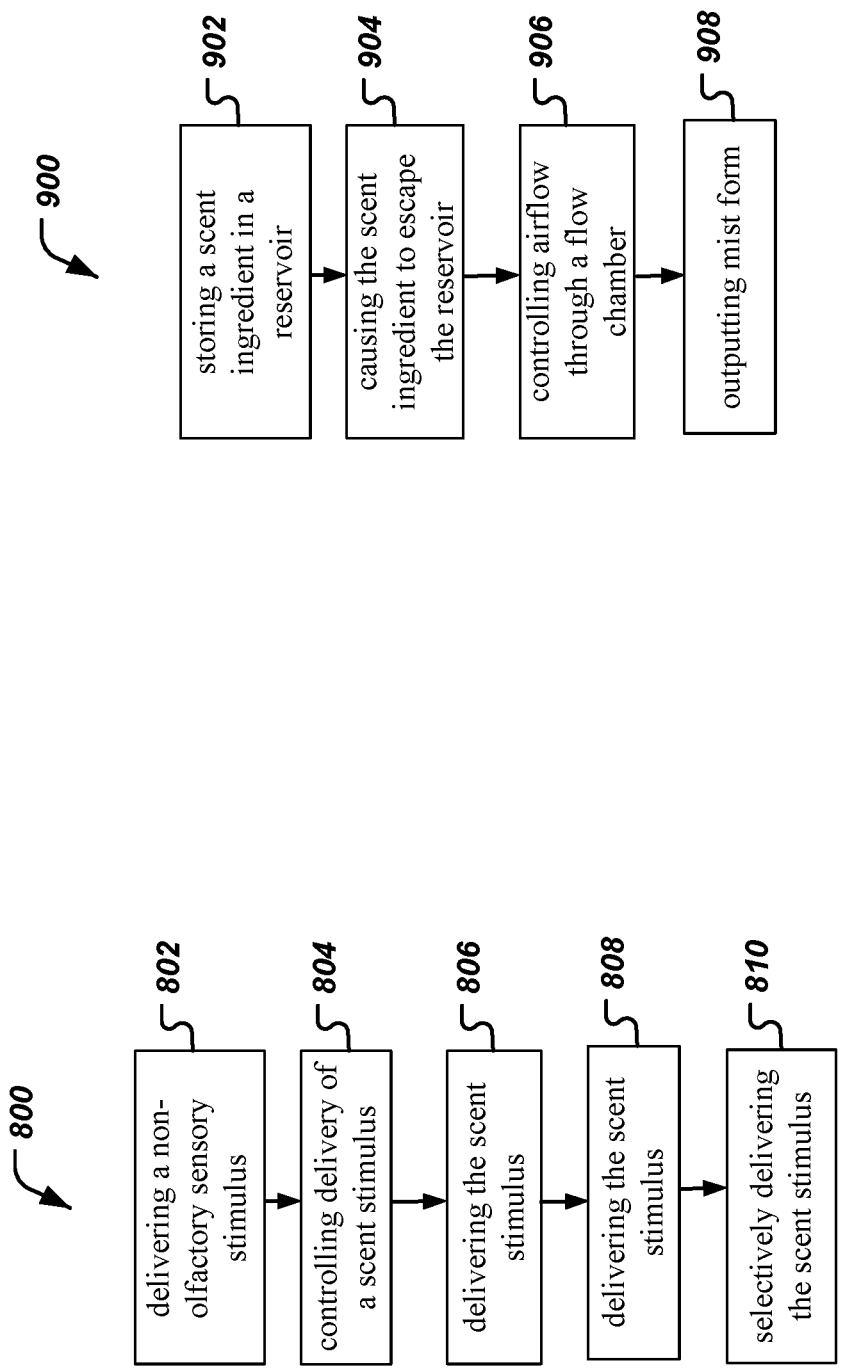

FIG. 8 is a flowchart depiction of an example method for delivering a digitally controlled scent-enhanced multimedia experience.

FIG. 9 is a flowchart illustrating an example method of generating mist of a scent ingredient.

FIG. 10 is a flowchart illustrating an example method of digitally controlling a scent delivery array.

FIG. 11 is a flowchart illustrating an example method of providing a customizable olfactory experience.

FIG. 12 is a flowchart illustrating an example method of delivering a substance to a target site.

FIG. 13 is a flowchart illustrating a method of delivering a digitally controlled scent-enhanced multimedia experience.

DETAILED DESCRIPTION

This document discloses highly scalable techniques, processes, systems and devices for on-demand dispensing and delivery of liquids, mists, vapors or gas. Scent delivery devices of the disclosed technology include convenient, remote, electrically actuatable scent-release components, e.g., based on latchable magnetic, piezoelectric, or thermally actuatable switches and mechanisms. In some implementations, for example, the delivery devices include nanoscale and microscale material structures to control formation and/or delivery of fluids (e.g., such as liquids, vapors, or gases) to produce scented substances. In some implementations, for example, the disclosed technology provides capability to selectively release one or more of many different types of gases or liquids, e.g., using X-Y or X-Y-Z matrix operational release systems. The present technology offers the miniaturization of blending processes and delivery systems while maximizing the number of different basic ingredients (such as scent ingredients) that can be stored, rapidly blended, dispensed, and cycled or sequenced in an automated fashion and/or on demand.

Some aspects and embodiments of the described technology can be understood based on the Detailed Description including various clauses provided, along with the claims, listed in the Claims section.

Applications of the present technology include, but are not limited to, the delivery of a scented gas into a localized space (e.g., such as the nosespace of an individual) that is highly suited, among other things, to VAR experiences and applications and controlled orthonasal or oral drug delivery. In addition to scented gas delivery and orthonasal or oral drug delivery, rapidly switchable and blendable fluid control offers promise for on-demand synthesis applications in a broad array of fields as a research or education tool, manufacturing or processing methods, and commercial and consumer products. Any procedure requiring the precise, rapid, and miniaturizable control of multitudinous fluids either as individual components or blended compositions may benefit from the disclosed devices, systems and methods.

By increasing the potential number of different scents for rapid sequential delivery, e.g., the disclosed scent delivery devices offer the possibility of more complex and sophisticated sensory (olfactory) communication, interactivity, sampling, branding or advertising, as well as greater dramatic possibilities and/or enhanced realism or immersion within a VAR or live experiences. For example, in some cases, the disclosed devices can be used as an olfactory display or as a caller identifier in a mobile phone or other communications device. In other examples, the disclosed devices can be used in conjunction with motion pictures or videogames (e.g., by way of a wide range of multi-scent tracks available for delivery activated synchronously with elements of scenes, actions, actors/characters, music/sound or drama). Other exemplary applications of nano- or micro-device control and on demand delivery of scented fluids include, for example, (a) brick and mortar retail store, online or VAR shopping or advertising; (b) live, online or VAR entertainment, sports, fashion shows, newscasts or any other type of media; (c) exchanges between users or interactivity, (d) user passive or active interaction with any type of media; (e) scented packaging; (f) fragrance-emitting jewelry embedded with the mechanism/device to dispense and cycle different perfumes, selected, set by or reacting to biofeedback of the wearer, in which the mechanism generates an invisible cloud of scent in or around the immediate space near or around the wearer; (g) air fresheners in small, enclosed spaces such as shelving or other furnishings, or that can be attached to fixtures; (h) olfactory branding or signaling; (i) military applications for combat simulations or control or influence of individual behavior; (j) aromatherapy; (k) medical therapy, drug delivery or remote or virtual surgery; (l) hygiene; (m) education; (n) simulations; (o) recorded or live scented media and entertainment; and/or (p) use in multi-sensory apparatuses (e.g. apparatuses combining haptics and scent, scent and taste, haptics-sense-taste, haptics-audio-scent, etc.) providing behavioral, neurological, multi-modal (combined scent, taste, feel, visual, and/or sound) effects, among other applications.

The disclosed technology provides several advantages. One exemplary advantage of the present technology is the versatile design using a simplified valve-containing dispensing or valveless dispensing that allows the choice of chemicals in a blended fluid (such as scented fluids) on-demand. Such designs include exemplary 'latchable-switch gating' mechanisms of the disclosed technology. For example, these exemplary gating mechanisms not only replace the need for complicated mechanical valves, but also minimize the electrical input necessary to control the gating, and are also scalable to small dimensions, e.g., including on a millimeter or less than millimeter scale, thereby adding to the reduction in size and weight (and portability or wearability) of a device or apparatus embodying the technology.

Some existing systems utilize a valveless system capable of dispensing small volumes of scents into a localized space, however, the technical requirements of the dimensions of the delivery channel diameters or lengths are, in themselves, limiting. An advantage of the present technology is that there are no such limitations. Some other existing systems that use a valveless technology employ a primary method of evaporating and dispensing a scented gas via a heating element whose time required to create a required volume of scented gas is comparatively disadvantaged to the present technology whose mechanisms enable the more rapid on-off control, generation and delivery of a scented gas to a user. These and other existing scent generating devices also have limitations in terms of speed, physical dimension and miniaturization, selectivity, and durability. Also, existing technologies currently employed to selectively release fluid (including scented gas) into a localized space, or nosespace, are limited by the number of different scents (or the number of ingredients specified by formulae for their creation) that are capable of being cycled or sequenced, timed and controlled for on-demand precision delivery. By way of more specific example, machines that have scalable multi-scenting capability and precision timed control and delivery of scented gas into a nosespace (or to the nose) such as olfactomers are relatively large in size and are not as reducible in size and form factor for wearability or portability as the present technology. By way of further example, prior art devices that have multi-scenting scent synthesis capability are limited by the number of chemical ingredients that can be synthesized, and therefore, the specificity, range and quality of a catalogue of scents that can be created.

The disclosed technology can also include the use of 'ambient diffusion' technology, which, for example, generates a scented or unscented gas at ambient or room temperature without the use of heating as a primary mechanism to evaporate chemical elements of a fluid, paste, resin, encapsulated, semi-solid or solid material. Delivery of evaporated scent via the present technology also obviates the inherent chemical deposition, lingering duration in the air, and other disadvantages and risks in delivering atomized chemicals (including, for example, scented mist) at close range to an individual. Ambient diffusion also avoids certain limitations or drawbacks associated with using heating as the primary mechanism to evaporate a scented or unscented liquid or other scent or unscented medium, including, for example, the energy required to achieve fast evaporation for rapid gas formation and delivery, and the potential to, in the case of scent, potentially (undesirably) alter the properties or behavior of the scent-generating chemical components by heating.

Other primary mechanisms for generating an evaporated (e.g., completely evaporated) scented gas can include the passage of gas on the surface of a scented solvent or other material, or through a porous solid, gel or other scented substance. In the present technology, for example in one embodiment, microbubbles of gas are created and pumped through an oil or other solvent containing scented material and generating a scented gas upon exit at the surface of the solvent or oil. The use of microbubbles in such a way maximizes the potential for large surface area contact of air (or gas) within the scented solvent or oil, thereby increasing potential diffusion, and as a result reducing the time necessary to deliver a desired volume of scented gas, or having the effect to increase the concentration of targeted chemical molecules released in the carrier gas.

In the presently disclosed technology, by way of further example, in another embodiment an ultra-high surface area substrate created by micro or nano-branching of substrate material may be placed within the scent or liquid containing chamber or within the replaceable cartridge. Such a nanostructured substrate material is coated with scented solvent to hold the solvent in place without having to introduce additional mechanical fixturing to prevent leakage of the liquid material from the chamber or cartridge, and also reduces, because of the large surface area, the amount of scented liquid necessary to produce required scent concentrations per given time, thereby helping to reduce the size and weight of the device to enable wearability. The desired large surface area of such nanostructured substrate material, such as made of ceramic, metallic, polymer or carbon material, is at least 300 meter square per gram, preferably at least 1,000 meter square per gram, preferably at least 2,000 meter square per gram, as measured by Brunauer-Emmett-Teller (BET) analysis technique of gas adsorption.

Most examples of existing selective scent releasing and delivery systems introduced to-date are limited by either ineffective control, lack of precision timing deliverable to the intended target, unwanted mix of scents during sequenced delivery, lingering scent in the environment, the mechanical reliability, energy efficiency and/or the cost and size of the delivery apparatus. Diffusion of a large volume of scent into a large area is comparatively difficult to quickly clear from the air (or dissipate), thereby limiting the rapidity with which a succeeding scent can be delivered 'cleanly' to individuals within the space. For entertainment applications, for example, in many instances scented air is released into the general space of a theater via the ventilation system or fans, or in and around seating. Such conventional delivery mechanisms have limited or no multiplexing (scent switching) capabilities or capacity, nor can they provide as rapid scent or efficient delivery capability precision-timed to the nosespaces of individuals as the present technology. Examples of existing systems that can release scent within seating area include the Sensorama game system from which a scent is released from the chair according to the displayed scene and the steering wheel can provide mechanical vibrations. In movies such as those in the AMLUX theatre, scents were released in conjunction with visual images. Scent release by evaporating or spraying a scented material has been utilized for the training of fire-fighters and scent-emitting collars have been employed for the training of soldiers. However, many of these known approaches are impractical, operationally unreliable, or limited in their capacity for precision-timed, multiplexing scent delivery. Therefore, there is a need for a reliable scent release and delivery system having rapidly switchable, automated and/or remote, actuatable and multi-cycle durable characteristics, that incorporate x-y or x-y-z matrix operational systems enabling controlled, timed scent release from many different sources of scents (with a minimal number of controlling mechanisms).

Section headings are used in the present document to facilitate readability and do not limit the scope of the disclosed technology in any way.

Examples of Remanent Magnetization Valve Configurations and Methods for Active Fluid Release Referring to the drawings, FIG. 1(A) to FIG. 1(L) schematically illustrate various embodiments of a remanent magnetization valve with pin guide, magnetically latchable and movable pin, high permeability mating ring or plate, solenoid/s, and electromagnetic shield. Magnetization of the pin is accomplished with a pulse signal to the solenoid upon which the pin snaps against the ring creating a seal. Demagnetization is accomplished by a diminishing AC signal to the solenoid, an oppositely directed and diminished field produced by a single or series of DC signals, or a secondary solenoid producing an oppositely oriented magnetic field. The magnetic shield may be useful in shielding neighboring valves from being affected by each other's solenoid magnetization.

For the latchable magnetic pin material, various square-loop magnetic materials can be utilized. For the desired geometry of rod or pin shape, mechanically ductile alloys that can easily be swaged, rod drawn or wire drawn into such a geometry are preferred. An example is to use Fe—Cr—Co based spinodally decomposing magnet alloys such as Fe-33% Cr-7% Co-2% Cu (in weight %), which is first heat treated to spinodally decompose into a two-phase structure, and is then deformation-aged or magnetic-field-aged so as to produce a square-loop magnetic properties. The composition of the alloy can be in the range of 25-40% Cr, 5-15% Co, 0-4% Cu, with the balance Fe. Other alloying elements not exceeding 10 weight % may also be added. See an article by S. Jin, "Deformation-Induced Anisotropic Cr—Co—Fe Permanent Magnet Alloys", IEEE Trans. Magnetics, MAG-15, 1748 (1979), and an article by S. Jin and N. V. Gayle, "Low Cobalt Cr—Co—Fe Magnet Alloys by Slow Cooling Under Magnetic Field", IEEE Trans. Magnetics, MAG-16, 526 (1980), which are incorporated by reference in their entirety herein. The magnetic properties of a magnetic material can be described by several parameters, e.g., including a saturation magnetization (Bs) that indicates the highest possible magnetization value in the given material, the remanent magnetization (Br) that indicates the remaining magnetization value after the applied field is removed to zero field, and the coercive force (Hc) which is an indication of a required external applied magnetic field that needs to be applied to reduce/force the magnetization of the material to zero, which indicates how hard or soft the magnetic material is.

According to some embodiments, these types of magnetic alloys are specifically processed to exhibit high remanent magnetization with square loop shape, yet processed to exhibit a specific magnetic coercive force so as to easily enable switch applications for fluid delivery (including scent delivery) devices. The final aging heat treatment temperature and time is to be controlled so that the magnetic coercive force (Hc) is desirably within a specific range of 30-300 Oe, preferably in the range of 50-200 Oe, and more preferably in the range of 80-130 Oe.

Other spinodally decomposing alloys such as Cu—Ni—Fe or Cu—Ni—Co may also be used to obtain highly square loop magnetic alloys. Highly uniaxially deformed ductile magnetic alloys, with an option of pre-decomposition into two-phase structure, may also be utilized, such as Fe—Ni—Mn, Fe—Mo—Ni, Fe—Cr—Mo alloys, which upon uniaxial plastic deformation, can provide Hc values of 50-150 Oe.

The high magnetic permeability material in FIG. 1(A)-1(L), which is the mating magnetic material below can be a soft magnet (e.g., a Permalloy, for example, having 80% Ni-20% Fe in weight % or 45% Ni-55% Fe, or a silicon steel, or other alloys having similar soft magnetic properties), a semi-hard magnet (e.g., Fe—Cr, Fe—Ni, and other magnetic alloys), or a permanent magnet (e.g., Fe—Cr—Co, Vicalloy, Sm—Co coated cantilever). In FIG. 1, soft magnetic alloy of 45% Ni-55% Fe alloy is utilized.

Referring to the drawings, FIG. 1 schematically shows (A) remanent magnetization valve with internal mechanical spring, and (B) remanent magnetization valve with gas flow spring utilizing pressure-based separation of movable magnetic rod component to allow scent or gas penetration. For the remanent magnetization valve with an internal mechanical spring illustrated in FIG. 1 (A), in closed state (116), magnetized latchable pin 104 above snaps against high permeability material 110 below creating a seal while overcoming the slight spring force that previously kept the switch open. To open the switch, the pin is demagnetized (e.g., by using a 60 Hz demagnetizing cycle in a solenoid with gradually diminishing magnetic field, or by applying an opposite magnetic field which on removing the magnetic field enables recoiling of magnetization state to near zero). The internal spring in FIG. 1 (A) aids in separation by pushing back up the upper magnetic rod (or a magnetic pin).

For the remanent magnetization valve with gas flow spring utilizing pressure-based separation, as illustrated in FIG. 1 (B), in the closed state, a magnetized latchable pin snaps against high permeability material creating a seal. To open, the pin is demagnetized and gas pressure spring aids in separation. The unique nature of this FIG. 1 (B) switch structure is that no mechanical spring is used, and instead, upward gas flow (which is needed anyway for scent release and delivery) is simultaneously utilized as a lifting force to keep the magnetic switch open for a desired duration to continue delivery of the gas. The device structure is thus more advantageous and simpler as compared to the FIG. 1 (A) structure, although the latter is still useful for certain designs and applications.

FIG. 1 (C) illustrates an additional application of the devices/systems for latchably releasing drugs in the form of gas, vapor, mist, powder or suspension near or inside the nostrils for drug absorption via orthonasal delivery. Similarly, as in FIG. 1(A), the switch in a passive closed state with magnetized pin sealed against high permeability material blocks the through-hole and stops the flow of the drug to be administered. In the "OPEN" state, the latchable magnetic pin is demagnetized by either a gradually diminishing magnetic field or a certain opposite magnetic field strength (from the surrounding solenoid/s) and is moved away from the high permeability material, thus revealing through-hole for drug mist or vapor flow.

In addition to controlling gas flow, miniaturized remanent magnetization valves may also be used for controlled drug release, in a handheld, stationary or wearable configuration where the gas-state, vapor-state or mist-state drug doses are administered to a patient (or a customer) on schedule or as programmed by control software. Hardwire connected actuations as well as wireless activations are possible. The end of a device can be preferably configured so that there is a protruding end tube section into the nostrils (similar as the oxygen gas supply apparatus for hospital patients) so as to maximally direct and utilize the released amount of mist, vapor/gas, or suspension drug.

FIG. 1 (D) illustrates the use of a non-cylindrical interior pin guide to permit fluid flow around the pin when in the open state. This guide is depicted as triangular but may also be rectangular, pentagonal, hexagonal, etc. Seal is achieved by mating two polished surfaces from the latchable pin and the high permeability ring. Alternatively, a thin compliant seal can be placed between the pin and ring, if necessary to promote a tighter seal. In some embodiments, the gap around the interior pin guide and the external casing may be radially symmetrical (when seen in a cross sectional view). One advantage of such a symmetry is to allow uniform passage of the flow around the housing.

Various methods may be used to separate the ring and pin upon demagnetization. FIG. 1 (E) accomplishes separation with a cantilevered spring which pushes against the pin. The spring properties are specifically chosen to allow for sealing upon magnetization when attracting forces between the pin and ring overcome the spring force of the cantilever and separation upon demagnetization when the spring force overcomes and gravitational or trace attraction remaining.

Alternatively, in FIG. 1 (F) the remanent magnetization valve utilizes pressure-based separation. In the closed state, the magnetized latchable pin snaps against high permeability material creating a seal. To open, the pin is demagnetized and fluid pressure aids in separation. The unique nature of this FIG. 1 (F) switch structure is that no mechanical spring is used, and instead, upward fluid flow (which is needed anyway for release and delivery of fluid) is simultaneously utilized as a separating force to keep the magnetic switch open for a desired duration to continue delivery of the fluid. The device structure is thus more advantageous and simpler as compared to the FIG. 1 (E) structure, although the latter is still useful for certain designs and applications.

Another spring-less configuration is depicted in FIG. 1 (G) which utilizes gravitational forces on the movable pin to effect pin-ring separation. This design is similarly convenient in not requiring a spring for separation but is limited to a narrow range of valve orientations as gravitational forces must work to separate the latchable pin upon demagnetization. As such, a gravitationally aided design is more suitable for fixed position applications such as tabletop or wall-based release. FIG. 1 (H) further simplifies and miniaturizes the remanent magnetization valve concept of FIG. 1 (A)-(G) by combining a non-cylindrical pin-guide and the magnetization/demagnetization solenoid. The figure portrays a triangular solenoid configuration, however, any non-cylindrical shape which maintains the cross-plane pin positioning would work similarly. Opening and closing mechanisms for the valve are as described in the earlier figures. One other advantage of combining the pin guide and the solenoid come in terms of efficiency. By locating the solenoid walls nearer to the pin, magnetic field strength increases for the same power level during magnetization and demagnetization.

In addition to the single solenoid configuration depicted in FIG. 1 (A)-(H), a dual solenoid configuration may be used with each solenoid taking separate responsibilities as depicted in FIG. 1 (I). The coil nearest to the high permeability plate or ring magnetizes the pin upon activation, closing the valve which then remains closed due to the remanent magnetization of the pin material. The $2^{nd}$ solenoid produces a magnetic field in the opposite direction and with a lower magnitude due to the transverse distance thereby opening the valve and canceling out the remanent magnetization in the pin. This configuration has the added benefit of forcefully opening the valve during demagnetization as the pin moves towards the center of the $2^{nd}$ coil. The other opening mechanisms (spring, pressure, gravitational) are therefore less necessary for a dual coil configuration. In one advantageous aspect, the use of dual solenoids for magnetization/demagnetization enables savings in hardware by simplifying the current feeding circuitry and also may increase longevity and reliability by using electromagnetic force both for opening and for closing the valve. In some embodiments, taking into account magnetic hysteresis of the material, multiple magnetization-demagnetization cycles may be rapidly applied (e.g., 60 Hz frequency) in a gradually diminishing field manner to precisely control the opening and closing of the valves.

FIG. 1 (J) illustrates a two dimensional array of magnetically latchable switches for convenient release of desired scented or unscented gas/mist/liquid. In some embodiments, a two dimensional array of magnetically latchable switches for convenient generation and release of desired selected scents or other fluids may be used. An example 3×8 array of containers containing 24 scent ingredients used for blending is described. The desired scent ingredient(s) may be controllably selected in any desired or programmed combination. In closed state, magnetized latchable pins snap against Permalloy plate (size-matching hole or rod) to create a tight seal (possibly with intervening elastomer or other type material). To open, a selected pin is demagnetized and pressure, mechanical spring, or gravity aids in separation. Cylindrical pins are held in place by non-circular (square, triangular, or other) pin guides, thus permitting some gas flow around the pin edges when pin is pushed back from seal against Permalloy. For scented gas generation and flow release, gas flow is pushed through an optionally removable/replaceable cartridge located adjacent to the remanent magnetization switch array and then loaded gas is delivered through check valves to the scent outlets. The valves positioned in the array (e.g., 10×10 or 8×20, etc.) can be programmably and selectively actuated (just one valve only, or optionally two or more valves activated simultaneously for combination and blending of fluids (for example, including scented and/or unscented gases) by wireless or hard wired signals with compatible software, so that a particular device is magnetized or demagnetized, and fluid flow is initiated or stopped. Singular valves may be activated for individual fluid delivery or multiple valves activated simultaneously or in concert for blending/coupling of scent ingredients.

Referring to FIG. 1 (K), some embodiments also include a two dimensional array of magnetically latchable switches for convenient release of desired fluid, including scented gas(es) or unscented gas/mist/liquid. An example 2×2 array of containers, each containing one of four scent ingredients in liquid, semi-solid or solid state is described. The desired or selected scent(s) may be controllably released as shown in cutaway view of FIG. 1 (K). In closed state, magnetized latchable pins snap against Permalloy plate (size-matching hole or rod) to compress a compliant material between the latchable magnet rod and the corresponding Permalloy plate hole (or rod), creating a tight seal. To open, a selected pin is demagnetized and gas pressure through the plate aids in separation. Cylindrical pins are held in place by non-circular (square, triangular, or other) pin guides, thus permitting some gas to flow around the pin edges when pin is pushed back from seal against Permalloy. For scent release, gas flow is pushed through an optionally removable/replaceable cartridge containing an array of scent ingredient containers (a "scent cartridge") located adjacent to the remanent magnetization switch array (positioned above the magnetic pin in the case of FIG. 1 (K) configuration) and then scented gas is delivered through check valves to the scent outlets. The valves positioned in the array (e.g., 10×10 or 8×20, etc.) can be programmably and selectively actuated (just one valve only, or optionally two or more valves activated simultaneously to generate scented gas) by wireless signals or hard wired signals with compatible software, so that a particular device is magnetized or demagnetized, and gas flow is initiated or stopped. Scent generation can be programmably actuated by wireless signals or wired signals from any communications or media device with suitable software, for example, from a cell phone, TV remote control, laptop computer, VAR device, or any internet connected or wireless device. Such a portable or hand-held scent release device can optionally hold up to many hundreds of ready-made scents. Singular valves may be activated for individual scent delivery or multiple valves activated simultaneously or in concert for blending/coupling of ingredients.

To avoid time-consuming and complicated winding procedures during manufacture, miniaturized valve arrays may utilize flat spiral solenoids as in FIG. 1 (L) located on substrates enclosing the remanent magnetization pins within non-cylindrical pin-guides. The lower solenoids producing a field to close the valves against a high-permeability through-hole via acting dually as an electrical connection to the solenoid coil. Valves may be opened with an oppositely directed but diminished DC field to remove remanent magnetization in the pin, a diminishing AC field, or an optional second solenoid at the rear of the pin to form a dual coil configuration as in FIG. 1 (I). Substrate arrays may be manufactured in parallel with familiar lithographic and etching processes with potentially many hundreds or thousands of valves being produced in parallel. A cartridge containing scent ingredients may be located adjacent to the valve array for selective activation. Singular valves may be activated for individual scent delivery or multiple valves activated simultaneously or in concert for blending/coupling of ingredients.

For optimization and viable industrial applications of scent delivery systems, i) miniaturization of the size, ii) rapid switching speed of operation and iii) low power usage, are important parameters that also need to be considered.

Miniaturization of the flow regulation mechanisms is useful in order to construct scent delivery devices which may be built into or affixed to existing cell phones, tablets, virtual reality head mounted displays, televisions, laptops, computers, wearable technologies, etc. The number of individual flow regulation mechanisms to control scent ingredients may be, for example, at least 10, more likely at least 100, and even more likely at least 1000; therefore, the remanent magnetization valves which regulate scent release as described herein, could have a miniaturized dimension: a diameter desirably less than 4 mm, preferable less than 2 mm, and even more preferably less than 1 mm; a length desirably less than 10 mm, preferably less than 5 mm, and even more preferably less than 2 mm; and a weight desirably less than 200 mg, preferably less than 25 mg, and even more preferably less than 5 mg.

Rapid switching when both opening and closing of the flow regulation mechanisms is useful to the present scent delivery device in order to synchronize scent release promptly to visually displayed content, advertisements, gameplay, audio, messaging, etc. Rapid switching is also useful to the blending of scent ingredients in precise ratios by timed on-off activation of scent containers. In the case of a scent cartridge positioned proximate to a user's nosespace, the duration from a scent activation to ultimate release into the nosespace, for example, is desirably less than 500 ms, preferably less than 200 ms, and even more preferably less than 100 ms; therefore, the remanent magnetization valves which regulate scent release according to embodiments described herein have a switching speed for both closing and for opening of less than 100 ms, preferably less than 10 ms, and even more preferably less than 1 ms.

Low power and energy consumption of the flow regulation mechanisms is useful in order to construct scent delivery devices which may be powered by batteries such as those of a cell phone, tablet, laptop, virtual reality device, or similar. The number of individual switching events which may occur in the course of using a scent delivery device for a multimedia experience may be, for example, at least 10 per minute, more likely at least 50 per minute, and in the case of blending even more likely at least 250 per minute; therefore, the remanent magnetization valves which regulate scent release according to the present document have a minimal power and energy consumption: a switching power desirably of less than 2.5 W, preferably less than 500 mW, and even more preferably less than 100 mW; and an energy required per switch desirably less than 250 mJ, preferably less than 5 mJ, and even more preferably less than 0.1 mJ.

The miniaturized size, high speed of operation and low power requirements allow the switchable scent storage and delivery device according to the invention to be compact and easily usable, for example, into a USB device (or an associated device connectable to USB) that can simply be plugged into a computer, notepad or cell phone for easy release of some scents for online shopping or playing videogames.

EXAMPLE DEVICES

Various aspects of the disclosed embodiments and techniques have been reduced to practice in the following examples.

Example 1

A scent delivery device prototype has been constructed for electronically activated, selective delivery of six scents: the aroma of campfire, grass, lemon, perfume, baby powder, and fresh linen. The device comprised six magnetically latchable switch structures, each coupled with a pressurization device and coupled at their outlet with individuated ingredient containers containing a source scent material. Each magnetically latchable switch structure permits electronically activated gas flow thereby permitting the passage of gas from the containers and the ultimate delivery of scented gas. The electrical current through the solenoid surrounding the device may serve to magnetize or demagnetize the magnetic pin, which opens or closes the pathway for the scented gas. The device can be handheld or suspended from the user's neck. Activation is controlled via USB connection of the device to a computer. Upon scent activation, electronic signals activate one or more selected latchable switches initiating the flow of scented gas. After exiting the container, the mixture of scent ingredient and air is then transported via flexible tube to a headset anchored near the user's ear which may optionally be used in conjunction with a VR head-mounted display, through a positionally adjustable armature which releases the scent into the user's nose-space. Scent delivery is accomplished within 300 milliseconds. The person wearing the headset clearly senses and distinguishes each of the released scents of campfire, grass, lemon, perfume, baby powder, or fresh linen when electronically activated by switch-on command. The scent release operation was repeated at least 20 times with reproducible results.

Example 2 is a scent delivery device with four scent capacity to deliver aromas of bubblegum, orange, apple cinnamon, or perfume. The device comprised eight miniature sized, magnetically latchable switch structures, four of which are coupled with the inlet of four scent ingredient containers holding source scent materials, while the other four switch structures are coupled with the outlets of the four scent ingredient containers with outlets releasing into free air. Each magnetically latchable switch structure permits electronically activated gas flow through the air-spring separation between the magnetic pin and the seating structure. The magnetic alloy pin heat treated to have a square hysteresis loop, with a remanent magnetization to saturation magnetization ratio of at least 0.90 is controlled by copper solenoid surrounding the pin such that an electrical current through the solenoid may serve to magnetize or demagnetize the pin. The ingredient container cartridges house individual ready-made scent materials Device activation is controlled via USB connection to a computer. Upon scent activation, electronic signals open the valves at both the inlet and outlet of one or more scent containers initiating airflow and scent vapor flow. Scent delivery is accomplished within 500 milliseconds and delivered scents include the aroma of bubblegum, orange, apple cinnamon, and perfume. A human nose situated within 30 centimeters of the device can clearly sense and distinguish each of the released scents at the moment of its release. This scenting operation was repeated at least 50 times with reproducible detection by human olfaction.

Example 3 is a scent delivery device for affixation to commercially available VR headsets including those from the Oculus Rift, HTC Vive, Sony PlayStation VR, Samsung Gear VR, Google Cardboard, or similar. For the scent release device, eight magnetically latchable switch structures were coupled with a removable/replaceable cartridge of eight scent containers. Each magnetically latchable switch structure permits electronically activated gas flow separation (spring-less) between the magnetic pin and the seating structure. The magnetic alloy pin is heat treated to have a square hysteresis loop, with a remanent magnetization to saturation magnetization ratio of at least 0.90. The pin is contained within a non-cylindrical plastic guide around which two solenoids are wound corresponding to the pin such that an electrical current may serve to magnetize the pin and close the valve or serve to demagnetize the pin. The ingredient containers house individual ready-made or chemical component scent materials. All device components were assembled into a single housing which was mounted centrally to the front underside of a VR/AR headset. Electronic activation of the scent release device is controlled and powered via USB connection. Upon scent activation, electronic signals activate and initiate airflow, also optionally through a magnetic check valve at the inlet of the scent ingredient container. Scent delivery through the nose-piece positioned the front underside of a VR/AR headset is accomplished within 100 milliseconds and delivered scents include the aroma of blood, rainforest, and dinosaur breath among others. The person wearing the virtual reality (VR) gear over his head, which was equipped with the disclosed scent release device clearly sensed and distinguished each of the scents synchronously released with corresponding visual VR content.

Examples of Magnetic Check Valve Configurations and Methods for Passive Gas Release For a functional gas delivery device, it is important to seal an ingredient container adequately when the ingredient is not in use. It is possible to accomplish this by placing a remanent magnetization valve at both the inlet and exit of the container. However, the system is simplified by replacing the outlet valve with a check valve which only opens when the associated inlet remanent magnetization valve is opened. Doing so halves the number of control circuits necessary for the valves, simplifies production, and may allow for disposable/recyclable cartridges with built in check valves which would often not be feasible with remanent magnetization valves as built in components.

FIG. 2 (A) schematically depicts a check valve consisting of a magnetic ring which mates with a magnetically susceptible flap attached by a single tab to the upper surface of the ring. The cracking pressure for this valve is simply the gas pressure which balances the magnetic attractive force between the flap and the ring. When a paired remanent magnetization valve opens and permits flow and high pressure to reach the adjacent check valve, the valve flexes open at the tabbed hinge and permits scent to escape the container. Upon closing the remanent magnetization valve, pressure drops again and the magnetic attractive force again overwhelms the pressure differential, closing the check valve and sealing the container. The balance of the magnetic force and pressure force may be adjusted substantially by changing the materials, the magnetic ring's dimensions, the flap's dimensions, and the distance between flap and ring via sealant inserts. Optionally, flap and ring surfaces can be coated with a hydrophobic and/or lipophobic material/texture or smooth metal/ceramic layer deposition and plating that prevents or minimizes scent accumulations/contaminations.

Likewise, FIG. 2 (B) schematically depicts a check valve consisting of a magnetic flap which mates with a magnetically susceptible ring attached by a single tab to the upper surface of the ring. The cracking pressure for this valve is simply the gas pressure which balances the magnetic attractive force between the flap and the ring. When a paired remanent magnetization valve opens and permits flow and high pressure to reach the adjacent check valve, the valve flexes open at the tabbed hinge and permits scent to escape the container. Upon closing the remanent magnetization valve, pressure drops again and the magnetic attractive force again overwhelms the pressure differential, closing the check valve and sealing the container. The balance of the magnetic force and pressure force may be adjusted substantially by changing the materials, the magnetic ring's dimensions, the flap's dimensions, and the distance between flap and ring via sealant inserts. Optionally, flap and ring surfaces can be coated with a hydrophobic and/or lipophobic material/texture or smooth metal/ceramic layer deposition and plating that prevents or minimizes scent accumulations/contaminations.

In an array, magnetic check valves with either magnetized ring or flap, the valve opening depends entirely on the backside pressure buildup as shown in FIG. 2 (C). Only the valve with overpowering backside pressure will open with the remainder continuing to seal their respective containers. Check valve arrays may be manufactured in bulk simply by applying successive layers of magnetized, compliant, and magnetically susceptible materials with sufficiently positioned through-holes and punched out perimeters (excepting a single hinge tab). Optionally, flap and ring surfaces can be coated with a hydrophobic and/or lipophobic material/texture or smooth metal/ceramic layer deposition and plating that prevents or minimizes scent accumulations/contaminations.

Figure 2B:
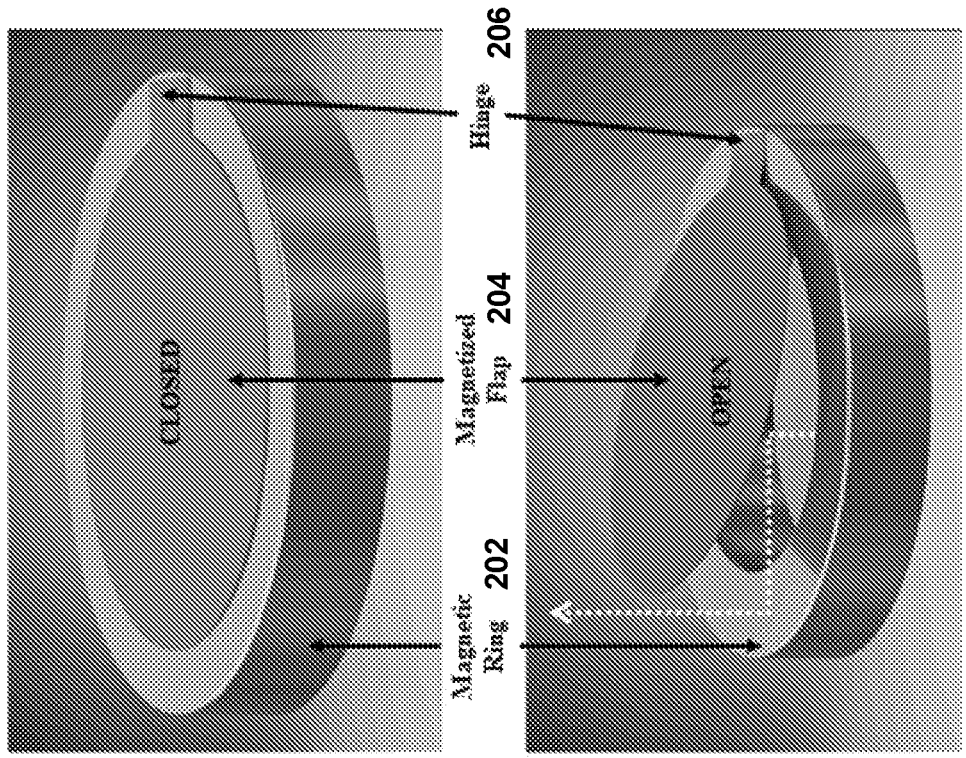
FIG. 2 (A)-(C) schematically illustrated various embodiments of a magnetic check valve: (A) check valve with magnetic ring; (B) check valve with magnetic flap; and (C) an array of simultaneously produced check valves.
Figure 2A:
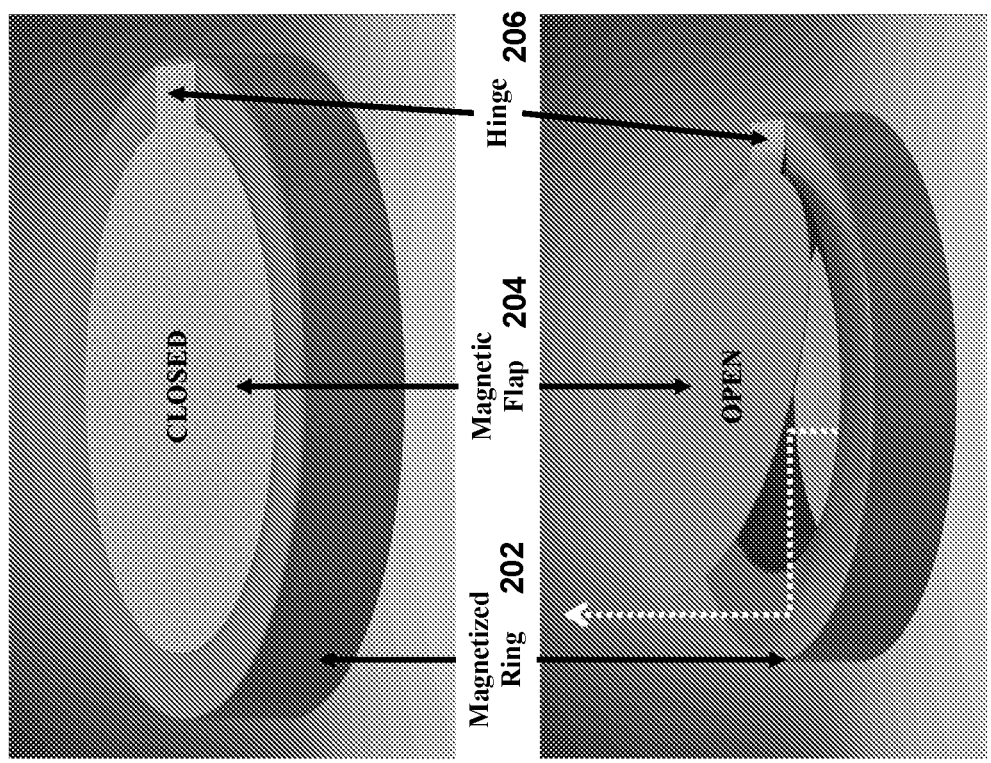
Figure 2C:
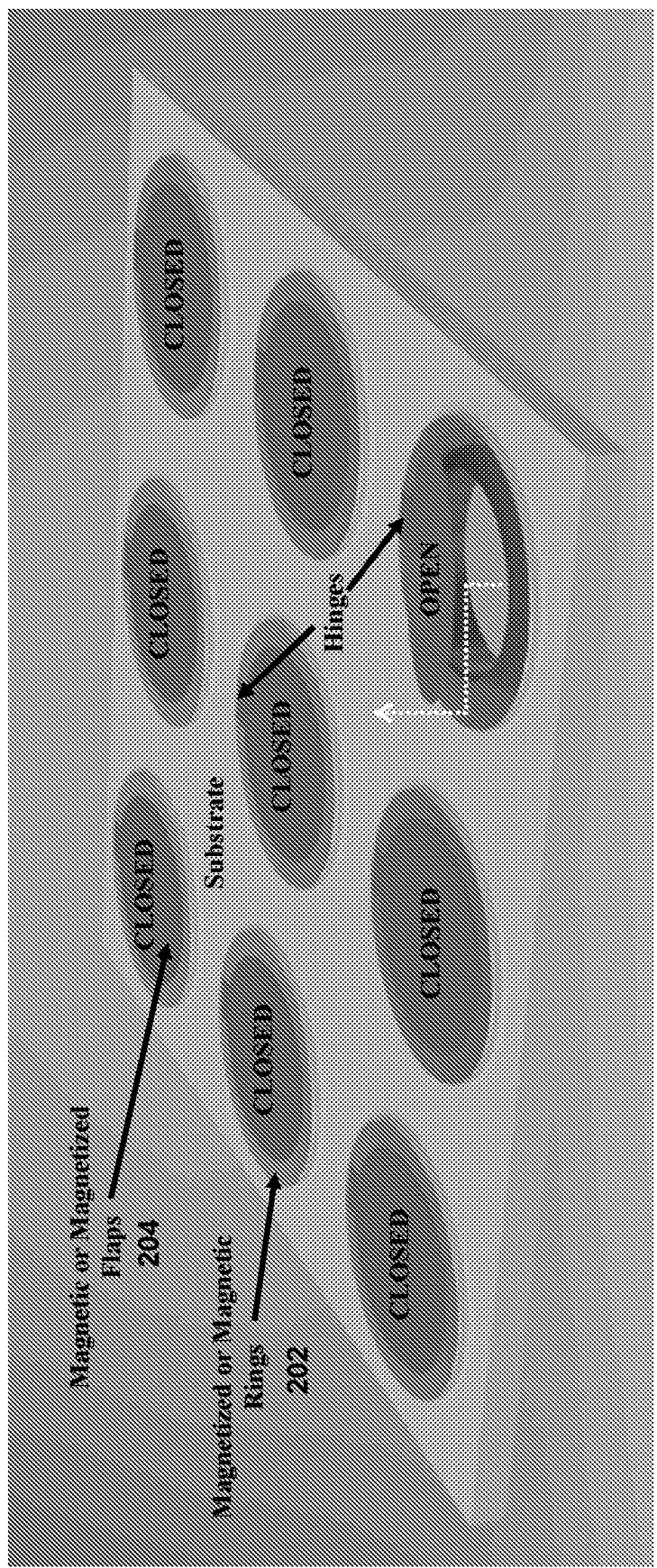

In the embodiment of a scalable check valve array depicted in FIG. 2(C), opening is accomplished by pressure forces overcoming the magnetic attraction force between the flap and the magnetized ring. Check valve activation is passive and so may be paired with an active valve, such as a remanent magnetization valve, to selectively open a single valve in an array of check valves. Optionally, flap and ring surfaces can be coated with a hydrophobic and/or lipophobic material or texture or smooth metallic or ceramic layer deposition and plating that prevents or minimizes scent accumulation and contamination.

Examples of Combinatorial Fluid Production and Fluid Compounds

While many ready-made (pre-prepared) fragrance, or flavor substances (either referred to as "scent") can be stored for delivery (without blending) to users of devices incorporating the presently disclosed embodiments, an unlimited number of scents can also be rapidly created and generated, on-demand, according to formulae (and other instructions) by blending basic chemical ingredients (incorporating odor generating chemicals), to create scent compounds (the foregoing action referred to as "compounding"). According to some embodiments, ingredients may be stored in liquid, semi-solid or solid state, and in the case of scents include aroma emitting chemicals, additives, and other chemicals including, by way of example but not limited to:

Acetanisole, *Commiphora erythraea*, ext., Octanal dimethyl acetal, Methyl-4-phenyl-2-butyl isobutyrate, Ethylbutyl acetate, Heptanal dimethyl acetal, Hexyl isovalerate, Hexyl 2-methylbutyrate, Styrene, Benzonitrile, Benzyl alcohol, Benzaldehyde, alpha,alpha-Dimethylphenethyl alcohol, alpha,alpha-Dimethylphenethyl butyrate, 3-Hexenyl 2-methylbutanoate, alpha-Methylcinnamaldehyde, Methyl phenylacetate, Phenylacetaldehyde dimethyl acetal, Phenylacetaldehyde ethylene glycol acetal, 1-(Methylthio)-1-Propene, Diphenylmethane, Diphenyl ether, alpha-Amylcinnamyl alcohol, alpha-Hexylcinnamaldehyde, p-Tolyl phenylacetate, Ethyl phenylacetate, Isobutyl phenylacetate, Benzyl phenylacetate, Anisyl phenylacetate, Isoamyl phenylacetate, Phenethyl phenylacetate, Triethanolamine, (tri-) Acetin, Benzyl octanoate, 2-Methyl-4-phenyl-2-butanol, Di-(2-ethylhexyl) adipate, Ethyl cinnamate, Benzyl cinnamate, Oils, jasmine, *Jasminum sambac*, Phenethyl isobutyrate, Cinnamyl acetate, Carbonic acid, Acetanilid, p-Tolyl isobutyrate, Menthone, Oils, *Iris germanica*, Rhodinyl phenylacetate, Methyl-2-butenal, Pentanone, Myrtenyl acetate, Butyric acid, Resorcinol, Cyclohexanol, Phenol, Valeric acid, etc.

The ingredients are stored and selectively released, so that a selected group of ingredients (uniformly in one of either gases, vapor or liquid form) are sent to a central blending chamber to create homogeneous compounds according to specified formulae that have been programmed for activated blending, or by manual or other selection. Optionally, multiple blending chambers may be configured and operationally controlled to blend and mix homogeneous compounds for user delivery.

With specific reference to the preparation of scented gases, ingredients to be blended contain the essential ingredients of a desired or specified scent or flavor in solvents, semi-solid or solid state, but also catalyst or enzymatic chemicals or other additives. The central blending chamber(s) can also have heating and pressurizing capabilities to enable chemical reactions, as the thermodynamic energy barrier(s) for chemical reaction to occur may sometimes need to be overcome by higher temperature or pressure. Also, the kinetics of reaction (and blending) of chemical ingredients may not always be fast enough for efficient and fast-responding, scent or flavor delivery systems. The temperature range to control in the blending chamber to enable or enhance the digital compounding of scents or flavors can be variably set in a desired range of up to 200° C., according to optimal temperature determined for optimally blending specific gas compounds. The pressure range in the chamber to control is in the range of 0.1-100 atmospheres, preferably 0.5-20 atmospheres, and even more preferably 1-5 atmospheres.

FIG. 3(A) depicts an apparatus 300 that can be used for blending multiple scents. The apparatus includes an array of scent containers (306), a flow regulation mechanism (e.g., 304 and/or 308), a mixing chamber 310 and a pressurization chamber 302. Each container in the array may have an inlet through which an input gas flows in, a chamber for holding a scent ingredient, and an outlet through which a mixture of the input gas and the scent ingredient flows out. The flow regulation mechanism may include either remanent magnetization valves 304, controlling passage of gas from the pressurization chamber into the inlet of the chamber or magnetic check valves 308 positioned at outputs of the chambers and controlling passage into the mixing chamber 310, or both. In some embodiments a vacuum suction chamber (not shown in FIG. 3(A)) may be used in addition to or instead of the pressurization chamber 302 to forcefully flow the gas into the inlet of the container.

As depicted in FIG. 3 (A), ingredient combination may be accomplished via simultaneous opening of various remanent magnetization valves, thereby permitting fluid flow through or from the ingredient containers and blending in a blending chamber prior to delivery. This is only a basic description of blending but by incorporating duty-cycling of the valves to control ingredient concentration, ratios and other parameters, greater homogenization and ratio and concentrations control, as well as variation is possible (even with limited ingredients). For higher ingredient numbers, locating the ingredients chambers away from the central blending chamber may be necessary as shown in FIG. 3 (B). The remotely located ingredients could then be delivered by channel to a blending chamber for combination and mixing.

FIG. 3 (C) and FIG. 3 (D) each portray high-capacity device configurations with a disk shaped cartridge comprising up to 1000s of individual ingredients which mates with an array of remanent magnetization valves. Containers are selected by valve activation. Multiple selections simultaneously permit combinatorial blending of ingredients. For simplified electronic control, single valves may account for individual radii of ingredient containers facilitated by rotation of the cartridge disk or valve housing to match valves to ingredients. Stacked configurations and mirrored configurations allow for higher ingredient numbers without further expanding, or possibly reducing disk size. Disks could be replaced, refilled, or recycled as needed. For ingredient replenishment, the flat, disk, ring, or nested cartridge may be seated into a separate refill/recharge unit. Refill may be accomplished via pressurized delivery or simple capillary action.

In particular, FIG. 3 (D) shows examples of a stacked configuration in which container arrays having similar container placement patterns (e.g., along radii of a disk-shaped pattern) are stacked on top of each other in a stacked configuration (314) or are in a mirrored configuration (316) in which one array is flipped or mirrored and stacked above the other array. In the mirrored configuration (316), gas outlets of the containers from the two arrays will be facing each other. These configurations may allow for a simplified electronic control during which arrays may be rotated to match valves to ingredients. Stacked and mirrored configuration allow for denser packing of scent containers without increasing size (radius) of the disk.

Similarly, FIG. 3 (E) and FIG. 3 (F) portray high capacity device configurations with cylindrical ring containers comprising up to 1000s of individual ingredients which mate with an array of remanent magnetization valves. Containers are selected by valve activation. Multiple selections simultaneously activate combinatorial blending of ingredients. The number of ingredients can be increased by nesting rings so long as a pressure difference is maintained with each additional interior ring maintaining a pressure drop. To accomplish this, pressurized open passages between levels are maintained such that flow can pass into the ring even if no valves are open in a nested level. Similar to the disk-type structure of FIG. 3 (D), rings or valve arrays may be rotated to minimize the number of valves in use if desired.

In the embodiment depicted in FIG. 3 (F), three concentric rings of containers are nested within each other in a generally concentric manner. In the depicted embodiments, for each ringed array, a housing ring is on the outside of, and supports an inner ring that holds the container array. Advantageously, the arrayed containers are thus oriented with their outlets generally pointing towards the center. The mixing chamber is located towards to chamber for collecting the mixture and providing a blended output according to a formula, for the intended application. During operation, pressurization occurs external to the largest diameter ring with gas flow to the exterior of the nested second largest ring accomplished via activation of selected remanent magnetization valves permitting flow through the largest diameter ring and coupled container ring. For unscented flow from the exterior to the interior ring, valves coupled with containers without scented material may be activated. To maintain a consistent pressure drop, valves arrayed against scented and unscented containers may be timed, sequenced, and cycled. Subsequent transitions to further nested rings may be accomplished via the same mechanism, i.e. sequenced, timed, and cycled flow through scented or unscented containers as controlled by remanent magnetization valve activation.

In order to achieve a satisfactory blending of various ingredients to a combined scented or unscented fluid, active agitation (separately, or in conjunction with variably controlled temperature and pressure) may be necessary. In interest of reducing power consumption, geometric approaches are presented in FIG. 3 (G) where rotational motion is employed to mix components. Should angled exit streams prove insufficient, spiral inserts or similar may be used to force or assist blending.

The control and adjustment of the intensity or concentration of fluid release may be desirable for various applications and can be achieved via a mechanism for diminishing the ratio in a mix of released material to inert background material (e.g. gas or some solvent). FIG. 3 (H) describes schematically a three-way blending/dividing valve operated by remanent magnetization latching with an internal arc positionable to divide/combine flows in various ratios with arc position determined by external latchable magnets aligning with an internal high-permeability pin. This configuration, when positioned to divide flow between channels which load or scented or unscented the gas or solvent and a channel which does not may effectively act as an intensity or concentration control for fluid delivery of the ultimate recombined stream. In the case of scent delivery, said mechanism permits variable adjustment of the perceived intensity of the smell of the selected substance. The latchable remanent magnetization blending/dividing valve utilizes a three-channel intersection mediated by a cylindrical chamber containing a precisely produced blocking wedge sector which may fully obfuscate entry to or exit from a single channel or be positioned at an angle between two entrance/exit channels to divide or recombine flow in a particular ratio. The inner cylindrical chamber may remain completely sealed but still be controllable through the use of an arc of latchable remanent magnetization pins positioned to magnetically interact with a high permeability mating piece embedded in the blocking wedge sector. To position the wedge, solenoids wrapped around each latchable pin are used to successively magnetize and demagnetize the pins and to step the internal wedge to the determined radial position. Once the position is reached, the magnetized remanent pin passively maintains the position without the need of any additional power. As before magnetization is accomplished by a DC current through the solenoid and demagnetization by either a diminishing AC field or diminished DC field steps in alternating directions (one or many steps). Varying the angle of the blocking wedge within the valve controls the ratio of flow to/from the affected channels. The scent generating device according to the invention can handle a very large number of ingredients because of the compact dimension. A preferred number of ingredients to mix and generate many different types of scents in the disclosed scent generating device is at least 100, preferably at least 1,000, more preferably at least 5,000.

Devices for combinatorial fluid production may for scent compounding may be configured for wearable applications with a variety of potential embodiments disclosed in the following section. Devices may be implemented with one-to-one matching of control valves to ingredient containers within an array, or they may use rotational, X-Y, or X-Y-Z matrix configurations to position scent containers for delivery either individually, sequentially, or concurrently. Positioning, for example, may be controlled by electric motor or staggered remanent magnetization pins as in FIG. 3 (H).

Examples of Scent Delivery Device Configurations

Figure 4A:
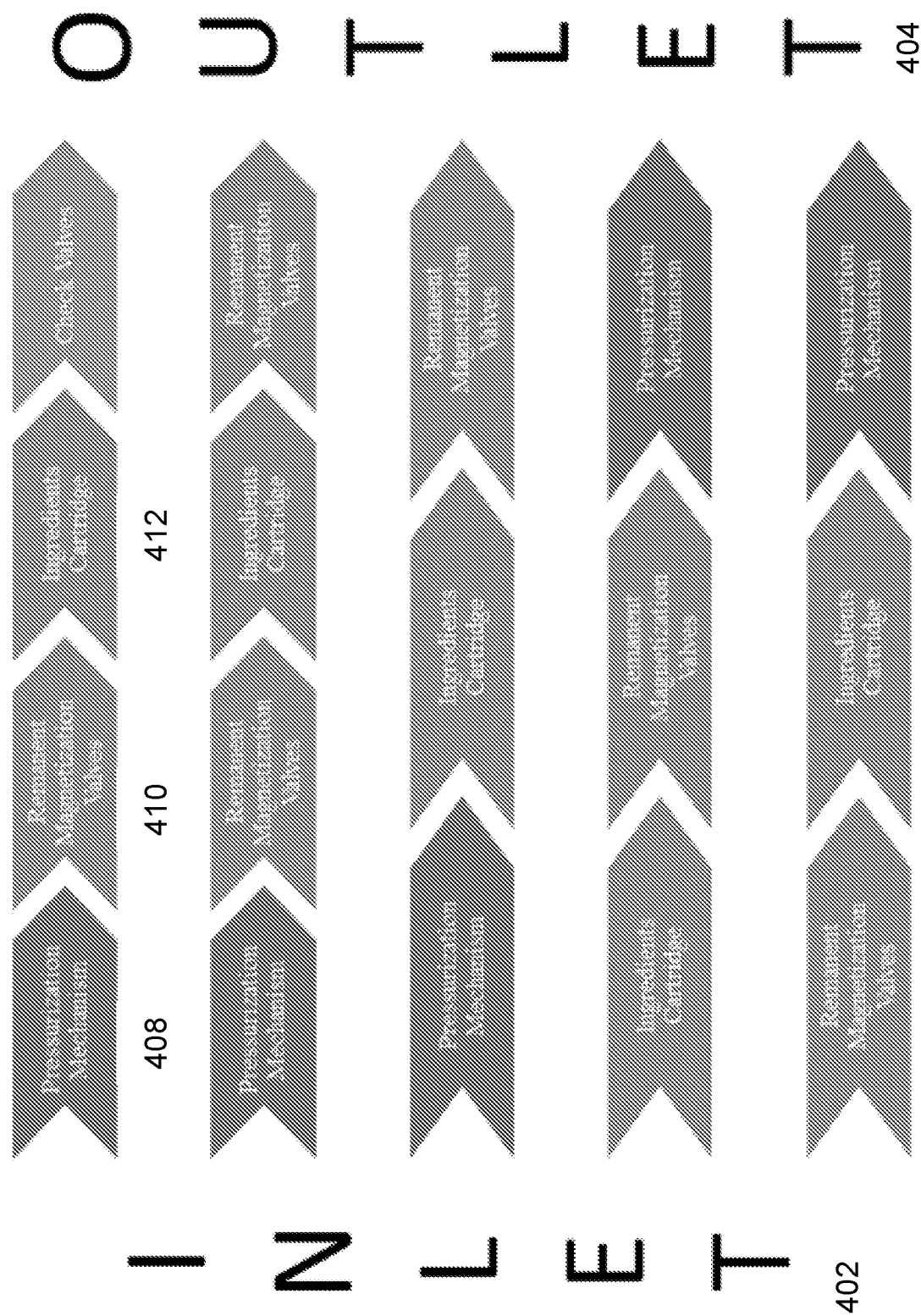
FIG. 4 (A)-(W) schematically illustrates various embodiments of scent delivery devices and structures: (A) alternative containers, valve, and pressurization configurations; (B) an interchangeable cartridge which mates with an array of remanent magnetization valves for controlled release; (C) an interchangeable cartridge with arrayed check valves at exit for controlled release; (D) an under-nose cartridge structures for scented gas delivery ("scent delivery") to users of virtual reality devices, augmented or mixed reality ("VAR") devices; (E) scent delivery with midline cartridge location in the headset for VAR devices; (F) a fully or partially disposable scent delivery unit for VAR devices; (G) self-contained controllable scent delivery from one- or two-side-mounted replaceable/refillable cartridge(s) attached to and for use with VAR head or eyewear; (H) self-contained controllable scent delivery from one-side-mounted replaceable/refillable cartridge(s) attached to and for use with VR or AR headgear with small diffuser; (I) self-contained controllable scent delivery from a neck-mounted replaceable/refillable cartridge; (J) self-contained controllable scent delivery from a belt-mounted replaceable/refillable cartridge; (K) self-contained controllable scent delivery from an arm-mounted replaceable/refillable cartridge; (L) self-contained controllable scent delivery from a tabletop or handheld replaceable/refillable cartridge; (M) self-contained controllable scent delivery from a large central unit with a large scent capacity (i.e. thousands of dedicated scents); (N) directional scent delivery via directed dual or triple scent output; (O) a scent delivery device situated below the user's nostrils with in-built microphone for audio capture and interaction during use; (P) a wired desktop configuration for scent delivery; (Q) a wireless desktop configuration for scent or alternative delivery; (R) a mobile or fixed scent delivery multi-media device with flexible dimensions and placement as a unit; (S) self-contained controllable scent delivery from a handheld device with detachable, replaceable or refillable cartridge; (T) a handheld scent delivery device with object recognition via incorporated camera or wired or wireless transmission of data for selective activation of scent delivery; (U) a scent delivery device situated to also deliver flavored fluid to the user's nosespace or mouth; (V) an intake dehumidifier for multi-climate operation; and (W) an exhaust mechanism for residue release during cleaning. Configurations shown in FIG. 4 (A)-(W) can optionally be used with, attached to, or incorporated into VR or AR headgear or eyewear, or, alternatively, configured to operate and be worn independently for alternate uses.

A wide variety of scent delivery device configurations may prove advantageous for diverse applications. FIG. 4 (A) shows alternative container, valve, and pressurization configurations. Pressurization may be located either at the inlet or outlet of the device. Remanent magnetization valves may come before, after, or both before and after the fragrance ingredient container. Check valves may come at the exit of the device affixed to the container. A sampling of potential hardware configurations is provided in the remainder of FIG. 4. FIG. 4(A) thus illustrates different possible configurations of a scent delivery system in which the sequence of pressurization, valve and containers can be different according to an intended application of the system.

For convenience a scent fluid releasing device may be configured as in FIG. 4 (B) which schematically shows an interchangeable cartridge that mates with an array of remanent magnetization valves for controlled release. As depicted, the cartridge may have, for example, 95 containers arrayed in a 5×19 matrix such that when inserted into the device and secured by physical latching, friction, spring locks, or some typical mechanical means each of the 95 containers is aligned with one port of a remanent valve array and one exit port directly into the user's nose space. Release may then be accomplished by depressing the cartridge to eject, widening the hooked latch edge, manually pulling on the cartridge, or some other typical ejection means. Cartridges may be replaced, recycled, refilled, or discarded. In this configuration, which requires no channeling for scent delivery, deposition buildup issues are eliminated. Release may be activated and controlled by any convenient method such as laser, Wi-Fi, or other wireless signal, sensor, electrical connection to the headset, actuators, buttons, etc. Pressurization may be provided by an internal miniature fan, pump, or similar. Individual scented gases may be delivered via singular valve activation. Conversely, blending of multiple ingredients may be accomplished via simultaneous or duty-cycled activation of additional valves. FIG. 4(B) thus illustrates examples of cartridge based designs that allow for differing scent compositions or ingredients according to utilization, and wherein the scent delivery device may be affixed centrally to a VAR headware or eyewear.

FIG. 4 (C) shows another configuration for under-nose scent delivery from a cartridge mated with a valve housing and pressurization chamber all mounted directly to a VR or AR headset. As depicted, the cartridge may have, for example, 128 containers arrayed in an 8×16 matrix such that when inserted into the device and secured by physical latching, friction, spring locks, or some typical mechanical means each of the 128 containers is aligned with one port of a remanent valve array and one exit port directly into the user's nosespace. Exit ports may optionally include a magnetic check valve for diffusion control and long-term use. Cartridge release may be accomplished by depressing the cartridge to eject, widening the hooked latch edge, manually pulling on the cartridge, or some other typical ejection means. Cartridges may be replaced, recycled, refilled, or discarded. In this configuration, which requires no channeling for scent delivery, many deposition buildup issues are eliminated. Release may be activated and controlled by any convenient method such as wireless, electrical connection to the headset, actuators, buttons, etc. Pressurization may be provided by an internal miniature fan, pump, or similar. Individual scented gases may be delivered via singular valve activation. Conversely, blending of multiple ingredients may be accomplished via simultaneous or duty-cycled activation of additional valves FIG. 4 (D) shows a schematic diagram of under-nose cartridge structures for scented gas delivery for virtual reality ("VR") devices, or augmented or mixed reality ("AR") devices. The drawing shows VR or AR headset with scent containers, optionally divided into a dedicated compartment for scent storage material and a separate compartment with substrate dosed with and fed by the storage material) situated directly beneath. A cartridge containing scent material and substrates (for scented or unscented gas generation) may be removed for refill/replacement/recycle. A cartridge is controlled by adjacent structures containing means to drive gas through the cartridge and selected containers, including containers containing fragrance or flavor substrates. A cartridge may be refilled by docking with stand-alone recharge unit or alternatively sent for recycle. The scented gas is released directly from the selectively activated scented substrate container inside the cartridge directly into the nose space. In this type of design, the cartridge is very closely positioned to the scent exit region, so the use of a connecting channel or an array of tubes or channels of other geometry for scent transport can be omitted, which makes the device simpler and less expensive, and eliminates/minimizes any scent material deposition on the connecting channel inner wall surface, which may contaminate/degrade the quality of other scent(s) to be delivered later. The scent release actuation can be performed by either wireless or wired signaling, or sensor-activated. With respect to this latter (sensor-activated option), for example, sniffing or breathing by the user can trigger a sound sensor or gas-flow sensor to initiate the scent release. Individual scented gases may be delivered via singular valve activation. Conversely, blending of multiple ingredients may be accomplished via simultaneous or duty-cycled activation of additional valves. In FIG. 4(C), clockwise from left-top, first, a configuration in which the VR/AR headset with scent containers is directly beneath a user's nostrils is shown. Next, the scent containing cartridge is shown to be removable from the headset for refill, replacement, recycle or another purpose. The cartridge may be refilled by docking with a standalone recharge unit (an example is depicted in the lower right inset of FIG. 4(C) or may be sent to recycling (discarded). In the lower left inset, a configuration of the headset is shown with allows for adjacent control of gas flow and scent selection. Scents may be directly released near the nosespace without using a directed flow tubing. Scent release actuation may be achieved by wireless signaling or wired signaling or be sensor activated, e.g., sniffing by or inhalation from nose may trigger a sound or a gas-flow sensor to trigger scent release.

FIG. 4 (E) illustrates examples of scent delivery with midline cartridge location for VAR devices. The scented gas is created by directing gas flow through a removable/replaceable scent cartridge with open scent container selected by remanent magnetization switch and into its dedicated tube or channel leading to a scent diffuser near the user's nostrils.

FIG. 4 (E) schematically illustrates diagrams of scent delivery with midline cartridge location in the headset for VAR devices. Self-contained scent delivery unit may be clipped to glasses or VAR eyewear or worn alone with a structural brace, strap or other support placed on or around the head (420). Scent containing cartridge is removable for recharge or replacement (422). Scented gases are delivered from the cartridge to the nosespace by separate channels (426). Controller, pump, power and switches can all be interior for compact design and efficient operations (424). Scent release is fully controllable by adjacent switches. Scent release is accomplished by pushing gas flow through a removable/replaceable scent cartridge with an open scent container selected by remanent magnetization switch and then scented gas delivered through separate channeling to a scent diffuser near the user's nostrils. Individual scented gases may be delivered via singular valve activation. Conversely, blending of multiple ingredients may be accomplished via simultaneous or duty-cycled activation of additional valves. Scented gas may be created by directing gas flow through the removable/replaceable scent cartridge with open scent containers selected by remanent magnetization switches permitting scented flow into dedicated tubes or channels leading to a scent diffuser near the user's nostril.

Described in FIG. 4 (F) are fully or partially disposable scent delivery units for VAR devices. Scent release is accomplished by pushing gas flow through the disposable/recyclable cartridge, outbound channels, and diffuser near the nostrils (428). Scent is selected by remanent magnetization switches in the permanent portion comprised of fan, battery, microelectronics, and switches. Fully disposable/recyclable, self-contained scent delivery may also be attached to or incorporated into used with VAR devices or be worn alone. Partially disposable scent delivery device with replaceable portion slotting into permanent portion can also be one of the embodiment configurations (430). The permanent portion of the scent delivery device contains battery, fan, microelectronics, and switches (432). Disposable/recyclable portion contains scent cartridge, outbound channels, and diffuser to be slotted into permanent portion (434). Scent release is accomplished by pushing gas flow through the disposable/recyclable cartridge, outbound channels, and diffuser near the nostrils. Scent is selected by remanent magnetization switches in the permanent portion comprised of fan, battery, microelectronics, and switches. Individual scented gases may be delivered via singular valve activation. Conversely, blending of multiple ingredients may be accomplished via simultaneous or duty-cycled activation of additional valves. Various embodiments of valves described herein, e.g., using remanent magnetization switches located in the permanent portion 432 may be used for controlling the scent delivery.

FIG. 4 (G)-(M) schematically illustrate various embodiments of scent ingredient storage and delivery structures utilizing a cartridge or an array of cartridges, which are mounted/positioned at various locations.

FIG. 4 (G) describes a self-contained controllable scent delivery from one or more side-mounted replaceable/refillable cartridges for use with VAR devices or wearable alone with suitable attachment to the head (434). Scent release is accomplished by pushing gas flow through a removable/replaceable scent cartridge located at the side of the head with an open scent container selected by remanent magnetization switch and then scented gas delivered through separate channeling to a scent diffuser near the user's nostrils. All scent release from headset, eyewear, or other configuration devices can be programmably actuated by wireless signals (such as Wi-Fi) or hard wired signals. The control software can be either stored in the hardware components or can be utilized through wireless signals. A symmetrical cartridge could also be positioned on the opposite side of the head with delivery arm leading into the same diffuser.

FIG. 4 (H) describes a self-contained controllable scent delivery from one or more side-mounted replaceable/refillable cartridges for use with VAR devices or wearable alone with suitable attachment to the head and small nosespace diffuser (436). Scent release is accomplished by pushing gas flow through a removable/replaceable scent cartridge located at the side of the head with an open scent container selected by remanent magnetization switch and then scented gas delivered through separate channeling to a scent diffuser near the user's nostrils. All scent release from headset or other configuration devices can be programmably actuated by wireless signals (such as Wi-Fi) or hard wired signals. The control software can be either stored in the hardware components or can be utilized through wireless signals.

FIG. 4 (I) illustrates a self-contained controllable scent delivery from a neck-mounted replaceable/refillable cartridge. Scent release is accomplished by pushing gas flow through a removable/replaceable scent unit with cartridge suspended from the user's neck up through scent-specific channeling to an anchored position at the side of the head and then to a scent diffuser near the user's nostrils. Control mechanisms and fan/pump are located with the suspended cartridge. As an alternative, a larger unit containing control mechanisms, fan/pump and scent cartridge(s) could be rear mounted as a backpack to allow for a greater number or longer-lasting amount of scents.

FIG. 4 (J) illustrates a self-contained controllable scent delivery from a belt-mounted replaceable/refillable cartridge. Configuration can be worn and used with or without attachment to VAR headset or eyewear. Scent release is accomplished by pushing gas flow through a removable/replaceable scent cartridge suspended from the user's belt up through scent-specific channeling to an anchored position at the side of the head, or alternatively routed to it, and then to a scent diffuser near the user's nostrils. Control mechanisms and fan/pump are located with the suspended cartridge.

FIG. 4 (K) describes a self-contained controllable scent delivery from an arm-mounted replaceable/refillable cartridge. Scent release is accomplished by pushing gas flow through a unit containing removable/replaceable scent cartridge suspended from the user's arm up through scent-specific channeling to an anchored position at the side of the head and then to a scent diffuser near the user's nostrils. Control mechanisms and fan/pump are located with the unit.

FIG. 4 (L) describes a self-contained controllable scent delivery from a tabletop or handheld replaceable/refillable cartridge. Device can be configured for use with or without VR or AR headset. Scent release is accomplished by pushing gas flow through a removable/replaceable scent cartridge in a tabletop or handheld unit up through scent-specific channeling to an anchored position at the side of the head and then to a scent diffuser near the user's nostrils. Control mechanisms and fan/pump are located with the scent cartridge.

FIG. 4 (M) describes self-contained, controllable scent delivery from a large central unit with a large scent capacity (i.e. thousands of dedicated scents). Device can be configured for use with or without VAR device (e.g. for normal viewing of televisions or desktop computer monitors). Scent release is accomplished by pushing gas flow through a scent cartridge in the large central unit up through scent-specific channeling to an anchored position at the side of the head and then to a scent diffuser near the user's nostrils. Control mechanisms and fan/pump are located in the large central unit with a large capacity of dedicated scents.

In FIG. 4 (G)-(M), scent release is accomplished by pushing gas flow through a conveniently located removable/replaceable scent cartridge with an open scent container selected by remanent magnetization switch and then scented gas delivered through separate channeling to a scent diffuser near the user's nostrils. All scent release from headset or other configuration devices can be programmably actuated by wireless or hard wired signals. The control software can be either stored in the hardware components or can be utilized through wireless signals or sensors. A symmetrical cartridge could also be positioned on the opposite side of the head with delivery arm leading into the same diffuser. Control mechanisms and fan/pump may be located with the suspended cartridge unit or anchored with the headset or eyewear. Individual scented gases may be delivered via singular valve activation. Conversely, blending of multiple ingredients may be accomplished via simultaneous or duty-cycled activation of additional valves.

FIG. 4 (N) shows an example three-dimensional scent delivery with dual or triple scent diffuser outputs. For directional scents, employing dual or triple scent streams with varying scent compositions and concentrations allows for precise control of scent (location of origin and other) perception. Delivery into the nosespace may be via fully separated channeling, or a combined or bundled channel with separated outputs.

FIG. 4 (N) depicts two potential configurations for directional scent delivery applicable to three-dimensional environments. Employing dual scent streams with varying scent compositions allows for precise control of scent perception. Delivery into the nosespace may be via fully separated channeling, or a combined or bundled channel with separated outputs. For example, in some embodiments, a first channel ("left channel") may be used for delivery of scent and a second channel ("right channel") may be used for delivery of corresponding dual scent, such that, at the output, the fluid being delivered out of the first output channel may be a combination of the left channel and the right channel and similarly a second output channel also may have scent delivered as a combination of the left and the right channels, in proportions controlled by the delivery system to provide a directional or spatial scent experience to the user. As with previous configurations, scent selection is accomplished by remanent magnetization valve activation. Scent concentrations may be varied dynamically via pressurization levels, duty-cycling, temperature and/or blending. Individual scented gases may be delivered via singular valve activation. Conversely, blending of multiple ingredients may be accomplished via simultaneous or duty-cycled activation of additional valves.

In multimedia applications of controlled delivery (e.g. scent delivery), incorporation of an audio microphone into the nose space diffuser is a useful addition to the device to provide a combined audio and scent functionality. As depicted in FIG. 4 (O) schematically, one potential embodiment of a scent delivery device situated below the user's nostrils has an in-built microphone for audio capture and interaction during use. The adjacent location of the scent release and the auditory signals produced by the mouth is conveniently accommodated by a single armature in this instance. Other embodiments may be connected by dual armatures or a single central connection to the headset. Auditory signals may also be used to selectively, automatically or programmatically trigger automated or programmed scent activation, and vice versa. A speech recognition mechanism may also be employed. Additionally, software that programmably coordinates the pairing of key words/phrases and/or sound (including without limitation the sound of breathing) dynamics with release of scent counterparts may be implemented.

FIG. 4 (P) shows a schematic illustrations of a wired desktop configuration for scent release. Signals from an adjacent computer are carried to scent release device by wire connection initiating scent release on command. Computer or release device contains control software that programmably releases the desired scent(s). Release may be directed by adjustable exit port or diffuser to a targeted space. Wired connections for scent release can be extended to various other applications beyond desktop applications, for example, brick and mortar shopping experiences, live entertainment, teleconferencing, etc.

Similarly, FIG. 4 (Q) depicts a wireless connected desktop scent release configuration. As shown in the figures, the scent release actuation and management can be controlled by wired signals from an adjacent computer or by wireless signals from an adjacent computer, or through wireless signal or cell phone signal in combination with local wireless control. Computer or release device contains control software that programmably release the desired scent(s). The control software that initiates the release, maintains the duration and frequency and intensity of releases, and the termination of scent release, as well as the software that connect/coordinate various devices are some aspects of the disclosed technology. The software can also be utilized for synchronizing of multi-media display, including coordination of image, sound, scent, and/or other sensory elements or elements of content such as story, action, character, lighting, music, sound, movement, (in the case of traditional film or animation) cuts and dissolves, (in the case of VR) transport between scenes, setting in terms of timing, sequencing, repetition, user priming, and so forth. The scent release may be by directed diffuser or through flexible scented channeling or channels, with or without the diffuser. Wired and wireless connections for scent release can be extended to various other applications beyond desktop applications, for example, on-line shopping, VAR experience or entertainment, teleconferencing, PPC banner or other type of online advertisement, wearable applications such as clothing or jewelry, advertising kiosks or displays, etc. Individual scented gases may be delivered via singular valve activation. Conversely, blending of multiple ingredients may be accomplished via simultaneous or duty-cycled activation of additional valves.

In some embodiments, wireless signals from a nearby computer, or transmitting sensors such as beacons are communicated to scent release device to initiate scent generation and release on command. Computer or release device contains control software that is an integral part of the invented device, and is programmed to select, generate and actively release the desired scent(s) in certain fashion. Release may be by directed by adjustable exit port or diffuser to a targeted space. Wireless connections for scent release include desktop use as well as such applications as brick and mortar in-store display or point of sale or product shopping, teleconferencing, etc. Device can also be miniaturized for wearable applications such as device worn around the neck and angled towards user's nose space.

FIG. 4 (R) illustrates a mobile or fixed scent delivery device with flexible dimensions and placement as a unit. The unit may be set into a false wall, sit as a large floor-based stand-alone unit, a smaller tabletop seated unit, or other dimensionally flexible configuration. The unit may have integrated user interface or external connection to any wired or wireless enabled media device. Scent may be replenished by refill or cartridge replacement/recycle. Scent release is accomplished by pushing airflow through a scent container located within the unit through scent-specific channeling to a directed scent diffuser adjustably aimed at the user's nosespace. Control mechanisms and fan/pump are located in the unit with a large capacity of dedicated scents. Device may be constructed as a mobile unit or as fixed unit. Form, shape, and placement are flexible. Individual scented gases may be delivered via singular valve activation. Conversely, blending of multiple ingredients may be accomplished via simultaneous or duty-cycled activation of additional valves.

FIG. 4 (S) schematically illustrates self-contained controllable scent delivery from a handheld device with detachable, replaceable or refillable cartridge. Scent release is accomplished by pushing gas flow through a removable/replaceable scent cartridge preferably located at upper portion of the handheld with a scent container selected by remanent magnetization switch and scented gas delivered through separate channeling to a scent diffuser at the end of the device. Such an independent self-contained controllable scent delivery from a handheld, physically separated device (the expression "hand-held" here includes finger-held, or worn at any part of the bare human or animal body) can be actuated by pressing of one or more buttons on the unit itself, or by a wireless signal, cell phone signal, magnetic signal, optical signal, laser signal, sound/vibrational signal, or any cordless remote signal or sensor, actuated by the holder or another person who is not holding the device. Such an independent scent delivery device or an array of them, can also be placed on a remote location such as on a table top or on a wall or attached to another device or fixture, and actuated by the operator nearby or remotely located using wireless or other remote signaling. For additional functionality, FIG. 4 (U) incorporates a camera, with which the handheld device can optionally identify a product and trigger a specified scent. The device can, wired or wirelessly, programmably synchronize to any digital/wireless, electronic, projector, VAR or live media. In either configuration, individual scented gases may be delivered via singular valve activation. Conversely, blending of multiple ingredients may be accomplished via simultaneous or duty-cycled activation of additional valves.

Any of the previous device configurations can optionally include flavor/taste delivery with a conveniently located diffuser as in FIG. 4 (T). The scent devices disclosed herein may be activated to deliver flavored gas to the user during eating to enhance, modulate, or modify perception of taste. The scent devices may also be activated to deliver flavored gas while a user physically or in simulated fashion (VR, AR holographic or mixed reality activity) eats or drinks, or shops for foods or beverages or other objects that are associated with taste. With incorporated camera, the handheld device can optionally identify a product and trigger a specified scent. The device can, wired or wirelessly, programmably synchronize to any digital/wireless, electronic, projected, or live media.

As humidity levels may directly impact the quality, comfort or sensory impression of scent production from a scent delivery device, FIG. 4 (V) schematically illustrates the inclusion of a dehumidifier at the intake port of the device to standardize the scent delivery parameters for multi-climate operation. Such dehumidifier may be combined, or placed subsequent or preceding to a carbon filter or other gas purification filter. Such dehumidifier may be always activated, manually activated, or sensor activated. Flavor/Taste distribution may be incorporated into the conveniently located diffuser dispersal mechanism.

FIG. 4 (W) schematically depicts an exhaust mechanism to be used in conjunction with any of the various cleaning mechanisms described herein (see FIG. 5). As needed, scent delivery devices may require an alternative exit valve through which any waste substance from cleaning may be discharged periodically. Including an additional dual remanent magnetization valve near the device output allows for diverting the flow away from the user's nosespace during and immediately following cleaning. As humidity levels may directly impact the quality of fluid production from a scent or other fluid delivery device, optionally, a dehumidifier may be included at the intake port of the device. Such dehumidifier may be always activated, manually activated, or sensor activated.

Examples of Fluid Delivery Channel Configurations

Deposition buildup on the interior of fluid delivery channels is a significant limitation preventing the utilization of multi-flow channeling and increasing the overall material necessary for high capacity devices. Such deposits on the wall may also produce some scent and contaminate a subsequent incoming scent, thus affecting the cleanness and quality of the olfactory rendition of other scented fluids sent through the same channel later times. FIG. 5 (A)-(G) represents various embodiments of channel deposition cleaning procedures for the delivery of multiple ingredients or materials consecutively or simultaneously down a single channel. Thermal, chemical, and electromagnetic/mechanical approaches are disclosed.

FIG. 5 (A) shows a schematic illustration of bundled scent-specific delivery channels for delivery of various scented or unscented fluids to prevent cross-contamination of scents, each scent delivered from a scent container has a single specific tube or channel that is not shared with any other scents. Such an assembly of individuated tubes or channels necessitate a larger overall diameter, which is acceptable for some applications and may be less desirable for some other applications that may require many different scents (e.g., more than 10 different scents) and may prefer compactness rather than bulkiness, such as a light-weight headset or eyewear worn by a user. To prevent cross-contamination of types of fluids, each fluid delivered from a container loaded with that fluid material has a single specific tube that is not shared with any other fluid.

FIG. 5 (B) schematically depicts a nonporous residue-resistant single channel which can be used for delivery of different scents at different times. Using a single residue-resistant channel allows an overall device size reduction. For this purpose, the channel interior can be coated, for example, with a hydrophobic and/or lipophobic interior coating, smooth metal/ceramic layer deposition and plating (preferably an inert material) or other deposition-resistant material that prevents or minimizes scent accumulations and contaminations. In this embodiment, a single channel can deliver many scented or unscented fluids over a period of time, while preventing or minimizing cross-contamination of scents. In some embodiments, a single residue-resistant fluid delivery tube or channel can accommodate the sequenced release and delivery of many individual differently scented or unscented fluids without deposition on the inside surface of the delivery channel thereby preventing cross-contamination of fluids. A single, fluid delivery channel can significantly reduce the overall size of the device. Tube (or channel of other geometry) interior can be coated with a hydrophobic and/or lipophobic material/texture or smooth metal/ceramic layer deposition and plating that prevents or minimizes scent accumulations/contaminations.

FIG. 5 (C) depicts deposition cleaning of an internal coating by resistive heating. A conductive liner is deposited on the interior of the delivery channel (or produced around a central element which is subsequently removed, e.g. by dissolution). Passing a current through the internal liner is then used to resistively heat the interior surface to break up or dissolve any surface depositions. In combination with initial internal polishing or suitable coating to minimize buildup, resistive heating can effectively clear the channel of the previous flow material and allow for differing materials to be passed through the channel successively with minimal contamination. The metal liner on the inside wall of the channeling can be simply a thin-wall flexible metal channeling inserted into a plastic (e.g. PTFE or similar or other flexible) channeling. The metal channeling insert can be either a seamless channeling or an incompletely closed, bent or pliable metal sheet in the form of channeling. Alternatively, the metal liner can be a thin deposited metal on the inside wall of the channeling, for example, accomplished by sputtering, evaporation, electroplating or electroless plating, or chemical vapor deposition. Desirable metals for electrical current resistive heating are made of high electrical resistivity alloys, such as Nichrome alloy (made of e.g., 80% Ni and 20% of Cr).

FIG. 5 (D) depicts deposition cleaning of an internal coating by inductive heating. A conductive magnetic liner is deposited or inserted on the interior of the delivery channel (or produced around a central element which is subsequently removed, e.g. by dissolution). The inner liner may then be inductively heated by a wrapping solenoid when activated by a high frequency AC signal. For inductive coupled heating using AC or RF field, the preferred liner material can be a metals or alloys, preferably strongly ferromagnetic alloys such as steel, silicon steel, or Permalloy. Such magnetic alloy liner can be a simple metal channeling inserted or deposited by sputtering, evaporation, electroplating, electroless plating, or chemical vapor deposition. Preferred thickness of the inner liner metal foil can be in the range of 1-1,000 µm, preferably 5-100 µm. The lower limit thickness is to make sure that handling of a thin foil does not become too difficult or too delicate, and also to ensure sufficient, rapid heating by magnetic induction. The upper limit is for the purpose of compactness of device, as well as to ensure that a sufficient electrical resistance is obtained with a thinner dimension foil for electrical resistance heating. In the case of thin film coating by physical vapor deposition, chemical vapor deposition, electrochemical or electroless deposition, the desired thickness is in the range of 0.2-50 µm, preferably 0.5-5 µm.

Chemical purging of the multi-flow channel as in FIG. 5 (E) may be used singularly or in combination with another deposition cleaning technique. A clean multi-flow channel when exposed to a scented or unscented fluid flow experiences deposition buildup due to factors such as molecular bonding with the surface or mechanical restriction in surface imperfections or van der Waals forces. A periodic, separate chemical purge, e.g. with acetone or other chemical vapor, dissolves this interior buildup layer to restore a clean multi-flow channel prepared for successive flow of material, either of the same type or a differing composition. The flow and direction of a chemical purging agent may be selected for and controlled by a remanent magnetization valve as disclosed herein. Cyclic cleaning with a chemical purge is one viable strategy, perhaps in concert with the other listed options, for automated cleaning of deposition build-up in a multi-flow channel.

In addition to thermal and chemical methods, internal deposition may be dealt with by kinetic means as in FIG. 5 (F) which shows deposition cleaning by electromagnetic shuddering of the channel while undergoing gas flow. It should be noted that thermal, chemical and kinetic methods described herein may be used individually or in combination. As disclosed, a multilayer channel could consist of a rigid external channel which supports a solenoid winding and a loose flexible internal channel with magnets staggered lengthwise and radially along the exterior of the internal channel. When exposed to the field produce by an AC signal through the solenoid the shuddering of the channel can physically contribute to the removal of deposited molecules or atoms from the channel interior. In combination with flow through the channel as it undergoes high intensity vibration, deposition may be ejected from the channel in preparation for other flow materials. An AC signal produces sufficiently violent shuddering of the internal magnet-affixed tube to loosen deposition build-up. In the case of scent delivery, combination with unscented gas flow through the multi-flow tube, regular shuddering could restrict scent cross contamination.

FIG. 5 (G) schematically depicts a pre- or intermittent-heating mechanism for cleaning system components. Occasional comprehensive or intermittent internal cleaning of one or a combination of a scent delivery system's pressurization chamber(s), valves, container(s), and any other chambers with which scent streams interact may be accomplished by the incorporation of a heating mechanism at the intake of a scent delivery device. Sufficiently heating gas flow through all or a portion of the device acts to remove any deposition buildup throughout the device, but in particular is useful for those parts which are not already actively cleaned (e.g. by a multi-flow channel). Occasional comprehensive or intermittent internal cleaning of one or a combination of a fluid delivery system's pressurization chamber(s), valves, container(s), and any other chambers with which fluid streams with differing compositions (such as multiple streams with individuated scented gases) interact may be accomplished by the incorporation of a heating mechanism at the intake. In typical applications this cleaning hardware and method would be paired with an exhaust valve prior to release as in FIG. 4 (W).

Examples of Devices and Methods for Generation of Nano-bubbles, Nano-mist, and Scented Gas Orthonasal drug delivery, an intranasal administration of lipid-soluble or water soluble medications, is gaining popularity for ease of drug absorption. For example, for some children frightened by the use of hypodermic needles or for patients with whom the intravenous access to inject a medication is difficult, the orthonasal drug delivery is a convenient alternative route. A mouth-based breathing route may also be utilized, sometimes in combination with the intranasal route (insufflation). The orthonasal drug delivery is accomplished by inhaling of a vapor, mist, gas, or powder into a body cavity of the nostril channels. Many respiratory drugs for treatment of lung problems such as asthma or emphysema or some medications for allergy problems, are delivered through the orthonasal route. Some recreational drugs or entheogens are also delivered this way.

One of the important aspects to note is that orthonasal drug delivery often induces much faster onset of drug effect than orally administered medication delivery, with the bioavailability usually higher than oral administration. This bioavailability is caused by the quick absorption of drug molecules into the bloodstream through the soft tissue present in the mucous membrane of the sinus cavity and portal circulation bypass. As some drugs can have a higher rate of absorption, and are thus more effective in smaller doses, through this route. Some particular drugs have been manufactured in such a way that they need to be metabolized by liver before they get absorbed by the GI tract for systemic circulation, and such drugs should not be administered by the orthonasal route.

Another important aspect to note is that the orthonasal or intranasal route administration of medications through the nose can allow certain drugs and molecules to bypass the blood-brain-barrier (BBB) via diffusion through the olfactory epithelium and the perineural sheath or via retrograde axonal transport along olfactory and trigeminal nerves. The latter process probably implies endocytosis of the molecules, i.e., the human body cells engulfing and absorbing large polar molecules that cannot pass through the hydrophobic plasma or cell membrane. Many drugs such as for treatment of Alzheimer's disease (AD) cannot effectively be absorbed by the brain neural cells because of the BBB problem. Orthonasal drug delivery can thus be a convenient alternative method of delivering such medications to human body, so as to allow the brain to access high concentrations of drugs in the olfactory bulb (a neural structure which transmits smell information from the nose to the brain) that diffuses to the brain.

The scent delivery mechanisms and technologies disclosed in this document can also be utilized for efficient and well controlled drug delivery through orthonasal route described above. The drug delivery using the scent delivery mechanism in this document can administer drugs in the form of mist droplets (uniformly distributed in less than a micron in diameter), vapor, gas, or powder or other suspension. In addition to the advantages for efficient scent delivery, formation of mist, or preferably nano-dimension mist for more efficient drug absorption is an advantageous use of some of the disclosed embodiments.

FIG. 6 (A) depicts coated or hollow porous micro-/nanoparticles for fragrance ingredient retention, optionally with magnetic particle activation: Coated micro- or nano-particles allow for the high surface area to volume ratios necessary for scent delivery. Moving to hollow, porous particles allows for longer play durations while retaining the high surface area advantage. Inclusion of magnetic inner particles permits activated release via exposure to an alternating electromagnetic field to agitate the magnetic particles. As the magnetic particles are accelerated and decelerated by the alternating field within the particle interior, momentum imparted to the scent molecules serves to raise the substance temperature, driving up vaporization through the nano-porous or micro-porous surface as well as to eject scent material from the pores.

FIG. 6 (B) schematically illustrates a cross section of a container divided into separate compartments, useful for long-term applications in which contamination or oxidation may be an issue. In this design, a liquid ingredient reservoir is included to periodically or continually replenish the adjacent scent substrate. Transfer from the liquid chamber may be accomplished by capillary action, pressurization, or similar. As depicted, three transfer channels allow liquid to flow from the reservoir to the high surface area scent substrate. Additional channeling may be added to sufficiently supply the substrate.

FIG. 6 (C) schematically illustrates a cross section of a divided container, useful for long-term applications. In this design, a liquid scent ingredient reservoir is included to periodically or continually replenish the adjacent scent substrate consisting of porous, hollow, branched channeling. Inclusion of pores on the small or large channeling allows for high surface area exposure of the liquid ingredient base. Transfer from the liquid chamber may be accomplished by capillary action, pressurization, or similar. As depicted, three levels of branching distribute liquid across the substrate. Additional branching nesting, levels, angles, extensions, etc. may be employed to increase surface area of scent substrate to maximally scent air (or other gas) as it flows through the chamber from inlet to outlet.

FIG. 6 (D) schematically shows a device for dispersing microscale/nanoscale droplets via pressurized distribution of a fluid through a patterned plate with hydrophobic/lipophobic/omniphobic coating on the egress face with droplets being dispersed into a transverse flow of air or other gas. The use of hydrophobic/lipophobic/omniphobic coating enhances the release of mist droplets or vapor bubbles much easier from the mist-generating or vapor bubble-generating structures, according to some embodiments. The patterned plate may be produced with microscale or nanoscale pores using any convenient manufacturing technique such as AAO (Anodized Aluminum Oxide) self-assembly followed by etching, photolithography, nanoimprinting, etc. Surface tension forces prevent unpressurized fluid (e.g. medicine) leakage through the pores and surface coating/treatment on the posterior of the plate prevents surface wettability from depleting the reservoir following release. To accomplish nebulization, pressure is applied to the fluid reservoir by a plunger (either manually or machine-aided) to force small streams/droplets of liquid through the patterned plate and into the transverse air/gas flow. Droplet size may be controlled by altering the dimensions or geometry of the plate pores and/or varying the velocity of the transverse flow. Use of nano or micro dimension mesh or pore structures are useful for generating smaller, sub-micro or nano bubbles and mists. Alternatively, utilizing surface structures alone such as a roughened or patterned or grooved or holed or textured or wire-mesh surfaces can be employed to generate smaller bubbles, with the textured or roughened surface dimension preferably less than 10 µm, more preferably less than 1 µm, even more preferably less than 0.1 µm in width, hole size, or filament spacing. Such surface structure can be induced by mechanical sand blasting, lithographical patterning, chemical or electrochemical etch patterning, surface anodization, RF texturing for surface nanowires, or physical attachment of premade nanowires, nanomesh layer, nanopowder layer, or membrane material onto the surface. Drop separation may be promoted via resistive heating, inductive heating, or use of catalytic surfaces.

Both 3-D or 2-D surface structures of nano or micro dimension mesh or pore structures or roughed surfaces can be optionally heated by e.g., electrical current for resistive heating to further accelerate the bubble/mist formation. Metallic structures are preferred to ceramic structures to perform resistive heating. The extent of heating can be either above the boiling temperature of the liquid involved to actively increase the rate of bubble formation, or can be to somewhat below the boiling temperature to simply enhance the kinetics of bubble formation.

Another embodiment of mist generation is depicted in FIG. 6 (E) which describes a device for dispersing microscale/nanoscale droplets via three-dimensional mesh with a hydrophobic/lipophobic/omniphobic surface which is shaken by mechanical connection to a surrounding piezoelectric material activated in a high frequency range. A microscale or nanoscale mesh with hydrophobic, lipophobic, or omniphobic coating or surface treatment promotes the formation of nanoscale bubbles and cavitations in the interspersing fluid. High frequency vibration of the mesh by piezoelectric activation of a surrounding element produces droplet ejections into the transverse flow above the reservoir. Locating the mesh at the surface of the reservoir efficiently nebulizes the liquid with droplet size being influenced by frequency and scale of the mesh. In FIG. (E) embodiment, drop separation may be promoted via resistive heating, inductive heating, or use of catalytic surfaces.

For vaporization as opposed to nebulization, FIG. 6 (F) schematically illustrates a device for continuous uptake of a fluid via microbubbles/nanobubbles held separate by nanoscale lengthwise filaments as vapor flows through the liquid containment chamber. Two patterned plates with nanoscale or microscale pores as produced by AAO self-assembly and etching or similar process are utilized to contain a liquid but permit gas flow through the container. Micro- or nano-bubbles are guided through the reservoir and kept separate by a lengthwise array of filaments. In some embodiments, microscale or nanoscale filament guides optionally with hydrophobic, lipophobic, or omniphobic surface treatment, preferably with a droplet contact angle of >100 degree, more preferably >130 degree. Minimizing bubble size and maximizing quantity results in a high surface-area to volume ratio and optimal vaporization of the fluid into the resultant stream of scented or loaded vapor.

For fully solidified, high-concentration applications, FIG. 6 (G) schematically depicts a scent ingredient specific, solid or semi-solid, interconnected, and nonporous media allows for extended lifetimes and miniaturization. Alternative gasses may be employed (Nitrogen, Argon, Etc.) to limit oxidization, or to alter olfactory rendition or impression. Vaporization of the scent ingredient may be accelerated by exposure to higher temperatures. The treatment may be useful to promote hydrophobic, lipophobic, or omniphobic surfaces on the filament array may further promote bubble formation.

Examples of Devices, Features, and Methods for Comfort or Enhanced Scent Experience In a number of possible applications, the scent devices of the present document are intended for extended periods of use, whether in conjunction with the contemporaneous presentation of media or otherwise. In this light it is important to take into account the human (or, as appropriate for use, animal) biological and neurological makeup to ensure scent delivery can be comfortably presented for extended durations. For example, the individual or sequential presentation of scented gases with varying duration comprised of variable gas concentrations and molecular ingredients must be taken into account. Comfort and hedonics of use must also be taken into account if the user experience is to be viable, desirable or optimized.

Further, scent delivery to users can help optimize experience with or without media, or be used to create new or other desired user sensations and reactions with or without media. The presentation of scent may be accompanied by sound or music or synchronized or paired with other media, whether in readable format, in images or sound separately or audiovisual format, touch media (e.g. haptics), taste media (e.g. foods), or media of any other kind or combination. When presenting the sense of smell in conjunction with other sensory, broadcast or communication media, the intermodal effects between the human senses can enhance or modify experience and perception. For example, the dramatic elements of a story, whether presented in book or movie format, can be heightened or colored by presentation of appropriately selected scents. Leitmotifs of scents can be programmed for release in or between scenes of a film (or videogame) to remind the audience of previous action or elements of the story, much as musical leitmotif might be used in a film soundtrack. Realistic characters, or avatars, can be associated with their individual smells. By way of further example of intermodal interplay, in therapeutic applications chronically or terminally ill patients who may have little taste could be induced to eat through delivery of scents (and flavors) specially designed to augment taste and the improve the hedonics of a specific food he or she is eating.

With specific reference to VAR applications, the sense of smell is a critical sensory dimension required to experience total immersion (i.e., a complete sense of realism and presence in a remote environment). However, the ad hoc presentation of scent without accompanying appropriate realistic dynamics can have the opposite effect—to trigger the brain's jarring awareness of its artificial introduction, thereby inhibiting the sense of presence. For example, the smell of a virtual object could be presented to or experienced by the user without inappropriate intensity given either the nature of the object or its visually perceived distance from the user, thereby destroying the illusion of reality.

Additionally, a system that can monitor and synchronize delivery to a user's breathing (intake or pattern of intake) can reduce unnecessary scent delivery and thereby increase the efficiency of scent devices and lower costs of use (of amount of scent ingredients) in scent devices or cartridges. Other biological sensors can adjust scent delivery to accommodate user comfort or accentuate or modify user experience, or the perceived content of live, 2D, 3D or VAR media he/she is experiencing.

Features of the device embodiments to enhance, modulate, modify or optimize the user's experience may include:

FIG. 7 (A) schematically depicts the inclusion of a humidifier into a scent delivery device prior to output to introduce moisture into scented gas delivery or alternatively delivery moisturized (unscented) gas directly to the user's nosespace. Such a humidifier may be always activated during device use, or selectively or automatically activated via sensor or programming. Moisturizing the nose space (e.g. the inner lining or epithelium of the user's nose as well as the user's lips) is critical to avoid irritation and maximize user comfort, or may be also used to modify or enhance the user impression of type, characteristics or qualities of a scent being delivered, or the media accompanying or synchronized to scent delivery. The embodiment may be useful to avoid unpleasant chapping of lips or nostrils from an extended use duration of a scent delivery device. The humidifier may be optionally included prior to scent output. Such humidifier may be always activated, manually activated, or sensor activated.

FIG. 7 (B) schematically depicts the inclusion of a heating unit alongside the delivery channel to increase the temperature of a scented gas. Such a heating mechanism may be selectively or automatically activated via sensor or programming using resistive or inductive heating. A heating mechanism can be used to heat device intake air in an outside, cold environment for user comfort, or alternatively, used in any external environment to modify or enhance the user impression of type, characteristics or qualities of a scent being delivered, or the media accompanying or synchronized to scent delivery.

FIG. 7 (C) schematically depicts the inclusion of a thermoelectric cooling unit alongside the delivery channel to cool the temperature of a scented gas. A cooling mechanism can be used to cool device intake air in an outside, or a hot environment, for user comfort, or alternatively, used in any external environment to modify or enhance the user impression of type, characteristics or qualities of a scent being delivered, or the media accompanying or synchronized to scent delivery.

FIG. 7 (D) shows the inclusion of a blending valve, as in FIG. 3 (H) to vary volume (intensity) of scent during scent delivery by controlled dilution of the scented gas stream with a stream of unscented gas. Volume/intensity may also be controlled by varying the pressurization level, duty-cycling the remanent magnetization valve activation, or changing the ingredient loading levels within the fragrance ingredients container. Depending on the particular hardware configuration all or any combination of these intensity control measures may be employed. For example, in a configuration with the scent cartridge positioned directly beneath the nose as in FIG. 4 (B)-(D) or similar, intensity would be controlled by some combination of pressure level, duty cycling, cartridge ingredient concentration, temperature and the inclusion of a duty-cycled unscented gas stream. For individual scented gas delivery through a single multi-flow channel as in FIG. 5 (B)-(F), volume control could be accomplished by some combination of controlled pressurization and a blending valve to controllably dilute the scented gas with unscented gas prior to the delivery channel. For delivery of mixed or coupled ingredients in a scented gas as in FIG. 3 (A)-(F), volume control could rely on the combination of pressurization, duty-cycled ingredient activation, temperature, varied liquid/solid ingredient concentration levels within the cartridge containers, and dilution of the mix of scented gases with a controllable volume of unscented gas. Volume adjustment can be manual (adjusted by user), automated or programmed to vary according to the level desired, or designed (to vary) with accompanying media or activities.

FIG. 7 (E) schematically depicts an operation in which a single scented gas stream is separated into two (or more) tubes (or channels) that are directed into the nose space or, in the case of two channels, can be directly placed at the base of the nostrils for scent delivery. At the time and for the duration of scent delivery either (i) one or more channels may be closed while the other(s) stream (deliver) scent, or (ii) any combination of channels may programmably deliver the same or different scents in specified combination, in the same or specified varying concentrations, either continuously or stepwise in concentration and/or timing.

The ability to deliver differing or variable concentrations to individual nostrils during presentation of media (i.e. a movie, videogame or advertisement) can facilitate 3D perception of the scent location and depth in the media space being presented. For example, one may wish to render (match) a smell of an object or character of a videogame that/who is situated to the left from the user's standpoint—delivery only to the left nostril, with intensity to match perceived distance and location from user can be calibrated to impart the impression that the smell suitably appears to be emanating from the object to the left of the user in three dimensional space.

The ability to deliver varying scented gases (and concentrations thereof) in each or any combination of delivery channels gives the device the further option to programmably mix (more limited) ranges of scents or scent accords combinatorially in the nosespace to provide special effects or more rapidly produce certain scent compounds.

FIG. 7 (F) shows the feedback mechanism enabled by the incorporation of a camera or other sensors into a scent delivery device to observe the user's physical state during operation that captures and records (i) topological features of the face, neck or other exposed parts of the body (including skin and its surface features such lines or wrinkles (and their deformations) and emission of heat), (ii) head pose, body posture or movement, (iii) individual body features such as hands and their movement or position, etc. Device software that interprets moving or still image(s) of the user can identify user emotion, behavior, intention, or nervous system state, as well as patterned tendencies of the foregoing, and can be programmed to activate the selection, generation and delivery to the user of (iv) scents from a ready-made scent container in a scent delivery device scent cartridge; or can otherwise can be programmed to (v) select, a labeled formula (containing a list of ingredients, parameters such as molar weights and specifications for blending and for release such as concentration) and instruct the delivery device to selectively blend the formula's compound for release and delivery to deliver to the user. The software may optionally send instructions to trigger the operation of other sensory generating mechanisms (such as heating, cooling, or moisturizing), while delivering the aforesaid selected blended scent compound (or ready-made scent as the case may be), in order to further enhance or modify user experience and perception. For example, whilst playing a videogame, a user's features may be captured on camera and interpreted by the device's software that the user is exhibiting anxiety. The software might be programmed to automatically trigger the device's cooling feature to lower the scent delivery temperature and thereby induce a calming influence on the user. The embodiments may include a camera/sensors (or link to one in VAR device) for optical/motion capture and detection of facial features and expressions, movement of the head or body (to interpret emotion as well as to use for interpretation of the distance and location in 3D virtual space of a scent from the user, and breathing (the last of which can be used to synchronize scent delivery to an individual's breathing or breathing cycle).

FIG. 7 (G) presents a schematic overview of the inputs, decisions, and outputs which may be incorporated into a scent delivery device for enhanced, modified or optimized user experience. Basic layouts of software inputs, functions, and outputs for a fully functional, responsive, integrated scent delivery device which actively or programmatically adjusts scent outputs according to user feedback, virtual or digital media and/or user(s) interactions, interactivity or exchanges, and designed parameters is shown. The following sections address various approaches to scent delivery interactions.

FIG. 7 (H) shows example embodiments for consumers, commercial or other types of users may design new scents or programmatically select scents from a database drawing from tabulated formulae, chemical parameters, and pertinent regulatory restrictions (i.e. restricted use of chemicals or chemical concentrations for delivery) for wired or wireless instructions (transmission) to other user devices with compliant software to trigger timed or real-time blending or container selection and device release. Instructions may be transmitted from one or a group or users to others for purposes, for example, of (i) digital sharing or exchange of scents (ii) synchronization with the play of scented media of any type (e.g. with books, email, films, videogames, music, etc.), (iii) for online shopping, and so forth. Programmatic interpretation of descriptions, content, user state, environment, social, psychometric, and chemical blending parameters enable programmatic or automated digital scent creation and transmission and interaction between users, optionally in conjunction with transmitted audiovisual or other media, Scented Virtual, Mixed or Augmented Reality ("VAR") Data, Communications, Sensors and Signals Scent devices may be attached or integrated into VAR devices. A scent device's software, hardware and/or electronics may be enabled to communicate with or transmit data between it and its companion VAR device to permit scent device reception and interpretation of light field array, waveform, VAR camera, laser, tracking, motion capture, music and other VAR media data or user data. The scent device software may be programmed to read and interpret the aforesaid VAR data that is received and trigger selective activation, generation and delivery of scents in response to or coincident with VAR user activity or experiences.

VAR Media

Some embodiments may be attached or integrated into VAR devices. A scent device's software, hardware and/or electronics may be enabled to communicate with or transmit data between it and independent media streamed to the VAR device (e.g. videogames, movies, simulators, instructional or training videos, etc.). The scent device software may be programmed to read and interpret the media data and trigger selective activation, generation and delivery of scents in response to or coincident with VAR user behavior or other response or experience. Alternatively, the scent device software may manually, automated or programmably transmit data to the VAR device with operation instructions or transmission data for the purpose of altering, superimposing, enhancing or otherwise modifying the independent media being transmitted to the user during scent delivery.

External Environment Sensors and Transmission

Some embodiments may be enabled to receive signals and information from external wired or wireless sensors and transmission devices such as laser or other optical or wireless beacons. Said signals can activate and/or instruct scent device software for timed scent generation and delivery. The devices may also separately or reciprocally transmit data, using suitable software and communications interface, to transmission devices or sensors. For example, a food product in a grocery store with sensor might automatically or programmably activate the user's scent device to generate and deliver a specified scent of a food while the user picks up that food product from the shelf. By way of further example, the sensor or transmission device might trigger activation of a perfume video advertisement on a store display screen as a user approaches a display, while simultaneously activating the user's scent delivery device and transmitting data to it to select, generate and deliver, synchronized to specific elements of the advertisement, the smell of the perfume brand being advertised. In this last example, the smell of the cologne of an actor could be activated for release to the user at the moment the actor appears on screen and switch off the moment he departs the scene.

Speech Recognition

Auditory signals may also be used to selectively, automatically or programmatically trigger scent activation, and vice versa. Speech recognition mechanism may also be employed. Additionally, software that programmably coordinates the pairing of key words/phrases and/or sound (including without limitation the sound of breathing) dynamics with release of scent counterparts may be implemented. In particular, scent delivery may be optionally activated in response to sniffing/inhalation from the nose.

Scent Transmission between Users

The scent devices and software disclosed in the present document may enable one or a group of users to share or transmit scents (alone) or scented media (such as scented photos, emails, voicemail, video, sounds, music, songs, stories, or other scented media of any kind), with other users via internet, cell phone, VAR device or any other communications or broadcast hardware, application, program, interface (including media interface such as a website) and/or software. For example, personal users might post or share scented pictures of their respective holidays with each other via Facebook, or send scented emails to each other, etc. FIG. 7 (H) provides a layout of scent delivery transmission.

Companies or other third parties (whether commercial, governmental, military, institutional or organizational) may wish to transmit scented media to users of devices disclosed herein using compatible software for various purposes. For example, a travel agency may wish to digitally transmit a scented brochure or video of a tropical resort to users for advertising purposes. By way of further example, beauty internet shopping sites might wish to digitally transmit scented images of perfumes to users while advertising special offers. Another example includes Alzheimer's patients whose doctor might use the delivery device's API to program scent release tagged to simultaneously transmitted images of his children to assist in restoration of his memory and recognition of them.

Scent Creation

Some embodiments may also enable a single user or multiple users in collaboration to create perfumes, fragrances used in bath and other beauty products, or scents designed for scented travel videos, scented movies, scented videogames or other media, or scents for other purposes.

Users may be professional or non-professional. For example, professional perfumers might use the devices disclosed herein to create perfumes for retail sale, or scents for a client travel agency's scented brochure. Non-professional users might create perfumes or other scents for personal use or to digitally share or exchange with other users.

Programmatic Assistance for Scent Creation and Transmission

To ease scent creation, and sharing or other interaction involving scent, users may use the delivery device's software (such as an API) to search its database by keyword such as name of scent ingredient or, scent accord labels, or other descriptions, chemical parameters, etc. The scent delivery device's information database and categories may comprise: (i) fragrance and flavor ("scent") formulae with labels and accompanying descriptions of smell (ii) link of formulae with associated scent family, chemical structure or other user or system defined categories; (iii) chemical ingredients (and their constituent elements and parameters such as molar weights, etc.) (iv) restricted or upward bound of concentrations of each or a combination of ingredients; (v) database of IFRA/legal/governmental guidelines for or restrictions on use of chemicals for scent delivery or application. To further aid scent creation and transmission, the scent delivery device or software may include:

the capability to interpret user descriptions and instructions involving hedonics and psychophysical descriptions of or reactions to smells and to programmably generate formulae for automatic or timed scent generation and delivery;

the capability to passively interpret, record and retrieve content and dynamics of audio, visual, audiovisual or other multi-media or multisensory content (or digital or other broadcast data) presented (live or digitally) to user, and to programmably generate formulae for automatic or timed generation and delivery of scents synchronously or asynchronously with the content;

the capability to interpret, store and/or transmit user data such user facial, body and pose or motion capture and breath inhalation/exhalation pattern to programmably generate formulae for automatic or timed generation and delivery of scents to user;

the capability to interpret external wireless or wired signals and instructions for automatic or timed activation of fragrance compounding and delivery to user or among users;

the capability to interpret (digital or live) social interactions among users and programmably select to generate formulae (for rule-based or defined purposes) and timed delivery of scents to users;

the capability to digitally share any user data (including user's fragrance and flavor database) with other users' compatible devices;

and the capability to enable other users or third parties (e.g. companies) to send instructions to user's software to programmably generate formulae and timed generation and delivery of scents to one or more users.

Haptic Scent Activation

Some device embodiments described herein may be used in conjunction with haptic technology that operates to impart the impression of the sense of touch during interaction between users while using VAR or other media. The scent devices might be triggered by the haptic software or hardware operations, or, alternatively, the software of the scent devices may be programmed to interpret haptics functions or operations or signals to programmably activate and select scents or sensory features for scent delivery to modify or enhance the perception of touch or the attendant media. For example, during a virtual reality videogame, the player with haptics controllers might experience increasing force feedback whilst attempting to (virtually) push a rock up hill. A scent of sweat might be synchronized with haptics operation to increase in intensity the harder the user pushes the rock.

Flavor/Taste Activation

Some device embodiments described herein may be activated to deliver flavored gas—optionally in conjunction with release of other device sensory features such as moisture—to the user during eating to enhance, modulate, improve or modify perception of taste. For example, whilst physically eating a custard desert, the mouthfeel or perception of custard texture might be enhanced with the selective release of moisture.

The scent devices may also be activated to deliver flavored gas or mist whilst a user experiences smells of foods or beverages or other objects that can impart impression of taste whilst immersed in VAR media. For example, the scent device of a user in a VAR environment who is virtually attending a cooking show might be programmably activated for synchronous scent delivery of the flavors of bacon being virtually cooked. In this example, scent intensity might optionally be increased in sync with the sound of increased sizzling of the bacon as it is cooked.

Breathing Interval or Pattern Recognition

Some device embodiments described herein may incorporate a camera to measure swelling of an individual's chest (or clothing covering it) or detect signals from a wearable sensor, to determine the user's real-time or recorded inhalation and exhalation. Media or third party applications with suitably compatible software may be enabled to programmably select specified scents for scent generation and delivery timed to breath interval or pattern during the use of the media or applications. Alternatively, device programming may interpret third party media or software to programmably select scents for scent generation and delivery during streaming of or the interaction with media. For example, a scented (war) videogame might be programmed to trigger a sulfurous scent release and delivery to the user when the user launched a shoulder-fired rocket and destroyed a nearby enemy tank.

Device software may also be programmed to time scent delivery only during intervals of breath inhalation and cease delivery during exhalation for most expedient use of scent material, for example, as depicted in FIG. 7 (I). Active monitoring of a scent device user (e.g., his/her audio, body position, reactions) allows for a programmatic determination/estimation of their respiratory waveform. Knowledge of the anticipated or real-time intervals between delivery activation and perception (accounting for device geometry, human perception, and switching time) allows for output adjustments such that scent is only supplied during breath intake (inhalation). Further dynamic adjustments incorporate 3-D delivery, motion adjustments, and blending formulae.

Using the technology described herein, for example, as discussed with respect to FIG. 3(A) to 3(H) and FIG. 7(A) to 7(I), a digitally controllable scent creation and delivery apparatus includes an array of containers (e.g., containers holding ingredients 306), each container having an inlet through which an input carrier gas flows in, a chamber, called a scent container, for holding a material containing an elementary or a base chemical producing a characteristic odor, called a scent ingredient, or an ingredient, and an outlet through which a mixture of the input gas and the scent ingredient flows out, a flow regulation mechanism (e.g., one or more of valves 306, 308) that controls gas flow through each container based on electromagnetic signals, one or more blending chambers coupled to outlets of the containers and having a delivery channel outlet, the blending chambers (e.g., 310) allowing individual outputs from the outlets of the containers to blend together homogeneously to generate a pre-determined scent and flow the pre-determined scent out through the delivery channel outlet, and a pressurization chamber coupled to inlets of the containers, and generating the input carrier gas flows.

In some embodiments, digitally controllable device for dispensing a scented gas, vapor, or liquid substance includes a cartridge structure that includes one or more containers, each containing a scent ingredient, scent composition, drug or other scented or unscented substance, a housing structure that includes a compartment to hold the cartridge, an opening to allow the one or more substances to dispense to an outer environment from the device, and one or more transporting channels formed between the compartment and the opening, wherein each of the one or more transporting channels is configured to deliver a substance from the corresponding container to and through the opening, and an actuator switch arranged in a corresponding transporting channel and operable to move between an open position and a closed position based on an applied signal to selectively allow passage of the scented substance from the corresponding transporting path.

In some embodiments, for example, as described with respect to FIG. 1(A) to 1(L), a valve for controlling flow of a fluid includes a flow channel allowing passage of the fluid, the flow channel having a first portion (e.g., lower portion 121) and a second portion (e.g., upper portion 123) separated from the first portion by a hard or soft seal having an opening, the first portion having an inlet for a fluid to enter the flow channel and the opening allowing fluid to enter the second portion, a magnetically moveable pin positioned in a channel in the valve, the pin moveable along the channel into a closed position in which the pin is magnetized and closes the opening, thereby disallowing the gas to flow from the first portion of the flow channel into the second portion of the flow channel and an open position in which the pin is demagnetized and separated from the opening, thereby permitting the gas to flow from the first portion of the flow channel into the second portion of the flow channel, and a solenoid located on an exterior of the valve in a region corresponding to the pin such that an electrical current through the solenoid in one direction controls the magnetization and thereby the position of the pin between the closed position and the open position, wherein the pin is further moveable from the closed position to the open position by having the gas under sufficient pressure to move the pin along the guide.

In some embodiments, for example, as described with respect to FIG. 1(A) to 1(L), a digitally controllable valve apparatus for controlling flow of a gas, vapor or a liquid substance includes a housing having a high permeability plate with a through-hole on one end and a back plate with one or more through-holes at another end, a remanent magnetization pin positioned in an interior of the housing and able to move back and forth between the one end and the another end such that when the pin is magnetized it moves to the one end, the pin makes contact with the high permeability plate, thereby closing the through-hole and disallowing passage of a gas or a vapor or a liquid substance through the housing, and when the pin is demagnetized it moves away from the one end towards the another end, the pin allows passage of the gas or the vapor or the liquid through the through-hole, the interior of the housing and the one or more through holes at the another end, and a solenoid on an exterior of the housing, the solenoid being able to carry electric current to cause magnetization or demagnetization and subsequent movement of the pin between the one end and the another end.

In some embodiments, for example, as described with respect to FIG. 2(A) to 2(C), a check valve apparatus includes a planar ring comprising a ring material surrounding an opening at a center thereof, and a flap made of a flap material affixed to the ring via at least one hinge, wherein the flap is moveable around the hinge at least in a closed position in which the flap stops passage or leakage of a fluid through the opening and an open position in which the flap allows the fluid to escape via a gap between the flap and the planar ring through the opening. A magnetic attraction force between the ring material and the flap material acts to move or hold the flap in the closed position and an air flow force pressing against the flap acts to move the flap in an open position.

In some embodiments, for example, as described with respect to FIG. 3(H), a mixing or dividing valve apparatus includes a three channel housing, with each channel in the same plane and an axially symmetrical open central chamber at the meeting of the three channels such that the axis is orthogonal to the plane containing the three channels, a radially positionable blocking wedge located within the central chamber and rotatable around the central chambers symmetric axis, a high permeability mating piece embedded into the blocking wedge and positioned adjacent to valve exterior, an arced array of magnetically latchable pins wound in solenoids positioned exterior to the valve which is magnetized or demagnetized by electromagnetic signals, wherein the angular position of the blocking wedge about the central chamber axis is determined by the magnetic attraction force between the embedded high permeability mating piece and the magnetized external latchable pin and serves to direct flow from a first channel to a second channel, to a third channel, or to split flow between the second and third channel with the proportional amount determined by the radial position of the blocking wedge, or alternatively to permit flow into the first channel from the second channel, from the third channel, or to combine flow from both the second and third channels with the proportional amount determined by the radial position of the blocking wedge.

In some embodiments, for example, described with respect to FIG. 4(A) to 4(V), a digitally controllable scent creation and delivery apparatus includes an inlet port from which air enters the apparatus, an outlet port from which a pre-determined scent flows out of the apparatus, an arrangement of a pressurization mechanism, remanent magnetization valves and scent containers that hold scent ingredients wherein the arrangement comprises, from the inlet port to the outlet port, a cascade from one of: the pressurization mechanism followed by the remanent magnetization valves followed by the scent containers, the pressurization mechanism followed by the scent containers followed by the remanent magnetization valves, the scent containers followed by the remanent magnetization valves followed by the pressurization mechanism, the remanent magnetization valves followed by the scent containers followed by the pressurization mechanism, the remanent magnetization valves followed by the scent containers followed by a second set or remanent magnetization valves followed by the pressurization mechanism, or the pressurization mechanism followed by the remanent magnetization valves followed by the scent containers followed by a second set or remanent magnetization valves, wherein the pressurization mechanism forces air out of its output and where the remanent magnetization valves control airflow by selective opening of the valves using electromagnetic control signals.

In some embodiments, for example, described with respect to FIG. 4(A) to 4(V) and FIG. 8, a method 800 of delivering a digitally controlled scent-enhanced multimedia experience includes delivering (802) a non-olfactory sensory stimulus such as sound, visual and/or other stimuli to a user, controlling (804) a synchronous delivery of a scent stimulus from a scent device by an electromagnetic control signal that controls scent activation, scent blending, release and delivery to a user, delivering (806) the scent stimulus to the user wherein the scent stimulus is related to the non-olfactory stimulus and enhances, augments, modifies, alters or integrates with user experience of the non-olfactory stimulus, delivering (808) the scent stimulus to the user wherein the scent stimulus is related to the non-olfactory stimulus and the user is engaged with the non-olfactory stimulus passively or actively, or interactively, and selectively delivering (810) the scent stimulus to the user wherein the scent stimulus is related to the non-olfactory stimulus, while the user is engaged in an activity.

In some embodiments, for example, as described with respect to FIG. 6(A) to FIG. 6(G) and FIG. 9, a method 900 of generating mist of a scent ingredient includes storing (902) a scent ingredient in a liquid form in a reservoir having at least one porous side that allows controlled escape of the scent ingredient in a particulate form, causing (904) the scent ingredient to escape the reservoir in the particulate form through the at least one porous side into a flow chamber, controlling (906) airflow through the flow chamber to achieve a desired separation of the scent ingredient in the particulate form into a mist comprising scent particles, and outputting (908) the mist form at an outlet of the flow chamber.

In some embodiments, for example, as described with respect to FIG. 6(A) to FIG. 6(G), a mist generation apparatus includes a reservoir that stores a scent ingredient in a liquid form, the reservoir having at least one porous side that allows controlled escape of the scent ingredient in a particulate form, a mechanism that causes the scent ingredient to escape the reservoir in the particulate form through the at least one porous side into a flow chamber, a flow chamber for allowing air to flow to achieve a desired separation of the scent ingredient in the particulate form that has escaped from the porous side into a mist comprising scent particles, and an outlet for outputting the mist from the flow chamber.

In some embodiments, for example, as described with respect to FIG. 7(A) to 7(I) and FIG. 10, a method 1000 of digitally controlling a scent delivery array comprising a plurality of remanent magnetization valves that control release of scent ingredients from containers includes repeated turning on and off (1002) of the remanent magnetization valves, causing (1004) pressure of release of the scent ingredients to vary, metering (1006) dilution of the scent ingredients by mixing with unscented gas; modulating carrier gas temperature (1008) thereby blending and controlling (1010) concentrations and ratios of scent ingredients; and causing (1012) a desired scent to be delivered from the scent delivery array.

In some embodiments, for example, as described with respect to FIG. 7(A) to 7(I) and FIG. 11, a software implemented method 1100 of providing customizable olfactory experience includes storing (1102), in a searchable database, including without limitation, scent descriptions and labels ingredients and accompanying formulae, chemical parameters, consumer or individual data preferences, tastes and perception, and/or regulatory restrictions, limitations, parameters or conditions governing use or delivery to user of scent ingredients or compositions, receiving (1104) an input signal indicative of an event for which a particular scent is requested, deriving (1106), at least based on the searchable database, scent creation, generation and delivery information for the input signal, and operating (1108) a digitally controllable scent delivery apparatus comprising an array of scent containers, a flow regulation mechanism, a mixing chamber and a pressurization chamber to generate and deliver the particular scent.

In some embodiments, for example, illustrated in FIG. 12, a method 1200 of delivering a substance to a target site includes providing (1202) one or more containers that hold one or more ingredients that make up the substance, wherein each container is fitted with at least one magnetically controllable valve, operating (1204) a control circuit to selectively actuate, based on a desired characteristic of the substance, at least some of the magnetically controllable valves, causing at least some of the one or more ingredients to mix in a pre-determined proportion, and delivering (1206) a resulting homogeneous mixture of the substance through an outlet placed in proximity of the target site.

In some embodiments, for example, as described with respect to FIG. 7 (E) and FIG. 13, a method 1300 of delivering digitally controlled scent-enhanced multimedia experience includes controlling (1302) delivery of a first scent stimulus from an array of scent containers by an electromagnetic control signal that controls release of scent ingredients from at least some of the scent containers in the array to a first channel, controlling (1304) delivery of a second scent stimulus from the array of scent containers by the electromagnetic control signal that controls release of scent ingredients from at least some of the scent containers in the array to a second channel, delivering (1306) a first mixture of the first scent stimulus and the second scent stimulus in a first proportion near a user's left nostril space, and delivering (1308) a second mixture of the first scent stimulus and the second scent stimulus in a second proportion near a user's right nostril space, where the first proportion and the second proportion are selected to enable a spatial scent experience by the user. For example, when a desired user experience is that the scent is coming from the user's extreme left, 100% of left channel may be mixed with 0% of right channel and delivered to the left nostril. Because the scent stimuli themselves may be composed of multiple distinct smell ingredients, a complex sensory experience that simulates simultaneous olfactory experience from multiple fragrant sources in multiple places may thus also be provided to the user.

Various disclosed embodiments and techniques may be described using the following clauses.

Clause P1.1—A magnetically latchable switch structure with gas flow spring instead of a mechanical spring as illustrated in FIG. 1B as this new structure is compact, simpler and more easily controlled than that of the devices described in the PCT application by the same inventors, application serial number PCT/US14/035054, entitled "SWITCHABLE GAS AND LIQUID RELEASE AND DELIVERY DEVICES, SYSTEMS, AND METHODS".

Clause P1.2—A magnetically latchable switch structure with non-cylindrical pin guide to facilitate gas flow, for example, as illustrated in FIG. 1D-1G, this structure is compact, simpler, and more easily controlled.

Clause P1.3—A method of using a cantilever spring separation of the magnetically latchable switch structure, e.g., as illustrated in FIG. 1G. This new structure is robust, orientation-independent, and compact.

Clause P1.4—A structure of a magnetically latchable switch that uses a pressure-based separation of the magnetically latchable switch structure, e.g., as shown in FIG. 1H. This structure is compact, orientation-independent, and simple.

Clause P1.5—A magnetically latchable switch structure that uses gravity-based separation for gas flow, e.g., as in FIG. 1I. This structure is compact, simple, and suitable for some fixed position applications.

Clause P1.6—A magnetically latchable switch structure with non-cylindrical solenoid/pin-guide, e.g., as illustrated in FIG. 1H. This structure is more efficient, compact, and simpler.

Clause P1.7—The magnetically latchable switch structure with dual solenoids separately responsible for valve opening/closing via magnetization and demagnetization (as in FIG. 10. This structure is more responsive and more easily controlled.

Clause P1.8—An X-Y or X-Y-Z matrix array of FIG. 1A-1I devices, for example, as in FIG. 1J-1L) for an apparatus having a large number, rapid and rapidly switchable, energy efficient, scented or unscented gas delivery capability.

Clause P1.9—A magnetically latchable switch structure with either single or dual flat spiral solenoids, e.g., as depicted in FIG. 1L, this structure is compact, manufacturable with typical lithographic processes, controllable, and responsive.

Clause P1.10—An X-Y or X-Y-Z matrix array of FIG. 1A-K devices, e.g., as in FIG. 1L-N. This matrix array is used for rapid and rapidly switchable, combination of a large number of scented or unscented gas ingredients for blending and delivery.

Clause P2.1—A magnetically closed check valve with magnetized ring and magnetic flap affixed via hinge, e.g., as in FIG. 2A. This check valve is compact, simple, and suitable for passive gas flow control applications.

Clause P2.2—A magnetically closed check valve with magnetized ring and magnetic flap affixed via hinge, e.g., as in FIG. 2B. This check valve is compact, simple, and suitable for passive gas flow control applications.

Clause P2.3—An array of FIG. 2A-2B devices (as in FIG. 2C) for passively managing flow for large number scent delivery capability.

Clause P3.1—An X-Y or X-Y-Z matrix array of FIG. 1A-K devices for timed, rapid blending and rapid, sequential delivery of a large number of formulae of unscented or scented gases, e.g., as shown in FIG. 3A-3F. The two or three dimensional array of magnetically latchable valve switches allow for convenient and rapid selection, generation, and delivery of desired scented or unscented fluids either individually or as homogeneous blends. Just one switch can be opened for one specific scented or unscented gas, or multiple valves can be activated simultaneously for combination of gases. The switch can be activated by wireless or hard wired signals with compatible software, so that a particular device is magnetized or demagnetized, and fluid flow is initiated or stopped.

Clause P3.2—Devices as in Clause P3.1 configured with individual remanent magnetization valves controlling each individual ingredient, e.g., as shown in FIGS. 3C & 3E.

Clause P3.3—Devices as in Clause P3.1 configured with remanent magnetization valves which may be aligned with ingredient containers via rotation or X-Y or X-Y-Z addressable motion of either the ingredient containing container or the valve housing, e.g., as shown in FIG. 3D.

Clause P3.4—Devices as in Clauses P3.1, P3.2, and P3.3 with gas flow passing through multiple layers of valves and ingredient containers sequentially or in timed fashion either in mirrored, stacked, or nested configurations, e.g., as shown in FIGS. 3D & 3F. This configuration enables miniaturization and accelerating blending of a large number of ingredients in a formula.

Clause P3.5—A latchable remanent magnetization blending or dividing valve with an exterior arc of magnetically latchable pins and a radially positionable internal blocking wedge with embedded high permeability mating piece, for example, as depicted in FIG. 3H. This design is energy efficient with passive latch positions, flow is fully enclosed, and provides for ratio control.

Clause P4.1—Devices containing magnetically latchable switch structures, as recited in Clauses P1, P2, and P3, that selectively activate the flow of gas through one or more containers with scented substrates or coated or other retention material, arrayed and enclosed in a replaceable and/or refillable scented solvent cartridge, to generate a scented stream of gas deliverable, for example, in the methods and configurations depicted in FIG. 4.

Figure 4B:
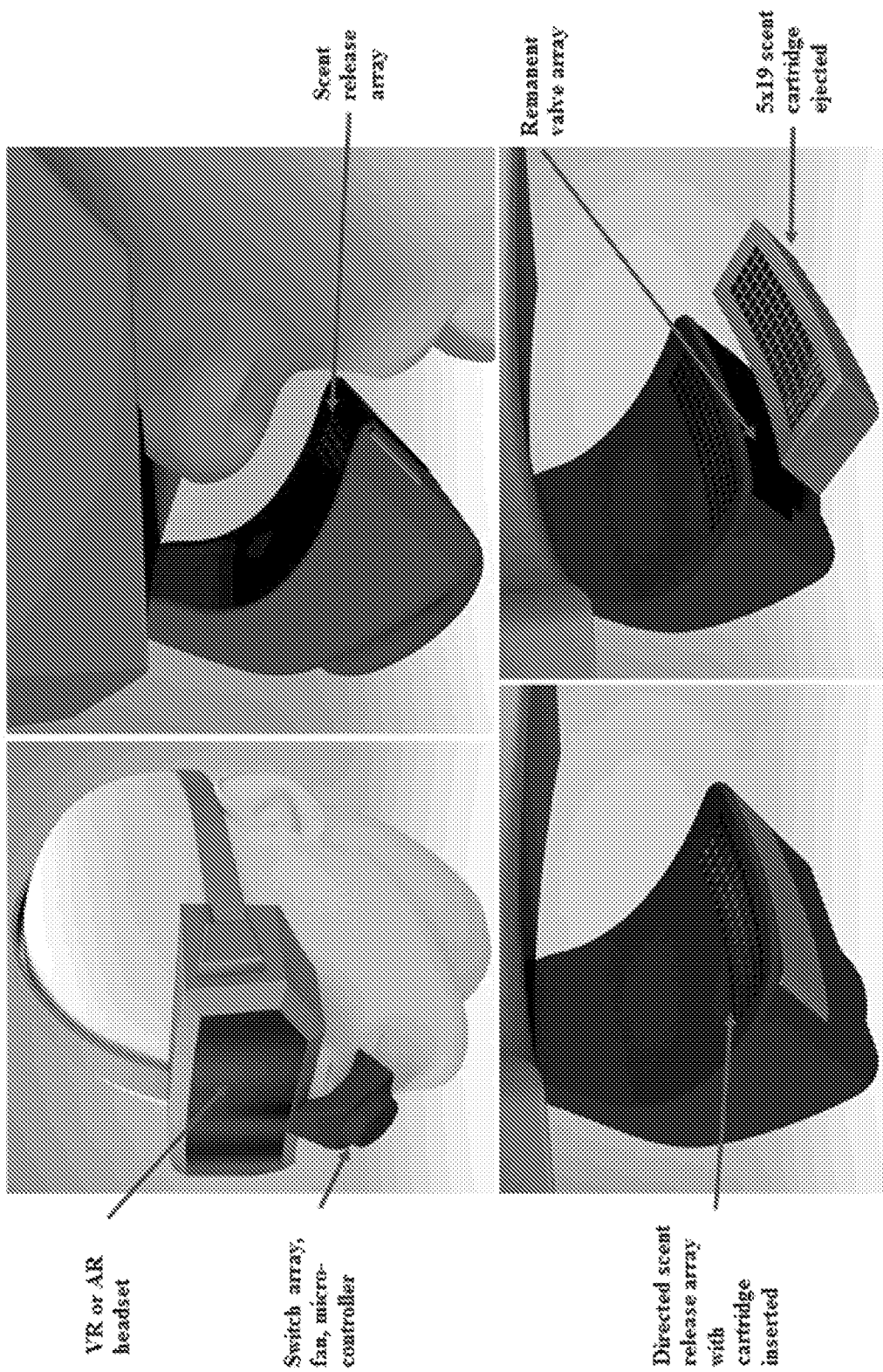
Figure 4C:
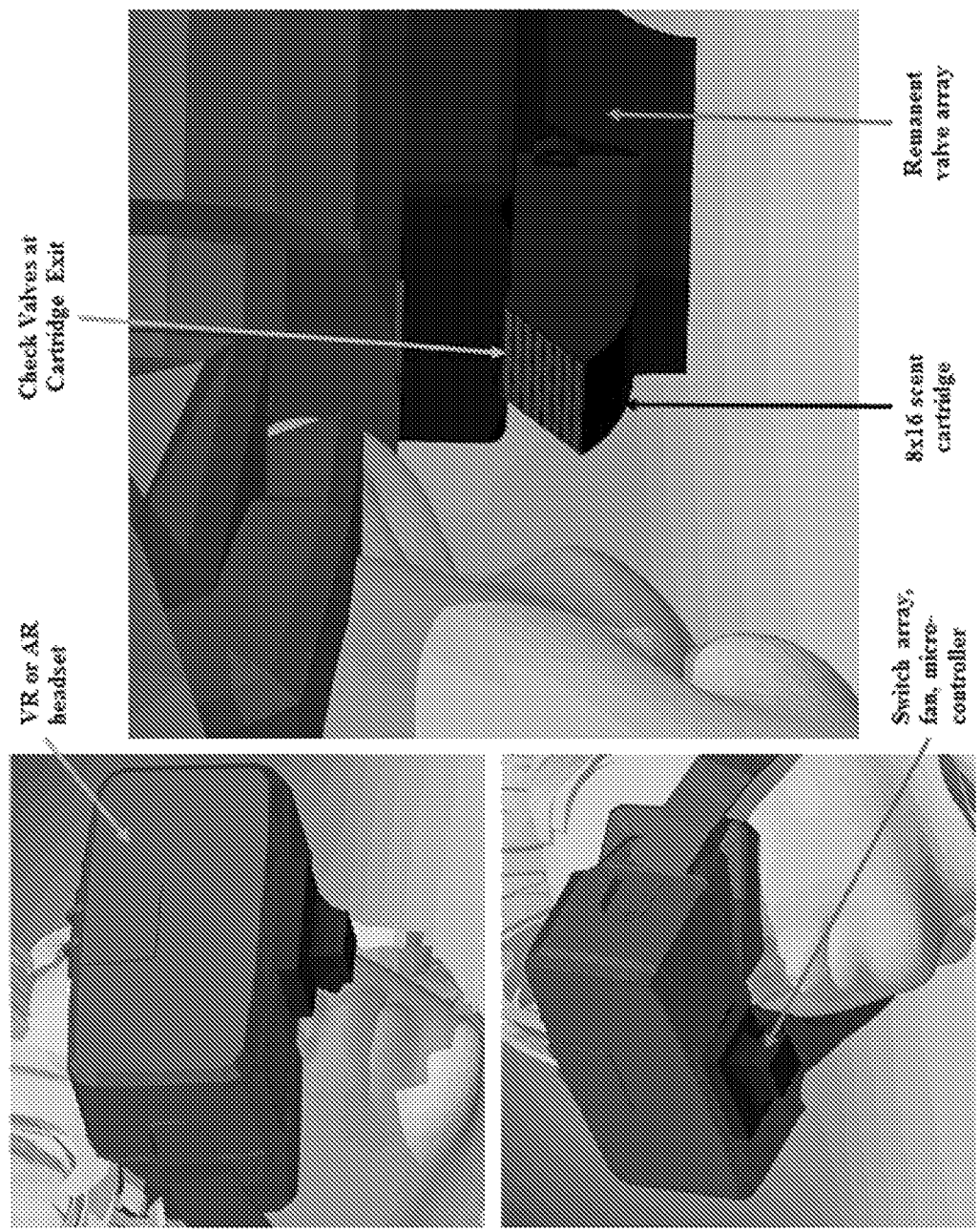
Figure 4D:
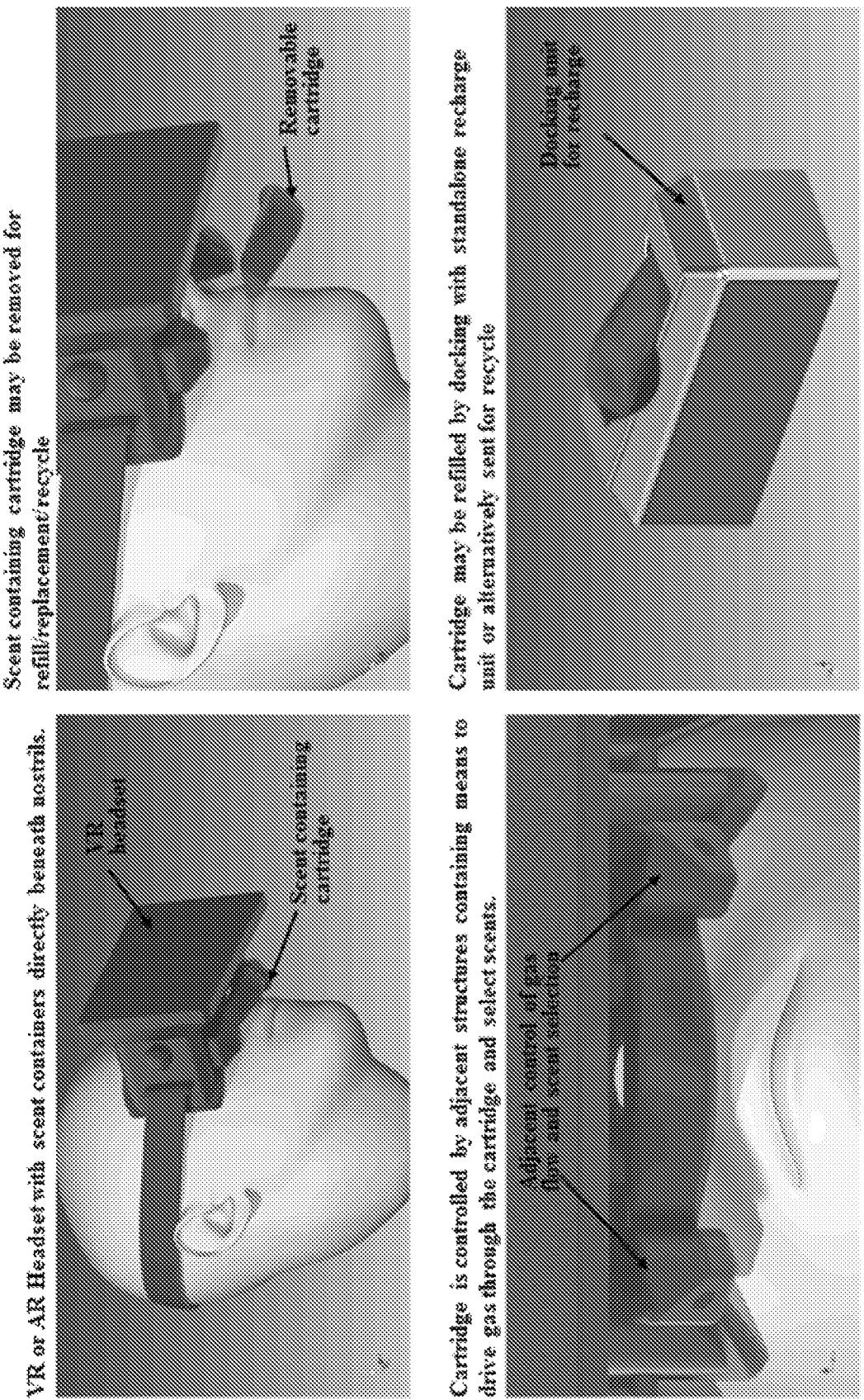

Clause P4.2—A scent delivery device with an interchangeable cartridge, with exit ports controlled by check valves as in P2.1 and P2.2 or remanent magnetization valves, which slots into an array of remanent magnetization valves positioned directly adjacent to and directed into the nose space with scent release accomplished without any delivery channeling (e.g., as in FIG. 4B-4C). This method permits compactness to enable storage of a large number (hundreds) of ready-made scents in a cartridge, and avoids internal deposition issues of using single scent delivery channels and provides for integrity of the delivered scent.

Clause P4.3—As illustrated in FIG. 4B-4O for integrated use with and attachment to or incorporation into VR, AR or mixed reality ("VAR") headgear and eyewear that can be electronically activated for synchronized use with media content presented to the VAR user. These devices can be configured (i) with removable/refillable, integrated scent cartridge and diffuser that is fed by fan or micro-pump elements and gas channels incorporated into or attached to the headset, where the integrated cartridge is attached to (i) the middle section of a VR headset to enable diffusion of scented gas directly into the nosespace; (ii) integrated unit (containing fan, channels, microcontroller and other electronics, battery, replaceable scent cartridge and diffuser) that clips on or otherwise attaches to VAR headwear/eyewear; (iii) configured with scent cartridge placed near the upper or side section(s) of the VAR headwear/eyewear or worn around the neck, on the back, around the belt, or on or near the arm or shoulder; (iv) set on a desktop or some other stationary location.

Clause P4.4—Devices in Clause P4.3, e.g., as illustrated in FIG. 4D-4O, whose components mounted to VAR headgear or eyewear are instead worn and mounted independently to straps or other materials securing the device on the head. Devices in this Clause P4.4 can be worn or operated with or without (or independent of) VAR headgear or eyewear.

Clause P4.5—Devices as in Clauses P1, P2, P3, and P4 in which the actuation of scent release and control can be done by wired signal or wireless signal, magnetic signal, optical signal, sound/vibrational signal, or any cordless remote signals.

Clause P4.6—A method of self-contained, controllable scent delivery, incorporating a magnetically latchable switch structure as in Clause P1, from a handheld, physically separated device with detachable, replaceable or refillable cartridge. This independent hand- or finger-held scent delivery device can be (i) actuated manually by pressing of one or more buttons on the unit itself and automatically deactivated with button release or programmed for timed duration and deactivation, or (ii) automatically or programmably for timed, on-off scent delivery by a wireless signal, cell phone signal, magnetic signal, optical signal, sound/vibrational signal, or any cordless remote signal or sensor. It can also be actuated by the holder or another person who is not holding the device. Such an independent scent delivery device or an array of them, can also be placed on a remote location such as on a table top or on a wall, and actuated by the operator nearby or remotely activated by sensor or using wireless or other remote signaling.

Clause P4.7—Scent delivery to user from dual or multiple scent streams with varying scent compositions and concentrations (e.g., as depicted as in FIGS. 4N & 7E) for purposes of assisting a user of a VAR scent-enabled device with compatible software to determine or impart the impression of origin, and location in 3D or virtual space, as well as characteristics (including, for example, strength of smell) of objects, scenes, events or other content in VAR media.

Clause P4.8—A method of scent delivery from a cartridge or diffuser positioned adjacent to and directed into the nose space with an integrated microphone (e.g., as in FIG. 4O) as a space-saving, integrated and multi-functional design used with:

Clause P 4.8.1—speech recognition that communicates with device software user's instructions or requests specifying scents for immediate, timed or sequential delivery to user or other users with compatible devices and software.

Clause P.4.8.2—user sound input (such as waveform or other sound data) for biofeedback to any scent device with compatible software or other multimedia device.

Clause P4.9—A method of delivery of flavor(s)/taste(s) from a cartridge or diffuser positioned adjacent to and directed at the mouth with integrated scented gas delivery, e.g., as depicted in FIG. 4U, and optionally delivered with other sensory elements such as moisture. The technique is advantageous due to its space-saving, integrated and multi-functional design and the ability to impart a variety of sensory elements to impact or vary impression of taste.

Clause P5.1—An assembly of multiple but individuated tubes or channels for scent transport, or one or a few contamination-resistant tubes or channels that can be shared for delivery of various different scents at different times, such assembly as, for example, can be incorporated into devices as in Clause P4.

Clause P5.2—A method of multi-flow channeling utilizing an internal layer of conductive film or conductive sheet layer which may be resistively heated by passing current through the material to clear any surface depositions, e.g., as in FIG. 5C. This structure and method, in conjunction with exhaust purging of cleared deposition as in FIG. 4W, 5C or 5E to 5G, permits the use of a single channel for multiple flow compositions without cross-contamination. Higher electrical resistivity materials coating or layers are preferred for such resistive heating.

Clause P5.3—A method of multi-flow channeling utilizing an internal layer of conductive film or conductive sheet layer which may be heated inductively by an external solenoid coil activated with alternating current (e.g., as in FIG. 5D). This structure and method, in conjunction with exhaust purging of cleared deposition as in FIG. 4W, 5C or 5E to 5G, provides for energy efficient purging and the use of a single channel for multiple flow compositions. Conductive metals or ceramics can be used as the inductively heatable layer, with ferromagnetic materials, especially those with higher magnetic moment and greater hysteresis loss preferred for such coating or inserted layer.

Clause P5.4—A method of chemical purging of the interior of a multi-flow channel (e.g., as in FIG. 5E), particularly as controlled by latchable remanent magnetization valves.

Clause P5.5—A method of multi-flow channeling utilizing a rigid or semi-rigid external layer supporting a solenoid winding and a loose flexible internal channel with magnetic materials staggered radially and linearly which may be physically shuddered/shaken when the solenoid is activated by an alternating current (e.g., as in FIG. 5F).

Clause P6.1—A method of scent vaporization via coated, encapsulated or hollow, porous micro-nano-particles, optionally with internal magnetic particles for triggered activation in the presence of an alternating magnetic field (e.g., as in FIG. 6A).

Clause P6.2—Divided scent ingredient containers with a solvent reservoir which replenishes an adjacent high surface area substrate via capillary action, pressurized delivery, or similar (e.g., as in FIG. 6B).

Clause P6.3—Divided scent ingredient containers with a solvent reservoir which replenishes an adjacent high surface area substrate via capillary action, pressurized delivery, or similar through branched hollow micro-/nano-channels with porous surfaces to allow the passage of solvent ingredient (e.g., as in FIG. 6C).

Clause P6.4—A technique for mist generation by forcing liquid through a microscale or nanoscale patterned plate with a hydrophobic, lipophobic, or omniphobic surface treatment on the opposite side of the plate (as in FIG. 6B) into a transverse vapor flow. This method is simpler, controllable, and energy efficient.

Clause P6.5—A technique for mist generation by shaking a microscale or nanoscale mesh with hydrophobic, lipophobic, or omniphobic surface treatment submerged partially or wholly in liquid (e.g., as in FIG. 6C) with adjacent transverse vapor flow. This is an efficient way for nebulization and delivery of micro and nano-droplets.

Clause P6.6—A method of achieving continuous vaporization by passing microbubbles or nano-bubbles through patterned plates into filament guided reservoir chamber (e.g., as in FIG. 6D) and out through a second patterned plate. This method provides for increased uptake of vaporized material.

Clause P7.1—Incorporation of a humidifier at or near the outlet port of scent delivery devices (e.g., as in FIG. 7A). This embodiment is useful to prevent discomfort, enable longer duration of use, and provide added sensation to impact user experience.

Clause P7.2—Modulated heating of a scented or unscented gas stream by resistance or inductance heating prior to or after discharge from a gas flow device (e.g., as in FIG. 7B) used in a method for:

Clause P.7.2.1—modulation of ambient intake temperature for optimized scented or unscented gas generation, including blending, and flow.

Clause P.7.2.2—uncontaminated gas delivery to user.

Clause P.7.2.3—optionally standardized or variable gas temperature delivery.

Clause P.7.2.4—delivering the additional sensory component of heat to device user.

Clause P. 7.2.5—modifying user perception of media broadcast or presented to the user of scent devices disclosed herein.

Clause P7.3—Modulated cooling of a scented or unscented gas stream by thermoelectric cooling prior to or after discharge (e.g., as in FIG. 7B) used in a method for:

Clause P. 7.3.1—modulation of ambient intake temperature for optimized scented gas generation, including blending, and flow.

Clause P.7.3.2—optionally standardized or variable gas temperature delivery from the devices of the present document.

Clause P. 7.3.3—delivery which imparts an additional sensory component to the user of the devices of the present document.

Clause P.7.3.4—accompanies user interactivity, interaction, activity or actions of users of the scent devices disclosed herein when using a VAR device or application thereof.

Clause P7.4—Blending and control of concentrations and ratios of gas ingredients via high frequency cycling of remanent magnetization valves, pressure and/or temperature variations and/or metered dilution with unscented gas (as in FIG. 7D) to programmably (according to a specified formula) generate balanced, homogeneous compounds, adjustable in perceived intensity, for scent delivery to users.

Clause P7.5—Delivery of scent flavor(s), optionally synchronized with delivery of sensory elements such as moisture or cold or hot temperature, touch, sound or other sensory media, from scent devices of the present document to users in a method:

Clause P 7.5.1—to impact perception of taste during physical or simulated eating.

Clause P.7.5.2—to enhance shopping for or induce purchases of foods, beverages, flowers or other objects or goods that emit or are associated with smell during VAR, 2D computer, laptop or notebook, cell phone, or online or brick and mortar shopping.

Clause P 7.6—A method of using biosensor feedback of a user's state to dynamically adjust scent output of scent devices (e.g., as in FIG. 7F). This mechanism allows for device automated or programmatic adjustment of scent selection and delivery to alter user's emotional, behavioral or biophysical state or comfort level, or for enhanced or modified experience or interactivity during or in conjunction with live activities or when using compatible scent-enabled VAR devices.

Clause P7.7—Programmed softwares for devices, as in Clause P4, that control and determine scented gas release actuation and delivery, dictate the frequency and duration of release and delivery, and terminate the scent release and delivery, as well as for communication of the foregoing to various other electronic or wireless devices.

Clause P7.8—Software for synchronizing of media streaming or presentation to user, including coordination of timing, sequencing, repetition, etc. of scent selection, blending and scent delivery to user (in blending devices) with image, sound, music (or other media elements) in devices disclosed in the present document.

Clause P7.9—Software for synchronizing of media streaming or presentation to user, including coordination of timing, sequencing, repetition, etc. of scent selection and scent delivery to user (in non-blending devices) with image, sound, music (or other media elements) in devices disclosed in the present document.

Clause P7.9—Software as in Clauses P7.8 and P7.9 that can also be utilized in user-specific actions during media streaming or presentation to user when in a live environment or operating or using a media device such as VAR devices.

Clause P 7.10—Software as in Clauses P7.8 and P7.9 that can also be utilized in user-specific actions or interactions in shopping activities or advertising, including but not limited to utilization of added sensors that detect the motion/vibration such as breathing or sniffing action of the user, sensors that can optically recognize the nature of the object including hand held device approaching the nose, or a motion sensor detecting an object or device moving toward the customer's face to automatically or programmably activate scented gas release and delivery. The software may also remember the customer's habits (especially a repeat customer or frequent customer) and program and activate selected scents for delivery according to programmable criteria, such as customer preferences and habits. The software can also coordinate activation, duration and termination of scent release and delivery between foregoing activities and breathing action of the user.

Clause P7.11—Selected scent(s) in devices as in Clause P4 can be programmably actuated by wireless signals (such as Wi-Fi, magnetic signal, optical signal, sound-activated signal, etc.) or wired signals from any communications or media device with suitable software for example, from a cell phone, TV remote control, laptop computer, wall switch, VAR devices, haptic devices and so forth. Such a hand-held scent release device can hold a large number of dedicated and ready-made scents.

Clause P7.12—Utilization of electronic or wireless microphone activated signals to selectively, automatically or programmably trigger simultaneous or timed activation of scent or drug delivery, or vice versa.

Clause P7.13—Programmable software that recognizes and associates key words, phrases, voice inflections, volume and other sound dynamics with scents in a database, and that coordinates simultaneous or timed on-off scent delivery (optionally with other sensory features such as intensity) with speech or sound.

Clause P7.14—Scent creation by users of devices of Clauses P 3 and P 4 (optionally with facilitated collaboration) via connection to a server or remote server or service (e.g. the 'cloud') containing a search|[M M1]able scent database (scent descriptions and labels with matching formulae, chemical and blending parameters, regulatory restrictions and requirements, and so forth) which may be instructed or programmed by users using scent device software or interface is claimed for the capability to transmit or exchange scent creation information and data (including without limitation formulae) by or between users of scent compatible devices or software by any wired or wireless means.

Clause P7.15—Scent creation software in devices of Clauses P3 and P4 with capability to:

Clause P7.15.1—interpret user digitally written and transmitted or oral descriptions and instructions involving hedonics and psychophysical descriptions of or reactions to smells and to programmably adjust formulae for automatic or timed scent compounding and delivery to user.

Clause P7.15.2—passively interpret, record and/or retrieve content of lightfield array, animation, motion capture, waveform, or other audio, visual or audiovisual or other media data or content and to programmably generate formulae for automatic or timed scent compounding and delivery of scents synchronously or asynchronously to users.

Clause P7.15.3—capture/record, interpret and/or store user data such user facial, body and pose or motion capture and breath inhalation/exhalation pattern or real-time breath intake to programmably generate formulae and accompanying sensory effects (e.g. gas temperature and intensity) for automatic or timed scent compounding and delivery of scents to user. A scent formula may identify scent ingredients by their chemical composition, weight of constituent elements and concentration, and may also identify a proportion of mixing various chemicals or ingredients. A scent formula may, for example, identify entries of a scent database that lists various scent compounds or scents themselves. The scent database may include automated or rule-based adjustments to rebalance formula of scents used in other applications (e.g. perfumes for application to skin).

Clause P7.15.4—receive and interpret external wireless or wired signals and instructions for automatic or timed activation of scent compounding and delivery to one or more users.

Clause P7.15.5—interpret (digital or live) interactions between users and programmably generate formulae for automated or timed scent compounding and delivery of scents to and among them.

Clause P7.15.6—interpret interactivity of user(s) with VAR content and programmably generate formulae for automated or timed scent compounding and delivery of scents to user(s).

Clause P7.15.7—digitally share or provide access to a user's fragrance and flavor database with other users' compatible devices.

Clause P7.15.8—enable other users or third parties (e.g. companies) to send instructions to user's software to automatically or programmably generate formulae for automated or timed scent compounding and delivery of specified scents to one or more users.

Clause P7.15.9—in Clauses P15, to alternatively enable automatic or programmable selection of ready-made scents in scent cartridges of the present technology for automated or programmable delivery of scents to users, in lieu of automated or programmable generation of formulae for compounding and delivery to users.

Clause P7.16—Measurement and evaluation of a scent delivery device user's breathing pattern and/or expected or real-time breathing interval and subsequent timing of scent release to match with the anticipated or presently sensed inhalation, breath pattern or interval as in FIG. 7I.

Clause P8.1—Liquid, mist, powder, gas or suspension drug delivery through Clause P1, P2, P3, P4, P5, P6, and P7 devices through the nostrils, the mouth, or specific regions of the skin for transdermal drug delivery, whether targeting specific organs or for more general dispersal in the body.

Clause P8.2—Orthonasal drug delivery devices for effective, rapid, controlled medication administration using a magnetically actuated switch system having a dispensing mechanism pointed toward or inserted into the nose cavity.

Clause P8.3—Orthonasal drug delivery devices enabling the use of medications in the form of vapor, mist, gas, or powder including suspensions.

Clause P8.4—Orthonasal drug delivery devices to treat lung problems such as asthma or emphysema, or for treatment of allergy problems, are delivered through the orthonasal route.

Clause P8.5—Orthonasal drug delivery devices to treat brain related diseases including Alzheimer's disease, Parkinson's disease, epilepsy, psychopathic drugs or other drugs related to the functioning of brain.

Clause P9—Other applications for devices as in Clause P1-P8 include online, live or VAR social interaction, videoconferencing, shopping, advertisement and other commercial activity, entertainment and other experiences, activities or interactivity; social media; fragrance, flavor or taste formula creation; behavioral modification; therapy; aromatherapy; training; instruction/education; simulations; olfactory displays; online streaming and broadcasts; brick and mortar shopping and bath and beauty products, foods, flowers sampling; orthonasal drug delivery; through-mouth drug delivery with dropwise delivery of drugs using mouth-oriented headset (for patients who cannot easily drink); on-demand fluid synthesis for research or manufacturing, etc.

Implementations of the subject matter and the functional operations described in this patent document can be implemented in various systems, digital electronic circuitry, or in computer software, firmware, or hardware, including the structures disclosed in this specification and their structural equivalents, or in combinations of one or more of them. Implementations of the subject matter described in this specification can be implemented as one or more computer program products, i.e., one or more modules of computer program instructions encoded on a tangible and non-transitory computer readable medium for execution by, or to control the operation of, data processing apparatus. The computer readable medium can be a machine-readable storage device, a machine-readable storage substrate, a memory device, a composition of matter effecting a machine-readable propagated signal, or a combination of one or more of them.

A computer program (also known as a program, software, software application, script, or code) can be written in any form of programming language, including compiled or interpreted languages, and it can be deployed in any form, including as a stand-alone program or as a module, component, subroutine, or other unit suitable for use in a computing environment. A computer program does not necessarily correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program can be deployed to be executed on one computer or on multiple computers that are located at one site or distributed across multiple sites and interconnected by a communication network.

The processes and logic flows described in this specification can be performed by one or more programmable processors executing one or more computer programs to perform functions by operating on input data and generating output. The processes and logic flows can also be performed by, and apparatus can also be implemented as, special purpose logic circuitry, e.g., an FPGA (field programmable gate array) or an ASIC (application specific integrated circuit).

Processors suitable for the execution of a computer program include, by way of example, both general and special purpose microprocessors, and any one or more processors of any kind of digital computer. Generally, a processor will receive instructions and data from a read only memory or a random access memory or both. The essential elements of a computer are a processor for performing instructions and one or more memory devices for storing instructions and data. Generally, a computer will also include, or be operatively coupled to receive data from or transfer data to, or both, one or more mass storage devices for storing data, e.g., magnetic, magneto optical disks, or optical disks. However, a computer need not have such devices. Computer readable media suitable for storing computer program instructions and data include all forms of nonvolatile memory, media and memory devices, including by way of example semiconductor memory devices, e.g., EPROM, EEPROM, and flash memory devices. The processor and the memory can be supplemented by, or incorporated in, special purpose logic circuitry.|[M M2]

While this patent document contains many specifics, these should not be construed as limitations on the scope of any invention or of what may be claimed, but rather as descriptions of features that may be specific to particular embodiments of particular inventions. Certain features that are described in this patent document in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. Moreover, the separation of various system components in the embodiments described in this patent document should not be understood as requiring such separation in all embodiments.

Only a few implementations and examples are described and other implementations, enhancements and variations can be made based on what is described and illustrated in this patent document.

The invention claimed is:

1. A digitally controllable scent creation and delivery apparatus, comprising:
   an array of containers, each container having an inlet through which an input carrier gas flows in, a chamber, called a scent container, for holding a material containing an elementary or a base chemical producing a characteristic odor, called a scent ingredient, or an ingredient, and an outlet through which a mixture of the input gas and the scent ingredient flows out;
   a flow regulation mechanism that controls gas flow through each container based on electromagnetic signals;
   one or more blending chambers coupled to outlets of the containers and having a delivery channel outlet, the blending chambers allowing individual outputs from the outlets of the containers to blend together homogeneously to generate a scent and flow the scent out through the delivery channel outlet; and
   a pressurization chamber coupled to inlets of the containers, and generating the input carrier gas flows,
   wherein the flow regulation mechanism includes a bank of valves coupled to inlets of containers of the array, the valve being operable to control flow of the input gas into inlets of the valves based on the electromagnetic signals, wherein valves in the bank comprise:
   an actuator switch operable to move between an open position and a closed position based on an applied electromagnetic signal to selectively allow passage of gaseous material via a transporting channel from an input of the valve to an output of the valve, and
   wherein the actuator switch includes:
   a magnetically latchable gating valve assembly structured to include (i) a base structure inside the transporting channel and including a high permeability material that forms a passage through the base structure, and (ii) a magnetizable pin assembly set against the base structure in the transporting channel and including a solenoid component, a substantially square-loop magnetization material forming the pin component, and a guide structure containing the pin component, wherein the magnetizable pin component is in contact with the base structure blocking an opening of the passage when the actuator switch is in the closed position, and the magnetizable pin component, when demagnetized, is not in contact with the base structure when the actuator switch is in the open position exposing the opening of the passage, wherein the magnetizable pin has a magnetic switching coercivity of less than 200 oersted;

and wherein the pin component is moveable in the guide structure to move upon a change in a surrounding solenoid's magnetic field to actuate the opening or closing of the actuator switch in the transporting channel.

2. The apparatus of claim 1, wherein each scent container holds a material containing two or more odor producing ingredients based on a scent composition.

3. The apparatus of claim 1, wherein the flow regulation mechanism controls the gas flow by one or more of a gas flow volume, speed, or duration and/or a frequency of valve opening/closing electronic actuation current signal having a digital on-off frequency and/or selection and actuation of one or a number of scent containers in the array.

4. The apparatus of claim 1, wherein the high permeability component of the base structure has a relative permeability of at least 100.

5. The apparatus of claim 1, wherein the array of scent containers are arranged in a one-dimensional pattern, a two-dimensional pattern, or a three-dimensional pattern with the pattern of the scent containers being a linear configuration, a circular configuration, a spherical or random configuration, or another selected configuration.

6. The apparatus of claim 5, wherein the array is rotatable along an axis orthogonal to the two-dimensional pattern to cause at least some scent containers of the array to align with the flow regulation mechanisms, while other scent containers of the array are not aligned with the flow regulation mechanisms.

7. The apparatus of claim 6, further including:

an electronically controlled rotation mechanism coupled to the array for rotating the array and/or coupled to the flow regulation mechanisms for rotating the flow regulation mechanisms in response to a rotation control signal, or an electronically controlled rotation mechanism coupled to the array or to the flow regulation mechanisms comprising one or more high permeability mating pieces which is magnetically linkable with one or more of an adjacent radial series of magnetically latchable pins with solenoids wound around each pin such that an electromagnetic signal can magnetize or demagnetize the pins to rotate the array or flow regulation mechanisms in response to a rotation control signal.

8. The apparatus of claim 1, wherein the array of scent containers form a three-dimensional pattern.

9. The apparatus of claim 8, wherein the three-dimensional pattern comprises multiple two-dimensional arrays of scent containers such that, prior to being delivered out of the delivery channel outlet, the input gas travels through multiple scent containers.

10. The apparatus of claim 8, wherein the three-dimensional pattern comprises a stacked configuration of containers, a mirrored configuration of containers or a nested configuration of containers.

11. The apparatus of claim 1, wherein the array includes a second disk-shaped two-dimensional pattern of scent containers that are placed into radial alignment with the first disk-shaped two-dimensional pattern.

12. The apparatus of claim 11, wherein the disk-shaped two-dimensional pattern of scent containers are removable and replaceable individually or as a unit.

13. The apparatus of claim 11, wherein the disk-shaped two-dimensional pattern of scent containers are refillable with scent material either individually or as a unit by coupling with a separate recharge unit containing additional reserves of scent material delivered into the scent containers by capillary action or by a pressurized injection.

14. The apparatus of claim 11, wherein the array includes additional disk-shaped two-dimensional pattern of scent containers that are placed into radial alignment with the second disk-shaped two-dimensional pattern, the second disk-shaped two-dimensional pattern of scent containers being stacked over the first disk-shaped two-dimensional pattern of scent containers.

15. The apparatus of claim 11, wherein the array includes additional disk-shaped two-dimensional pattern of scent containers that are placed into radial alignment with the second disk-shaped two-dimensional pattern, the second disk-shaped two-dimensional pattern of scent containers being mirrored and stacked over the first disk-shaped two-dimensional pattern of scent containers.

16. The apparatus of claim 1, further including a dehumidifier chamber that dehumidifies the input gas prior to interaction with the scent ingredient and is operable in a mode in which the dehumidifier chamber is always activated, manually activated, or sensor activated.

17. The apparatus of claim 1, further comprising a heating element with placement adjacent or internal to the pressurization chamber, flow regulation mechanisms, blending chamber, or scent delivery channel causing the carrier gas to be heated prior to input or subsequent to output from the scent containers.

18. The apparatus of claim 1, further comprising a cooling element with placement adjacent or internal to the pressurization chamber, flow regulation mechanisms, blending chamber(s), or scent delivery channel causing the scented gas containing ingredients or scent compositions to be cooled prior to mixing with the input gas.

19. The apparatus of claim 1, wherein the cooling element comprises a thermoelectric cooling coil, and wherein the cooling performs modulation of ambient temperature for at least one of (i) an optimized scented gas generation, including blending, and flow, (ii) uncontaminated fluid delivery to a user, (iii) standardized or variable fluid temperature delivery, (iv) delivery which imparts an additional sensory component to the user, (v) modifying user perception of media transmitted to or played in devices, or (vi) limiting or preventing mixing and temperature-induced chemical reactions among at least two scent ingredients for creation of an intended new scent.

20. The apparatus of claim 1, wherein each scent container holds a solid ingredient-specific material interconnected throughout via branching and bifurcated arrangement with a micro-nanoporous structure made of a material selected from metallic, ceramic, polymer, carbon material, with a specific surface area of at least 300 meter square per gram such that the scent liquid is mechanically held in place and the gas flow through the container produces a gaseous mixture of the input gas and the scent ingredient.

21. The apparatus of claim 1, wherein each scent container is divided into two compartments, the first accommodating gas flow from inlet to inlet to outlet and holding a material comprised of a substrate into which liquid scent ingredient or scent composition is distributed to permit exposure to gas flow, and the second section enclosing a liquid scent media reservoir to resupply the substrate section as needed via capillary action or pressurized injection.

22. The apparatus of claim 1, wherein each scent container is divided into two compartments, the first accommodating gas flow from inlet to inlet to outlet and containing a branched hollow micro- or nano-structure with surface porosity into which liquid scent ingredient or scent composition is distributed to permit exposure to gas flow, and the second section enclosing a liquid scent media reservoir to resupply the hollow branched structure of the first section as needed via capillary action or pressurized injection.

23. A digitally controllable scent creation and delivery apparatus, comprising:
- an array of containers, each container having an inlet through which an input carrier gas flows in, a chamber, called a scent container, for holding a material containing an elementary or a base chemical producing a characteristic odor, called a scent ingredient, or an ingredient, and an outlet through which a mixture of the input gas and the scent ingredient flows out;
- a flow regulation mechanism that controls gas flow through each container based on electromagnetic signals;
- one or more blending chambers coupled to outlets of the containers and having a delivery channel outlet, the blending chambers allowing individual outputs from the outlets of the containers to blend together homogeneously to generate a scent and flow the scent out through the delivery channel outlet; and
- a pressurization chamber coupled to inlets of the containers, and generating the input carrier gas flows,
- wherein the array of scent containers are arranged in a one-dimensional pattern, a two-dimensional pattern, or a three-dimensional pattern with the pattern of the scent containers being a linear configuration, a circular configuration, a spherical or random configuration, or another selected configuration, and
- wherein the array is rotatable along an axis orthogonal to the two-dimensional pattern to cause at least some scent containers of the array to align with the flow regulation mechanisms, while other scent containers of the array are not aligned with the flow regulation mechanisms.

24. The apparatus of claim 23, further including:
- an electronically controlled rotation mechanism coupled to the array for rotating the array and/or coupled to the flow regulation mechanisms for rotating the flow regulation mechanisms in response to a rotation control signal, or
- an electronically controlled rotation mechanism coupled to the array or to the flow regulation mechanisms comprising one or more high permeability mating pieces which is magnetically linkable with one or more of an adjacent radial series of magnetically latchable pins with solenoids wound around each pin such that an electromagnetic signal can magnetize or demagnetize the pins to rotate the array or flow regulation mechanisms in response to a rotation control signal.

* * * * *